(12) United States Patent
Perryman et al.

(10) Patent No.: US 8,903,502 B2
(45) Date of Patent: Dec. 2, 2014

(54) METHODS AND DEVICES FOR MODULATING EXCITABLE TISSUE OF THE EXITING SPINAL NERVES

(71) Applicant: Micron Devices LLC, Miami Beach, FL (US)

(72) Inventors: Laura Tyler Perryman, Scottsdale, AZ (US); Chad Andresen, Chandler, AZ (US); Gary King, Fridley, MN (US); Anthony Yeung, Phoenix, AZ (US)

(73) Assignee: Micron Devices LLC, Miami Beach, FL (US)

( * ) Notice: Subject to any disclaimer, the term of this patent is extended or adjusted under 35 U.S.C. 154(b) by 0 days.

(21) Appl. No.: 13/897,427

(22) Filed: May 19, 2013

(65) Prior Publication Data

US 2013/0310901 A1    Nov. 21, 2013

Related U.S. Application Data

(60) Provisional application No. 61/649,834, filed on May 21, 2012.

(51) Int. Cl.

| | |
|---|---|
| *A61N 1/00* | (2006.01) |
| *A61N 1/36* | (2006.01) |
| *A61N 1/05* | (2006.01) |
| *A61N 1/02* | (2006.01) |
| *A61N 1/372* | (2006.01) |
| *A61N 1/378* | (2006.01) |

(52) U.S. Cl.
CPC .......... *A61N 1/0558* (2013.01); *A61N 1/36125* (2013.01); *A61N 1/025* (2013.01); *A61N 1/37229* (2013.01); *A61N 1/36171* (2013.01); *A61N 1/3787* (2013.01)
USPC .......................................................... 607/72

(58) Field of Classification Search
CPC ............ A61N 1/3756; A61N 1/37229; A61N 1/37221; A61N 1/37205
USPC .......................................................... 607/72
See application file for complete search history.

(56) References Cited

U.S. PATENT DOCUMENTS

| 3,662,758 A | 5/1972 | Glover |
| 3,663,758 A | 5/1972 | Erbert |

(Continued)

FOREIGN PATENT DOCUMENTS

| EP | 1588609 A2 | 10/2005 |
| WO | 2011/079309 | 6/2011 |

OTHER PUBLICATIONS

Final Office Action issued in U.S. Appl. No. 13/584,618, dated Aug. 26, 2013, 13 pages.

(Continued)

*Primary Examiner* — Robert N Wieland
(74) *Attorney, Agent, or Firm* — Fish & Richardson P.C.

(57) ABSTRACT

A method for modulating nerve tissue in a body of a patient includes implanting a wireless stimulation device in proximity to a dorsal root ganglion or an exiting nerve root such that an electrode, circuitry and a receiving antenna are positioned completely within the body of the patient. An input signal containing electrical energy and waveform parameters is transmitted to the receiving antenna(s) from a control device located outside of the patient's body via radiative coupling. The circuitry within the stimulation device generates one or more electrical impulses and applies the electrical impulses to the dorsal root ganglion or the exiting nerve roots through the electrode.

46 Claims, 36 Drawing Sheets

(56) References Cited

U.S. PATENT DOCUMENTS

| | | |
|---|---|---|
| 3,727,616 A | 4/1973 | Lenzkes |
| 4,102,344 A | 7/1978 | Conway et al. |
| 4,494,950 A | 1/1985 | Fischell |
| 4,524,774 A | 6/1985 | Hildebrandt |
| 4,525,774 A | 6/1985 | Kino et al. |
| 4,561,443 A | 12/1985 | Hogrefe et al. |
| 4,592,359 A | 6/1986 | Galbraith |
| 4,612,934 A | 9/1986 | Borkan |
| 4,628,933 A | 12/1986 | Michelson |
| 4,736,752 A | 4/1988 | Munck |
| 4,741,339 A | 5/1988 | Harrison et al. |
| 4,750,499 A | 6/1988 | Hoffer |
| 4,837,049 A | 6/1989 | Byers et al. |
| 4,947,844 A | 8/1990 | McDermott |
| 5,058,581 A | 10/1991 | Silvain |
| 5,070,535 A | 12/1991 | Hochmair et al. |
| 5,193,539 A | 3/1993 | Schulman et al. |
| 5,314,458 A | 5/1994 | Najafi et al. |
| 5,343,766 A | 9/1994 | Lee |
| 5,358,514 A | 10/1994 | Schulman et al. |
| 5,411,535 A | 5/1995 | Fujii et al. |
| 5,583,510 A | 12/1996 | Ponnapalli et al. |
| 5,591,217 A | 1/1997 | Barreras |
| 5,626,630 A | 5/1997 | Markowitz et al. |
| 5,735,887 A | 4/1998 | Barreras et al. |
| 5,861,019 A | 1/1999 | Sun et al. |
| 5,991,664 A | 11/1999 | Seligman |
| 5,995,874 A | 11/1999 | Borza |
| 6,141,588 A | 10/2000 | Cox et al. |
| 6,175,752 B1 | 1/2001 | Say et al. |
| 6,350,335 B1 | 2/2002 | Hampel et al. |
| 6,415,184 B1 | 7/2002 | Ishikawa et al. |
| 6,445,953 B1 | 9/2002 | Bulkes et al. |
| 6,445,955 B1 | 9/2002 | Michelson et al. |
| 6,458,157 B1 | 10/2002 | Suaning |
| 6,463,336 B1 | 10/2002 | Mawhinney |
| 6,516,227 B1 | 2/2003 | Meadows et al. |
| 6,564,807 B1 | 5/2003 | Schulman et al. |
| 6,611,715 B1 | 8/2003 | Boveja |
| 6,615,081 B1 | 9/2003 | Boveja |
| 6,647,296 B2 | 11/2003 | Fischell et al. |
| 6,662,052 B1 | 12/2003 | Sarwal et al. |
| 6,690,974 B2 | 2/2004 | Archer et al. |
| 6,889,086 B2 | 5/2005 | Mass et al. |
| 6,895,280 B2 | 5/2005 | Meadows et al. |
| 7,027,874 B1 | 4/2006 | Sawan et al. |
| 7,110,823 B2 | 9/2006 | Whitehurst et al. |
| 7,177,690 B2 | 2/2007 | Woods et al. |
| 7,214,189 B2 | 5/2007 | Zdeblick |
| 7,277,728 B1 | 10/2007 | Kauhanen |
| 7,283,875 B2 | 10/2007 | Larsson |
| 7,317,947 B2 | 1/2008 | Wahlstrand et al. |
| 7,436,752 B2 | 10/2008 | He |
| 7,471,257 B2 | 12/2008 | Candal et al. |
| 7,489,248 B2 | 2/2009 | Gengel et al. |
| 7,620,451 B2 | 11/2009 | Demarais |
| 7,630,771 B2 | 12/2009 | Cauller |
| 7,664,552 B2 | 2/2010 | Wahlstrand et al. |
| 7,738,964 B2 | 6/2010 | Von Arx et al. |
| 7,741,734 B2 | 6/2010 | Joannopoulos et al. |
| 7,765,013 B2 | 7/2010 | Blick et al. |
| 7,853,333 B2 | 12/2010 | Demarais |
| 7,869,885 B2 | 1/2011 | Begnaud et al. |
| 7,894,905 B2 | 2/2011 | Pless et al. |
| 7,904,170 B2 | 3/2011 | Harding |
| 7,908,014 B2 | 3/2011 | Schulman et al. |
| 7,939,346 B2 | 5/2011 | Blick et al. |
| 8,170,672 B2 | 5/2012 | Weiss et al. |
| 8,332,040 B1 | 12/2012 | Winstrom |
| 2004/0059392 A1 | 3/2004 | Parramon et al. |
| 2004/0082979 A1 | 4/2004 | Tong et al. |
| 2004/0127942 A1 | 7/2004 | Yomtov et al. |
| 2004/0138723 A1* | 7/2004 | Malick et al. ............... 607/57 |
| 2004/0176803 A1 | 9/2004 | Whelan et al. |
| 2005/0137668 A1 | 6/2005 | Khan |
| 2006/0085039 A1 | 4/2006 | Hastings et al. |
| 2006/0085042 A1 | 4/2006 | Hastings et al. |
| 2006/0161225 A1 | 7/2006 | Sormann et al. |
| 2006/0287686 A1 | 12/2006 | Cullen et al. |
| 2006/0289528 A1 | 12/2006 | Chiu et al. |
| 2007/0100395 A1 | 5/2007 | Ibrahim |
| 2007/0100935 A1 | 5/2007 | Miyazaki et al. |
| 2007/0106337 A1 | 5/2007 | Errico et al. |
| 2007/0156179 A1* | 7/2007 | S.E. ............................... 607/2 |
| 2007/0213773 A1 | 9/2007 | Hill et al. |
| 2007/0213783 A1 | 9/2007 | Pless |
| 2007/0254632 A1 | 11/2007 | Beadle et al. |
| 2007/0265543 A1 | 11/2007 | VanSickle et al. |
| 2007/0265690 A1 | 11/2007 | Lichtenstein et al. |
| 2007/0288066 A1 | 12/2007 | Christman et al. |
| 2008/0010358 A1 | 1/2008 | Jin |
| 2008/0046012 A1 | 2/2008 | Covalin et al. |
| 2008/0077188 A1 | 3/2008 | Denker et al. |
| 2008/0266123 A1 | 10/2008 | Ales et al. |
| 2008/0281244 A1 | 11/2008 | Jacobs |
| 2009/0099405 A1 | 4/2009 | Schneider et al. |
| 2009/0105784 A1 | 4/2009 | Massoud-Ansari |
| 2009/0132002 A1 | 5/2009 | Kieval |
| 2009/0132003 A1 | 5/2009 | Borgens et al. |
| 2009/0200985 A1 | 8/2009 | Zane et al. |
| 2009/0204170 A1 | 8/2009 | Hastings et al. |
| 2009/0234407 A1 | 9/2009 | Hastings et al. |
| 2009/0248112 A1 | 10/2009 | Mumbru et al. |
| 2010/0053789 A1 | 3/2010 | Duric et al. |
| 2010/0114198 A1 | 5/2010 | Donofrio et al. |
| 2010/0125269 A1 | 5/2010 | Emmons et al. |
| 2010/0168818 A1 | 7/2010 | Barror et al. |
| 2010/0174340 A1 | 7/2010 | Simon |
| 2010/0179449 A1 | 7/2010 | Chow et al. |
| 2010/0198039 A1 | 8/2010 | Towe |
| 2010/0231382 A1 | 9/2010 | Tayrani et al. |
| 2010/0234922 A1 | 9/2010 | Forsell |
| 2010/0268298 A1 | 10/2010 | Moffitt et al. |
| 2010/0298742 A1 | 11/2010 | Perlman et al. |
| 2010/0331934 A1 | 12/2010 | McDonald et al. |
| 2011/0040350 A1 | 2/2011 | Griffith |
| 2011/0074342 A1 | 3/2011 | MacLaughlin |
| 2011/0098583 A1 | 4/2011 | Pandia et al. |
| 2011/0120822 A1 | 5/2011 | Kondou et al. |
| 2011/0121822 A1 | 5/2011 | Parsche |
| 2011/0125214 A1 | 5/2011 | Goetz et al. |
| 2011/0130804 A1 | 6/2011 | Lin et al. |
| 2011/0144468 A1* | 6/2011 | Boggs et al. ................ 600/373 |
| 2011/0190849 A1 | 8/2011 | Faltys et al. |
| 2012/0215218 A1* | 8/2012 | Lipani ............................ 606/41 |
| 2013/0165991 A1* | 6/2013 | Kim et al. ...................... 607/46 |

OTHER PUBLICATIONS

International Preliminary Report on Patentability issued in International Application No. PCT/US2012/050633, issued Feb. 18, 2014, 7 pages.

International Preliminary Report on Patentability issued in International Application No. PCT/US2012/055746, issued Mar. 18, 2014, 10 pages.

International Search Report and Written Opinion issued in International Application No. PCTUS2012048903, dated Oct. 10, 2012, 10 pages.

International Search Report and Written Opinion issued in International Application No. PCTUS 1250633, dated Oct. 23, 2012, 8 pages.

International Search Report and Written Opinion issued in International Application No. PCT/US2012/55746, dated Jan. 3, 2013, 11 pages.

International Search Report and Written Opinion issued in International Application No. PCT/US2012/032200, dated Jul. 27, 2012, 13 pages.

International Search Report and Written Opinion or the Declaration issued in International Application No. PCTUS1223029, dated May 16, 2012, 11 pages.

Non-Final Office Action issued in U.S. Appl. No. 13/551,050, dated Mar. 4, 2014, 30 pages.

(56) References Cited

OTHER PUBLICATIONS

Non-Final Office Action issued in U.S. Appl. No. 13/562,221, dated Jan. 29, 2014, 30 pages.

Non-Final Office Action issued in U.S. Appl. No. 13/584,618 dated Jun. 12, 2013, 15 pages.

Non-Final Office Action issued in U.S. Appl. No. 13/621,530, dated Apr. 11, 2014, 15 pages.

Notice of Allowance issued in U.S. Appl. No. 13/584,618, dated May 16, 2014, 8 pages.

* cited by examiner

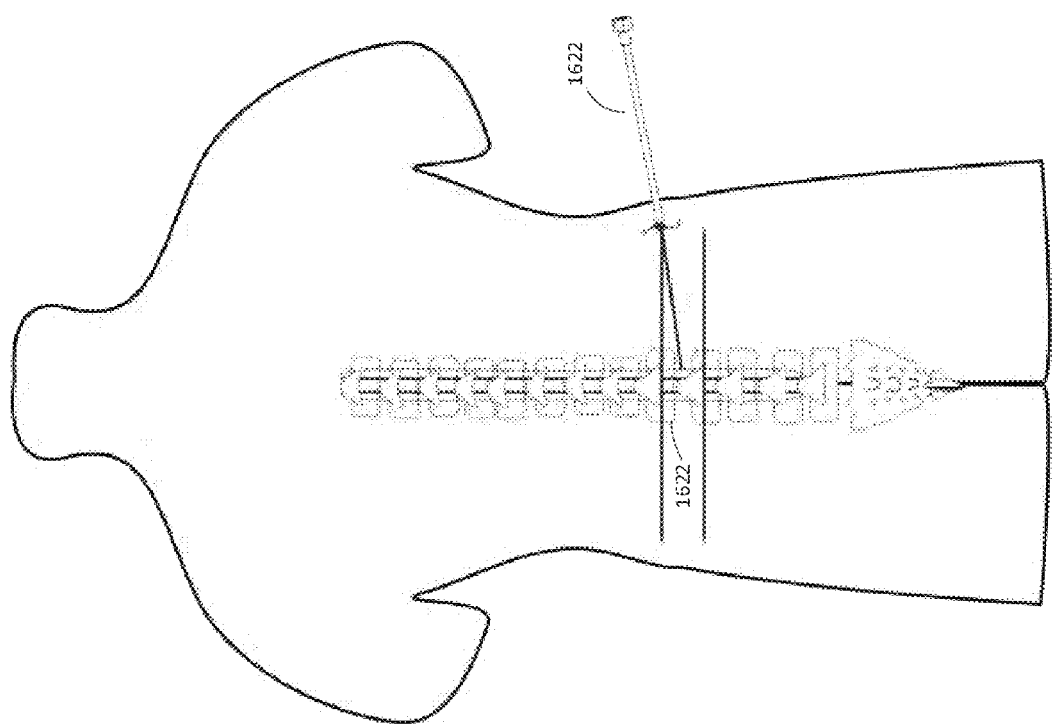

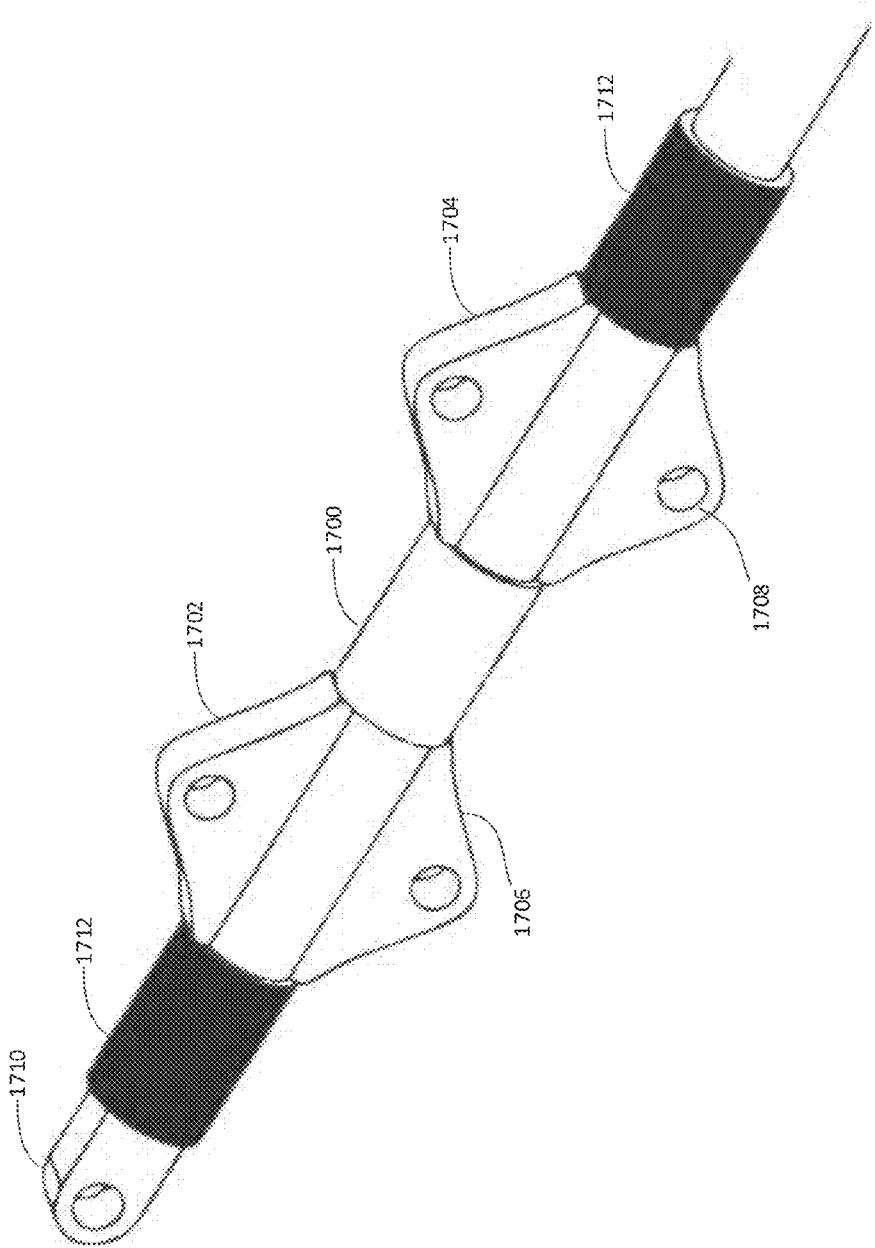

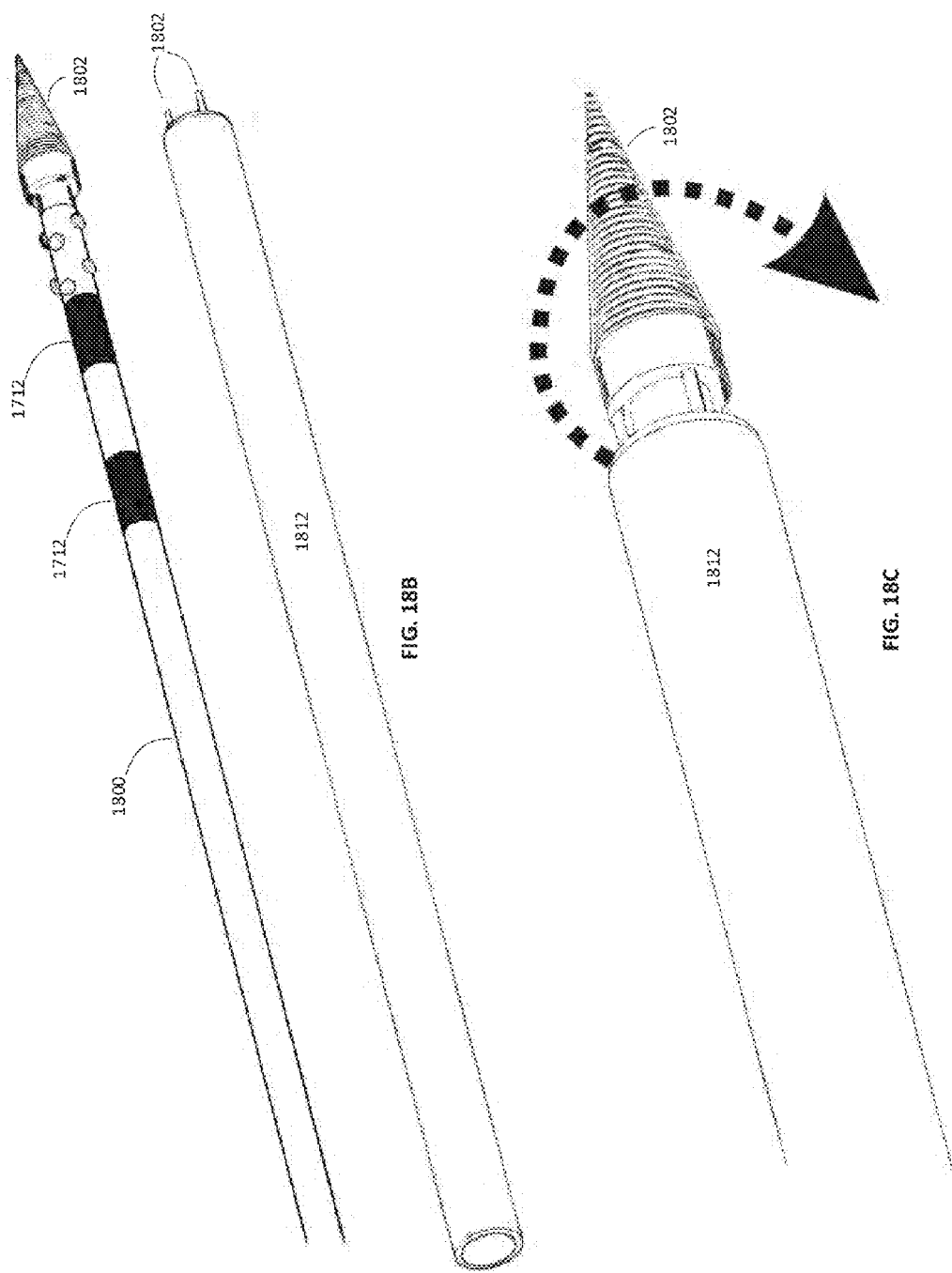

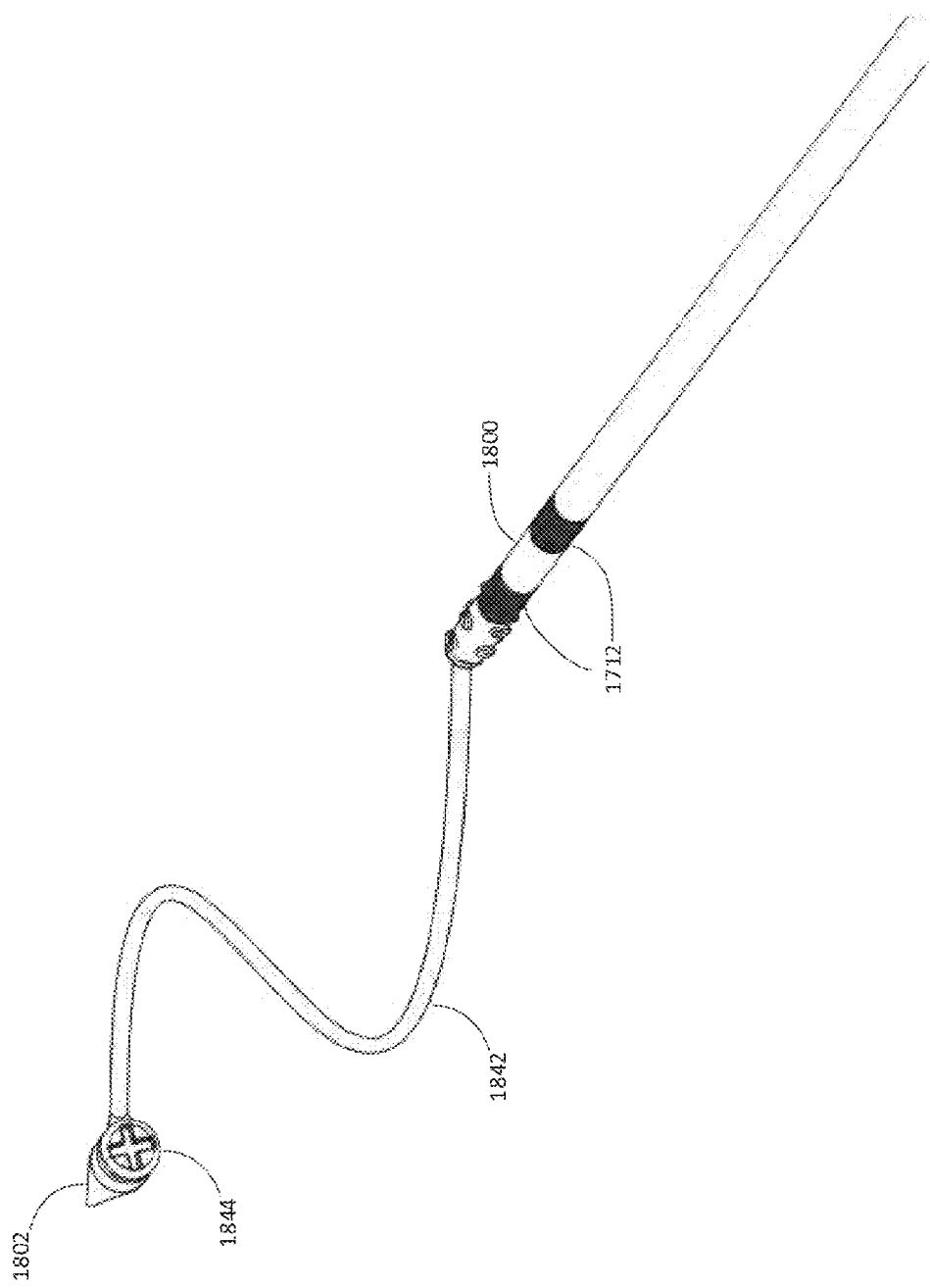

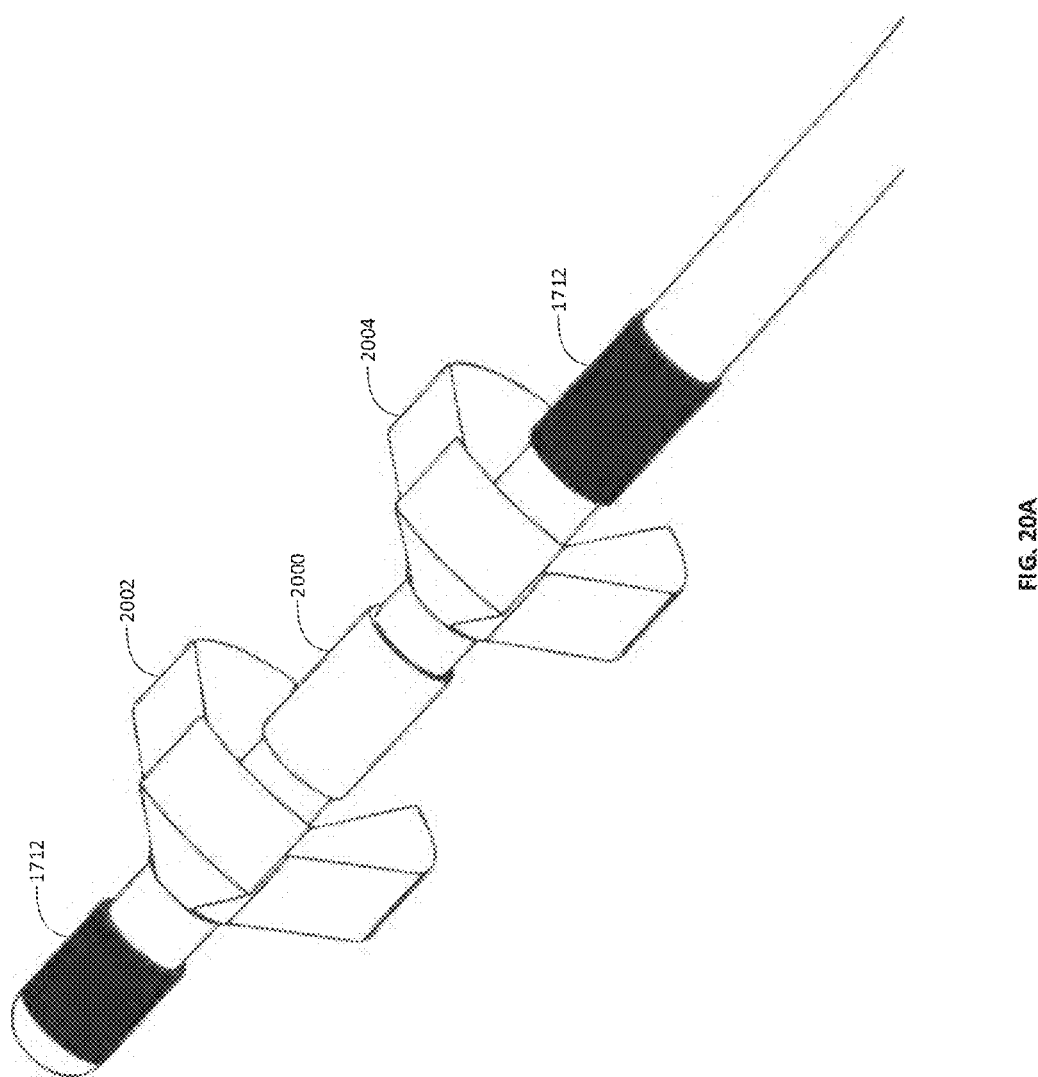

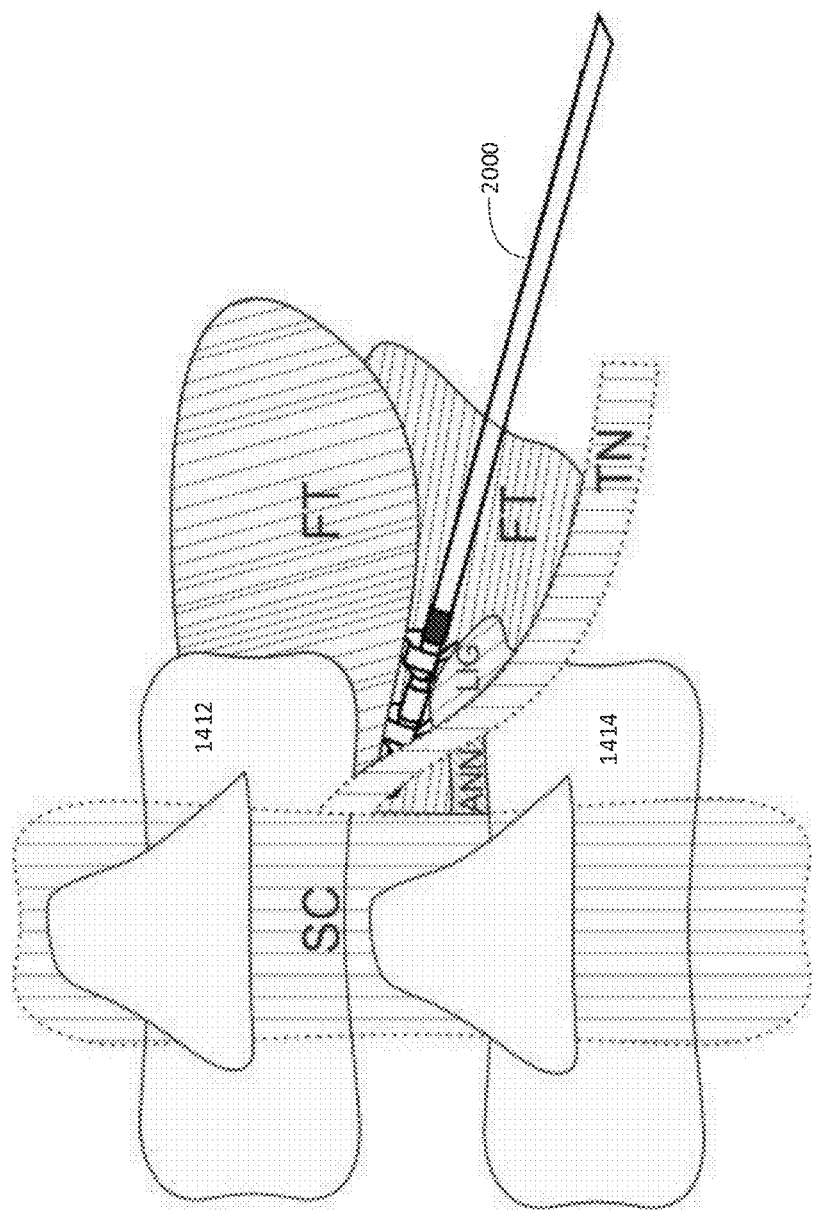

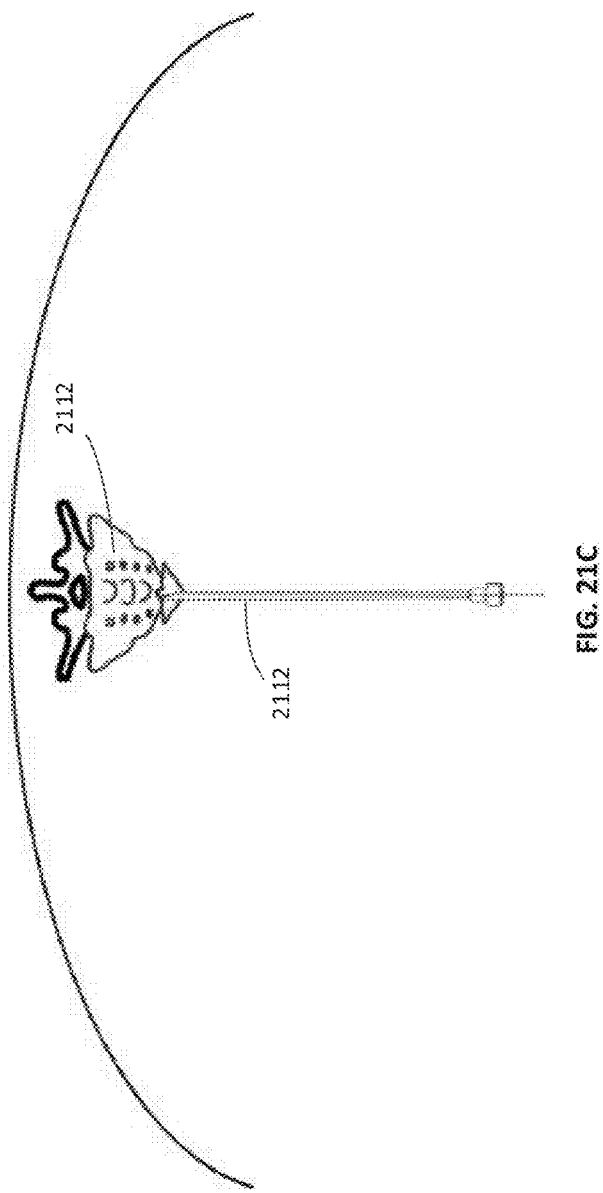

METHODS AND DEVICES FOR MODULATING EXCITABLE TISSUE OF THE EXITING SPINAL NERVES

CROSS-REFERENCE TO RELATED APPLICATIONS

This application claims the benefit of priority of U.S. Provisional Patent Application No. 61/649,834 filed May 21, 2012 and is related to the following commonly-assigned patent applications: U.S. patent application Ser. No. 13/551,050 (filed Jul. 17, 2012), Ser. No. 13/562,221 (filed Jul. 30, 2012) and Ser. No. 13/584,618 (filed Aug. 13, 2012) and PCT Patent Application Nos. PCT/US2012/023029 (filed Jan. 27, 2012), PCT/US2012/032200 (filed Apr. 4, 2012), PCT/US2012/048903 filed Jul. 30, 2012), PCT/US2012/050633 (filed Aug. 13, 2012) and PCT/US2012/055746 (filed Sep. 15, 2012). The complete disclosures of all of the above patent applications are hereby incorporated by reference in their entirety for all purposes.

BACKGROUND OF THE INVENTION

The field of the present invention relates generally to the delivery of energy impulses (and/or fields) to bodily tissues for therapeutic purposes and more specifically to devices and methods for modulating excitable tissue of the exiting spinal nerves to treat various disorders, such as chronic pain, inflammation and/or other disorders.

Modulation of excitable tissue in the body by electrical stimulation has become an important type of therapy for patients with chronic disabling conditions, including chronic pain, pain associated with cancer, incontinence, problems of movement initiation and control, involuntary movements, vascular insufficiency, heart arrhythmias, obesity, diabetes, craniofacial pain and more. A variety of therapeutic intra-body electrical stimulation techniques can treat these conditions. Typically, such devices include an implantable lead with two or more electrodes attached by a connector to a subcutaneous battery-operated implantable pulse generator (IPG) or other charge storage to provide power and create the electrical impulses carried by hard wire to the lead body containing the electrodes.

Traditional wired leads have several disadvantages, including: a large surgical pocket to house the implantable pulse generator with a battery or charge storage component; extensions and connectors between the IPG and the proximal end of the lead that are housed under the skin, and, a need to recharge or explant the IPG. Having the IPG tethered to the IPG within the patient's body is a disadvantage because this connection can cause lead migration and the possibility for loss of therapy from a disconnection from the IPG exists and has plagued the industry. Placement of an IPG also requires an invasive surgical procedure as the physician must create a pocket of a substantial size of 18 to 75 cc within the body of the patient, typically around the abdomen or buttocks area. Tunneling is also required to connect the classic IPG to the proximal end of the lead located by the targeted nerves. The lead or extension wires must be routed under the skin to reach the classic wired implantable lead. However, devices that utilize a battery-powered or charge-storage component are no longer functional once the battery cannot be recharged or charge cannot be stored. Consequently, for an implanted device, a patient would need to undergo a subsequent surgical procedure to obtain a functional replacement device.

Electrical stimulation of the spinal column and the exiting nerve bundles leaving the spinal cord as a neural modulation therapy and has been used in pain management since the 1970s. Implanted leads containing an electrode array with various polarity settings are used to pass pulsatile waveforms of energy with controllable variations in frequency, pulse width and amplitude. Two or more electrodes are required to be in the array to create an electrical volume conduction area that activates nearby neural structures. The modifications in the parameter settings of the waveform enable the selectively of activating various nerve fibers with different diameters providing various positive therapeutic benefits.

Wired leads for spinal cord stimulation are typically positioned in the epidural space, or through the epidural space, and onto or near exiting nerve bundles. For spinal cord stimulation to be most effective, the volume conduction area of activation must map over the correct dermatomes of the spine. Since most pain can originate from several dermatome levels, one or two wired leads with up to eight electrodes are placed in the epidural space. In cases were two leads are used, the configurations are typically with the leads parallel to each other or at two different vertical locations. The further away from the centerline of the spinal cord within the epidural space, the more specific the nerve recruitment will be for a specific dermatome level. In cases where pain is specific to a certain region, lead placements have been placed closer to the exiting nerve bundle by crossing through the epidural space or by hardwiring with a cut down or other invasive maneuver to the exiting nerve.

Wired leads are associated with numerous failure modes, including, for example, mechanical dislodgement due to motion, acceleration and impingement of the lead electrode assembly, infection and uncomfortable irritation. In particular, longitudinal movement of the lead can move the surface electrodes, making them bear on a different portion of the spinal cord, no longer treating the pain. A transverse or side-to-side movement of the lead can have the same effect, and can also move the electrodes further away from the spinal cord, weakening the signal and/or requiring greater power to reach the targeted nerves. Increased power consumption can decrease battery life, which may require more frequency surgical replacement of the implanted battery.

SUMMARY OF THE INVENTION

The present invention discloses systems, methods and devices for modulating excitable tissue of the exiting spinal nerves with a wireless implantable lead which generates power from radiated energy and does not rely upon battery power or charge storage for operation. Therefore, the life of the implantable lead is not limited by the life of the battery or the ability to store charge. Further, the technology claimed herein facilitates a smaller form factor, which results in a less invasive surgical procedure for placement of the device and reduces scarring from a reduction in the amount of bodily tissue in contact with the implanted device.

In one aspect of the invention, a method for modulating the excitable tissue includes implanting of a wireless stimulation device in proximity to the exiting nerve roots such that the device is completely contained within the body of the patient in proximity to one or more nerves. An input signal containing electrical energy is transmitted from a control device outside of the patient's body to the stimulation device via radiative coupling such that the devices generates an electrical impulse using the electrical energy contained in the input signal. The electrical impulse is applied to the exiting nerve root through the induced electrical field sufficient to modulate the nerve(s). In a preferred embodiment, the stimulation device contains one or more electrodes, one or more antennas for receiving the input signal and circuitry for generating the electrical impulse from the input signal. The entire stimulation device is self-contained and is not connected to an extension wire or an IPG.

One of the advantages of using the wireless stimulation device of the present invention is that the electrodes can be positioned in very targeted areas near exiting spinal nerves. Unlike previous spinal cord simulators wherein a long row of electrodes must be implanted throughout the epidural space and then connected to IPG, the wireless stimulation device of the present invention may be positioned in precise targeted locations within the patient such that the electrical stimulation is localized in the vicinity of the targeted exiting nerve roots. This allows the clinician to place the wireless stimulation device directly to target areas within the patient that were previously not possible for wired implantable leads that required extensive tunneling and a port of the IPG (typically limited to 16 electrodes).

In certain embodiments, the stimulation device is coated with a biocompatible material and the body of the lead is treated to have grooves, divots, or other method of increasing surface area to encourage faster scar in. The electrodes preferably comprise of a material of platinum, platinum/iridium or other biocompatible alloy. The electrical impulse generated by the stimulation device preferably has a frequency of 10,000 Hz or less and a pulse width of 1 ms or less.

In another aspect of the invention, a method for modulating excitable tissue comprises applying a nerve block to one or more target locations within the body of a patient and assessing which of these locations results in optimal pain relief for the patient. A wireless stimulation device is then implanted at the optimal target location and an input signal is delivered to the lead through radiative coupling. The stimulation device transforms the input signal into an electrical impulse that is sufficient to modulate nerves or nerve ganglions at the optimal target location.

One of the advantages of this method is that the clinician may now provide a more permanent electrical stimulation directly to a targeted area that responds to a nerve block. Nerve blocks are often successfully used to temporarily relieve pain in areas that are not accessible with wired leads. Another advantage of the present invention is that it does not require a long row of electrodes to be implanted into the patient and then tested to determine the proper location for stimulation. Instead, the physician is able to determine this location through the application of one or more nerve blocks, and then follow-up the nerve block(s) with implantation of the wireless stimulation device in the precise location of the nerve block(s) that provide relief to the patient.

In yet another aspect of the invention, a method for treating post-operative pain by modulating excitable tissue includes performing a surgical procedure on the patient, such as a spinal fusion procedure (e.g., a TLIF), and then implanting a wireless stimulation device of the present invention in the location of the surgical procedure. An input signal is transmitted to the wireless stimulation device and converted into an electrical impulse sufficient to modulate nerves in or around the location of the surgical procedure. The application of electrical stimulation to a surgery site reduces post-operative pain and potentially decreases recovery time.

In another aspect of the present invention, a method for modulating excitable tissue includes advancing at least a distal portion of a wireless stimulation device through the intervertebral foramen into the Kambin's triangle and anchoring the distal portion of the device into the adjacent nearby exiting nerve. In a preferred embodiment, a wireless stimulation device is positioned near the intervertebral foramen opening and the wireless stimulation device is advanced through the lumen of the introducer and out of the distal opening of the lumen such that one or more electrodes pass through the intervertebral foramen opening. The lumen may be, for example, a cannula, spinal needle, endoscope or the like.

In certain embodiments, the distal portion of the wireless stimulation device may include at least one suture location. In this embodiment, the distal portion of the electrode lead is suture to tissue or bone near the Kambin's triangle, such as a facet joint, vertebral body, pedicle, annulus or a facet capsule. In other embodiments, the distal portion of the wireless stimulation device comprises one or more fixation prongs. In these embodiments, the method includes embedding the fixation prongs into tissue within Kambin's triangle. In yet another embodiment, the distal portion of the wireless stimulation device comprises screw-tips and the method includes rotating the screw-tips into the tissue within Kambin's triangle. The implantation step may further include visualizing the implanting process by fluoroscopy or through an endoscope.

In another aspect of the invention, a method for modulating excitable tissue includes advancing a distal portion of a wireless stimulation device through a sacral hiatus opening to place the device in the region of the sacral exiting nerve bundle. In a preferred embodiment, the distal portion of the wireless stimulation device is introduced through the Kambin's Triangle, and then advanced along the dorsal or ventral epidural space behind the spinal cord to a target region. Once the target region is reached, the distal portion of the wireless stimulation device is positioned and fixated in the intervertebral foraminal space so that the electrical field of conduction remains in close proximity to the exiting nerve root or nerve ganglion. An electrical impulse is applied through the electrodes sufficient to modulate one or more nerves within the exiting nerve root or nerve ganglion.

In another aspect of the invention, a device for modulating excitable tissue in a patient's body comprises a lead including one or more electrodes, circuitry and a receiving antenna, all of which are fully encapsulated in one self contained device without a connector or wires to a power source. The wireless stimulation device is sized and configured for placement adjacent to or near a target site at an exiting nerve root or a nerve ganglion. The receiving antenna is configured to receive an input signal containing electrical energy and waveform parameters through radiative coupling from a transmitter located outside of the patient's body and the circuitry is configured to generate an electrical impulse from the input signal sufficient to modulate a nerve or a nerve ganglion at the target site.

In a preferred embodiment, the wireless stimulation device has a diameter of less than 1.8 mm and is sized and shaped for advancement with an introducer or needle through an intervertebral foramen into the Kambin's triangle region.

In another embodiment, the wireless stimulation device has a distal portion sized and shaped for advancement with an introducer or needle through a sacral hiatus opening to be placed in parallel with the exiting sacral nerves leaving the spinal cord. The distal portion of the electrode lead comprises of one or more fixation elements for attaching the lead to tissue or bone adjacent to or near the Kambin's triangle. The fixation elements comprise one of a suturing addendum, a rotating screw-tip or a fixation prong.

In yet another aspect of the invention, a system for modulating excitable tissue in a body of a patient comprises a lead having one or more electrodes and a receiving antenna and being sized and configured for placement adjacent to or near a target site at an exiting nerve root or a nerve ganglion and a control device having a transmitter located outside of the patient's body and configured to transmit an input signal containing electrical energy and waveform parameters to the receiving antenna through radiative coupling. The wireless stimulation device is configured to generate an electrical impulse from the input signal sufficient to modulate a nerve or a nerve ganglion at a target site within the patient's body. In a preferred embodiment, the control device comprises a transmitting antenna configured to transmit the input signal through a carrier signal having a frequency between about 800 KHz and 5.8 GHz and a pulse generator configured to generate an electrical impulse with a frequency of about 10 to 500 Hz. The control device is configured to transmit the input signal at least 10 cm, preferably at least 13 cm, under an outer skin surface of the patient through tissue to the target site.

The novel systems, devices and methods for modulating excitable tissue of the exiting spinal nerves are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

Incorporation By Reference

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 16B is a dorsal-ventral view of the placement of the wireless stimulation device through an angular approach to the Kambin's triangle;

FIG. 17A illustrates an alternative embodiment of a wireless stimulation device according to the present invention with suturing addendums;

FIG. 18B illustrates a wireless stimulation device with a screw-tip and a tool for securing the wireless stimulation device;

FIG. 18C illustrates a method of the present invention for securing the stimulation device of FIG. 18B;

FIG. 18D illustrates another embodiment of the present invention including a wireless stimulation device attached to a screw-tip by an extruded tethering component;

FIG. 20A illustrates another embodiment of an implantable stimulation device with barbed features;

FIG. 20B illustrates a method for anchoring the stimulation device of FIG. 20A;

FIG. 21C is a caudal-cranial view of the placement of a wireless stimulation device utilizing a spinal needle through the sacral hiatus.

DETAILED DESCRIPTION OF THE PREFERRED EMBODIMENTS

In various implementations, systems and methods are disclosed for applying one or more electrical impulses to targeted excitable tissue, such as nerves, for treating chronic pain, inflammation and/or other disorders. In certain embodiments, a wireless stimulation device may be used to send electrical energy to targeted nerve tissue by using remote radio frequency (RF) energy with neither cables nor inductive coupling to power the passive implanted wireless stimulation device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

The wireless stimulation device of the present invention can include an implantable lead body that includes an enclosure that houses one or more conductive antennas (for example, dipole or patch antennas), internal circuitry for frequency waveform and electrical energy rectification, and one or more electrodes allowing for neural stimulation of nearby tissue. The wireless stimulation device may further comprise an external controller and antenna for sending radio frequency or microwave energy from an external source to the implantable lead with neither cables nor inductive coupling to power the wireless stimulation device.

In various embodiments, the implantable wireless stimulation device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil. Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which have been previously incorporated by reference.

Figure 1:
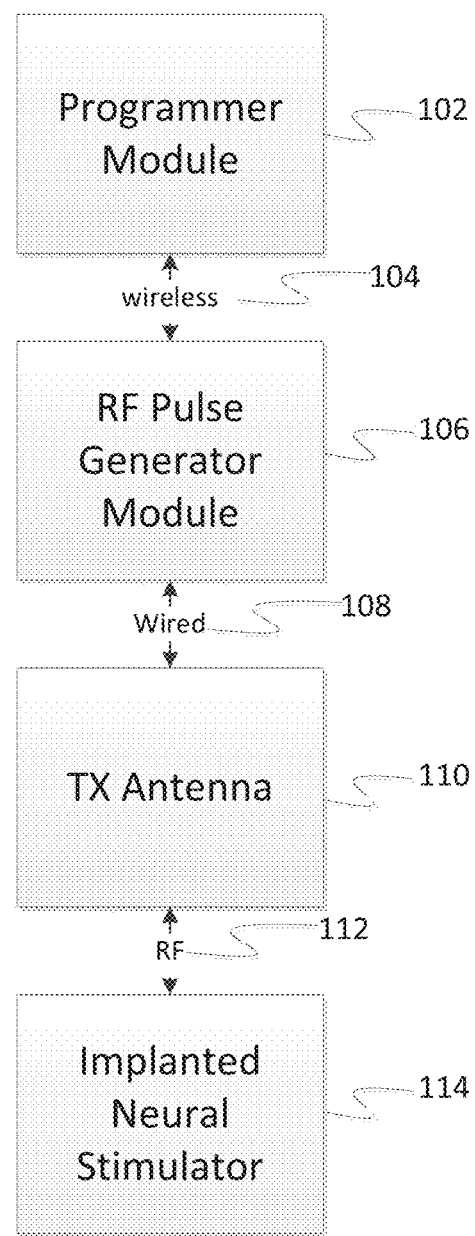
FIG. 1 depicts a high-level diagram of an example of a wireless stimulation device.

FIG. 1 depicts a high-level diagram of an example of a wireless stimulation device. The wireless stimulation device may include four major components, namely, a programmer module 102, a RF pulse generator module 106, a transmit (TX) antenna 110 (for example, a patch antenna, slot antenna, or a dipole antenna), and an implanted wireless stimulation device 114. The programmer module 102 may be a computer device, such as a smart phone, running a software application that supports a wireless connection 114, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted neural stimulator module 114. The TX antenna 110 communicates with the implanted neural stimulator module 114 through an RF interface. For instance, the TX antenna 110 radiates an RF transmission signal that is modulated and encoded by the RF pulse generator module 110. The implanted wireless stimulation device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted stimulation module 114. This input signal contains energy and may contain information encoding stimulus waveforms to be applied at the electrodes of the implanted neural stimulator module 114. In some implementations, the power level of this input signal directly determines an applied amplitude (for example, power, current, or voltage) of the one or more electrical pulses created using the electrical energy contained in the input signal. Within the implanted wireless stimulation device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulation device module 114, which is a passive stimulator. In either event, receiver circuit(s) internal to the wireless stimulation device 114 can capture the energy radiated by the TX antenna 110 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 106 can remotely control the stimulus parameters (that is, the parameters of the electrical pulses applied to the neural tissue) and monitor feedback from the wireless stimulation device 114 based on RF signals received from the implanted wireless stimulation device module 114. A feedback detection algorithm implemented by the RF pulse generator module 106 can monitor data sent wirelessly from the implanted wireless stimulation device module 114, including information about the energy that the implanted wireless stimulation device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulation device 114 are monitored and used to determine the appropriate level of neural stimulation current for maintaining effective neuronal activation, or, in some cases, the patient can manually adjust the output signals in an open loop control method.

Figure 2:
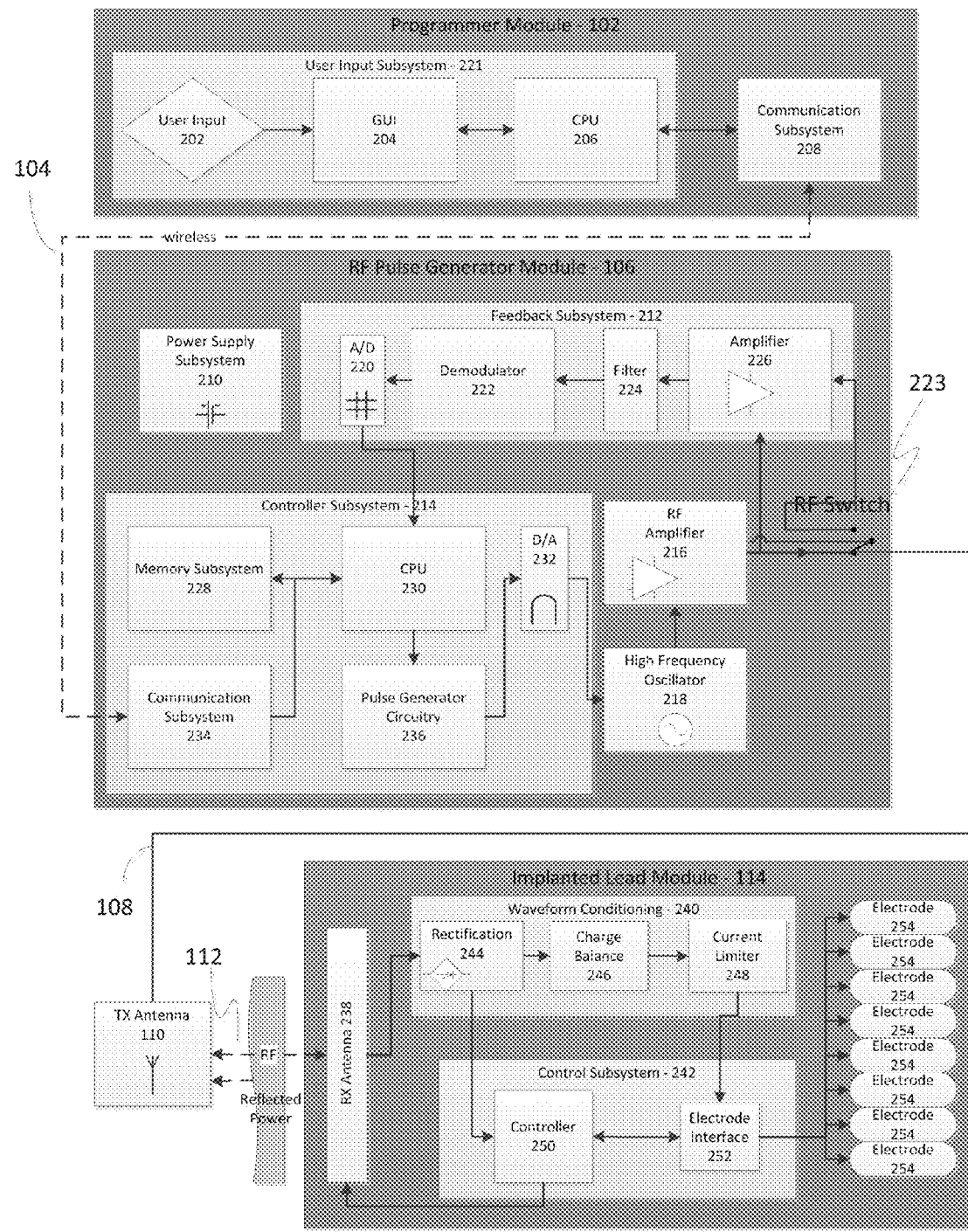
FIG. 2 depicts a detailed diagram of an example of the wireless stimulation device.

FIG. 2 depicts a detailed diagram of an example of the wireless stimulation device. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 20 mA |
| Pulse Frequency: | 0 to 10000 Hz |
| Pulse Width: | 0 to 2 ms |

The implantable wireless stimulation device 114 or RF pulse generator module 114 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulation device 114 may include both power and parameter-setting attributes in regards to stimulus waveform, amplitude, pulse width, and frequency. The RF pulse generator module 106 can also function as a wireless receiving unit that receives feedback signals from the implanted wireless stimulation device 114. To that end, the RF pulse generator module 106 may contain microelectronics or other circuitry to handle the generation of the signals transmitted to the device 114 as well as handle feedback signals, such as those from the device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receive (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 700 MHz to 8 GHz. The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulation device module 114 to send instructions about the various operations of the wireless stimulation device module 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same lead to power the wireless stimulation device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulation device 114), the RF switch 223 is set to send the forward power signal to feedback subsystem. During the off-cycle time (when an RF signal is not being transmitted to the wireless stimulation device module 114), the RF switch 223 can change to a receiving mode in which the reflected RF energy and/or RF signals from the wireless stimulation device module 114 are received to be analyzed in the feedback subsystem 212.

The feedback subsystem 212 of the RF pulse generator module 106 may include reception circuitry to receive and extract telemetry or other feedback signals from the wireless stimulation device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulation device 114 may transmit informational signals, such as a telemetry signal, through the antenna 238 to communicate with the RF pulse generator module 106 during its receive cycle. For example, the telemetry signal from the wireless stimulation device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse modulated signal from the internal antenna(s) 238 of the wireless stimulation device 114.

A telemetry signal from the implanted wireless stimulation device module 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulation device 114, and sent on the telemetry signal. The frequency of the carrier signal may be in the range of at 700 MHz to 8 GHz.

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulation device 114 delivered the specified stimuli to tissue. For example, if the wireless stimulation device reports a lower current than was specified, the power level from the RF pulse generator module 106 can be increased so that the implanted wireless stimulation device 114 will have more available power for stimulation. The implanted wireless stimulation device 114 can generate telemetry data in real time, for example, at a rate of 8 kbits per second. All feedback data received from the implanted lead module 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulation device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulation device module 114 to be converted into electrical pulses applied to the electrodes 254 through electrode interface 252. In some implementations, the implanted wireless stimulation device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulation device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulation device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulation device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulation device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulation device module 114 may create a drive-waveform envelope that follows the envelope of the RF pulse received by the receiving dipole antenna(s) 238. In this case, the RF pulse generator module 106 can directly control the envelope of the drive waveform within the wireless stimulation device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulation device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulation device 114, such as controller 250. In the case of onboard control, the amplitude and timing may be specified or modified by data commands delivered from the pulse generator module 106.

Figure 3:
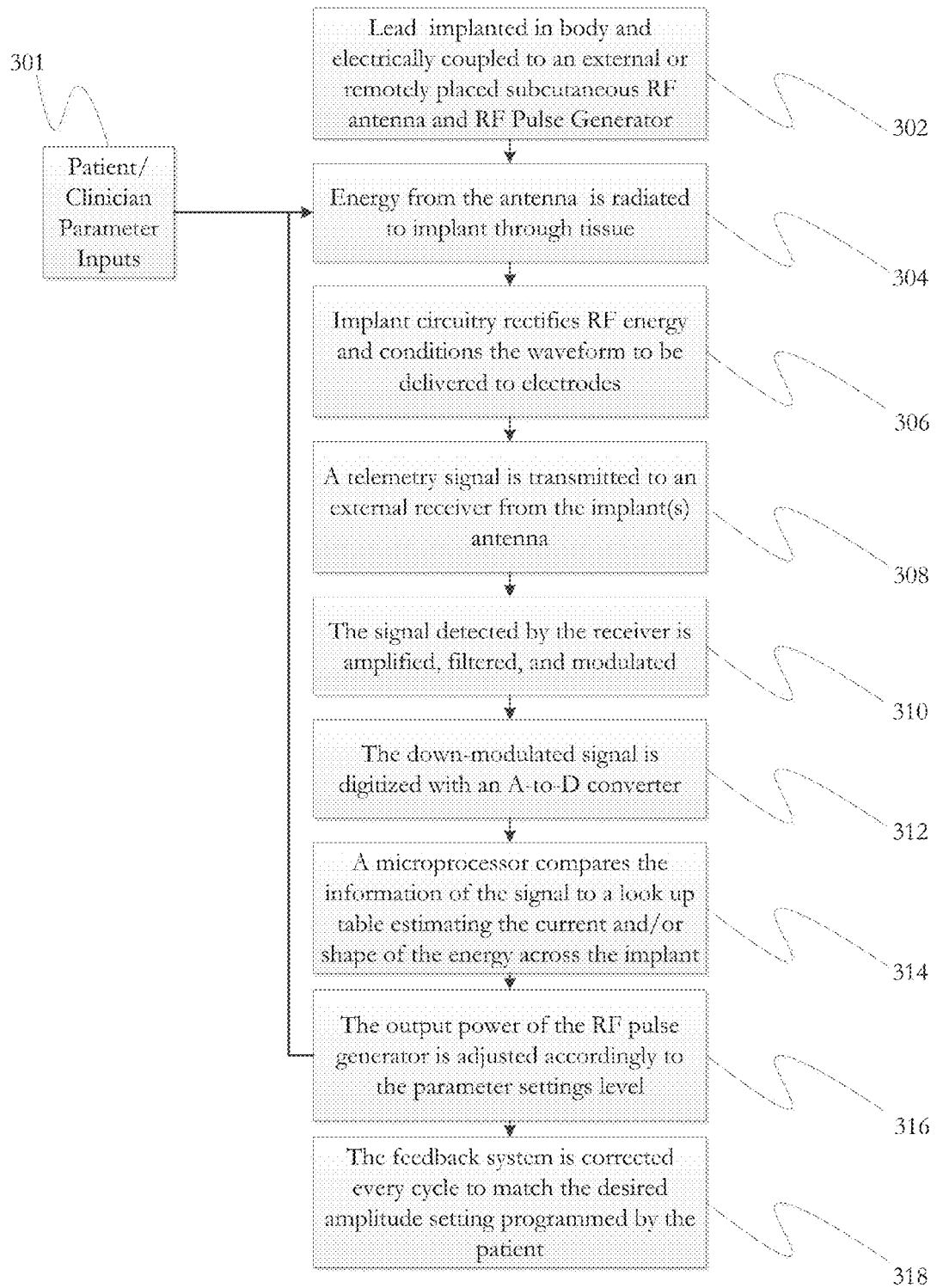
FIG. 3 is a flowchart showing an example of the operation of the wireless stimulation device.

FIG. 3 is a flowchart showing an example of an operation of the neural stimulator system. In block 302, the wireless stimulation device 114 is implanted in proximity to nerve bundles and is coupled to the electric field produced by the TX antenna 110. That is, the pulse generator module 106 and the TX antenna 110 are positioned in such a way (for example, in proximity to the patient) that the TX antenna 110 is electrically radiatively coupled with the implanted RX antenna 238 of the wireless stimulation device 114. In certain implementations, both the antenna 110 and the RF pulse generator 106 are located subcutaneously. In other implementations, the antenna 110 and the RF pulse generator 106 are located external to the patient's body. In this case, the TX antenna 110 may be coupled directly to the patient's skin.

Energy from the RF pulse generator is radiated to the implanted wireless stimulation device 114 from the antenna 110 through tissue, as shown in block 304. The energy radiated may be controlled by the Patient/Clinician Parameter inputs in block 301. In some instances, the parameter settings can be adjusted in an open loop fashion by the patient or clinician, who would adjust the parameter inputs in block 301 to the system.

The implanted wireless stimulation device 114 uses the received energy to generate electrical pulses to be applied to the neural tissue through the electrodes 238. For instance, the wireless stimulation device 114 may contain circuitry that rectifies the received RF energy and conditions the waveform to charge balance the energy delivered to the electrodes to stimulate the targeted nerves or tissues, as shown in block 306. The implanted wireless stimulation device 114 communicates with the pulse generator 106 by using antenna 238 to send a telemetry signal, as shown in block 308. The telemetry signal may contain information about parameters of the electrical pulses applied to the electrodes, such as the impedance of the electrodes, whether the safe current limit has been reached, or the amplitude of the current that is presented to the tissue from the electrodes.

In block 310, the RF pulse generator 106 detects amplifies, filters and modulates the received telemetry signal using amplifier 226, filter 224, and demodulator 222, respectively. The A/D converter 230 then digitizes the resulting analog signal, as shown in 312. The digital telemetry signal is routed to CPU 230, which determines whether the parameters of the signal sent to the wireless stimulation device 114 need to be adjusted based on the digital telemetry signal. For instance, in block 314, the CPU 230 compares the information of the digital signal to a look-up table, which may indicate an appropriate change in stimulation parameters. The indicated change may be, for example, a change in the current level of the pulses applied to the electrodes. As a result, the CPU may change the output power of the signal sent to wireless stimulation device 114 so as to adjust the current applied by the electrodes 254, as shown in block 316.

Thus, for instance, the CPU 230 may adjust parameters of the signal sent to the wireless stimulation device 114 every cycle to match the desired current amplitude setting programmed by the patient, as shown in block 318. The status of the stimulator system may be sampled in real time at a rate of 8 kbits per second of telemetry data. All feedback data received from the wireless stimulation device 114 can be maintained against time and sampled per minute to be stored for download or upload to a remote monitoring system accessible by the health care professional for trending and statistical correlations in block 318. If operated in an open loop fashion, the stimulator system operation may be reduced to just the functional elements shown in blocks 302, 304, 306, and 308, and the patient uses their judgment to adjust parameter settings rather than the closed looped feedback from the implanted device.

Figure 4:
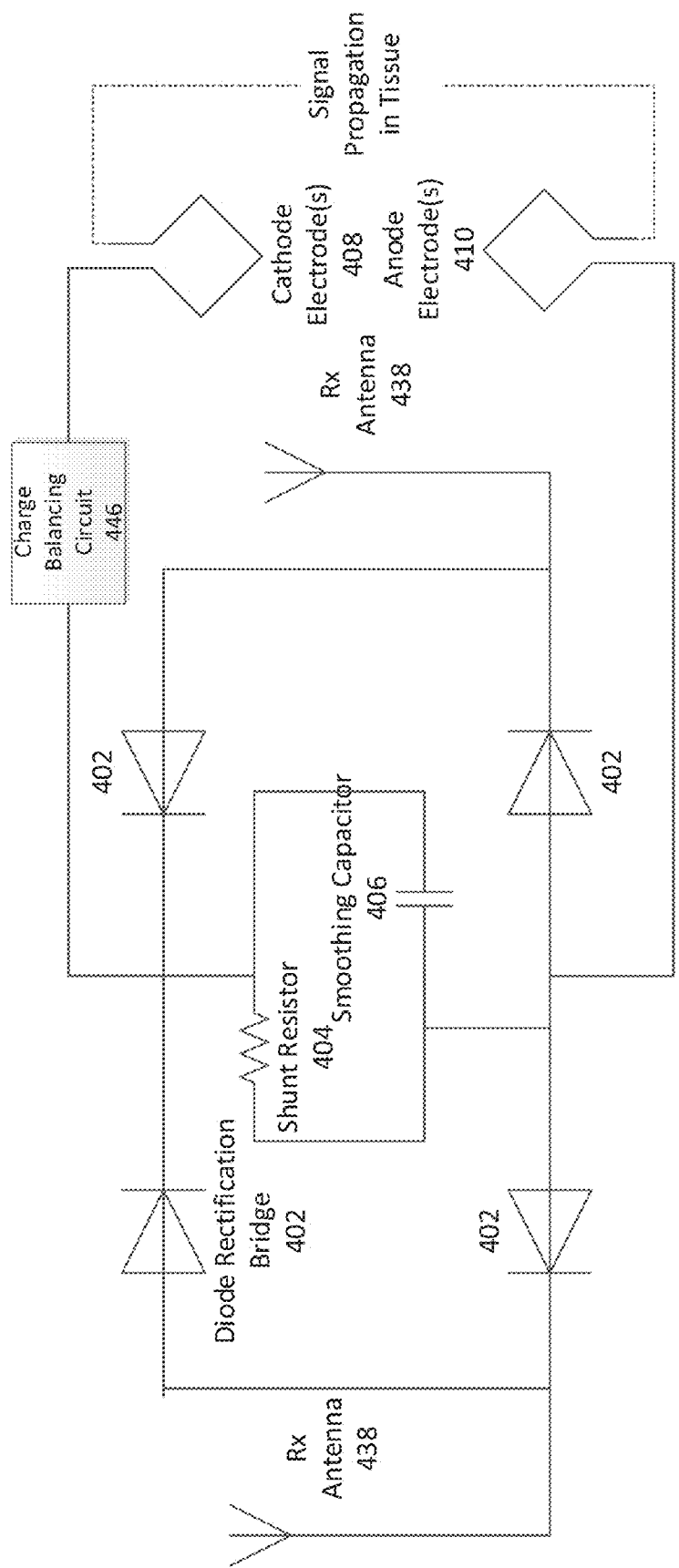
FIG. 4 is a circuit diagram showing an example of a wireless stimulation device.

FIG. 4 is a circuit diagram showing an example of a wireless neural stimulator, such as wireless stimulation device 114. This example contains paired electrodes, comprising cathode electrode(s) 408 and anode electrode(s) 410, as shown. When energized, the charged electrodes create a volume conduction field of current density within the tissue. In this implementation, the wireless energy is received through a dipole antenna(s) 238. At least four diodes are connected together to form a full wave bridge rectifier 402 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 includes two branches of diode pairs connecting an anode-to-anode and then cathode to cathode. The electrodes 408 and 410 are connected to the output of the charge balancing circuit 246.

Figure 5:
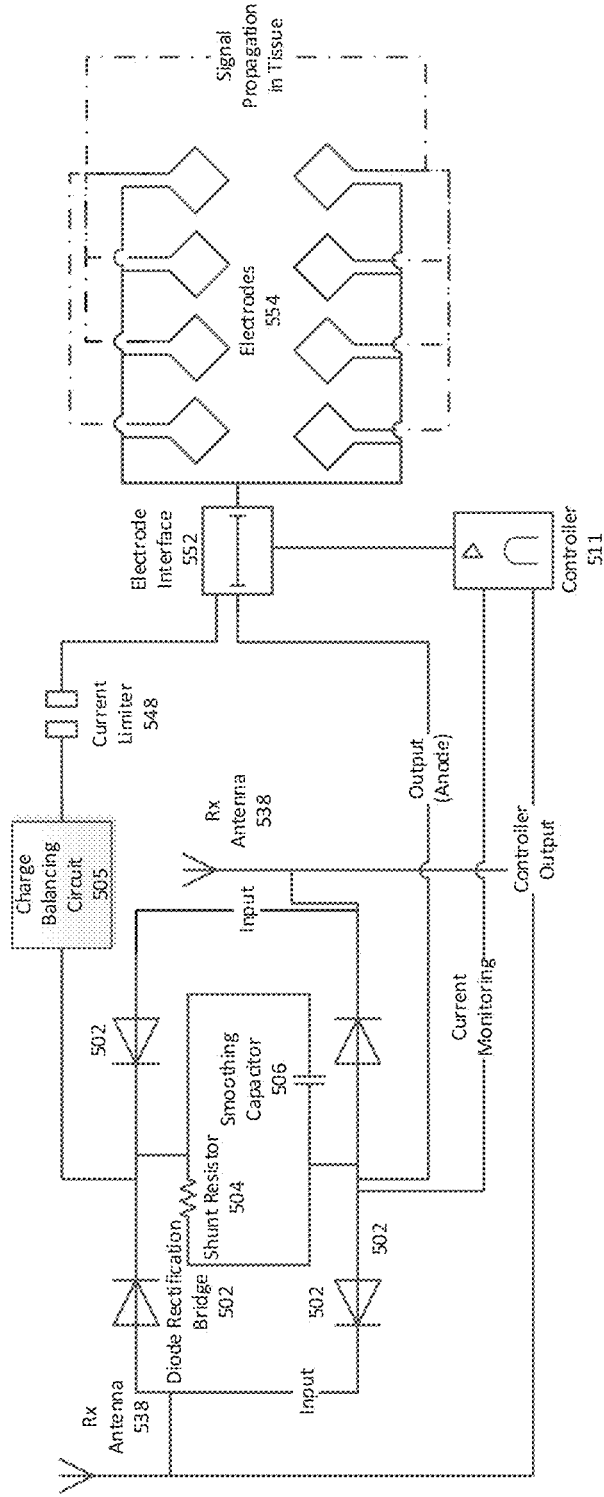
FIG. 5 is a circuit diagram of another example of a wireless stimulation device.

FIG. 5 is a circuit diagram of another example of a wireless stimulation device 114. The example shown in FIG. 5 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 may include two branches of diode pairs connecting an anode-to-anode and then cathode to cathode. The electrode polarity outputs, both cathode 408 and anode 410 are connected to the outputs formed by the bridge connection. Charge balancing circuitry 246 and current limiting circuitry 248 are placed in series with the outputs.

Figure 6:
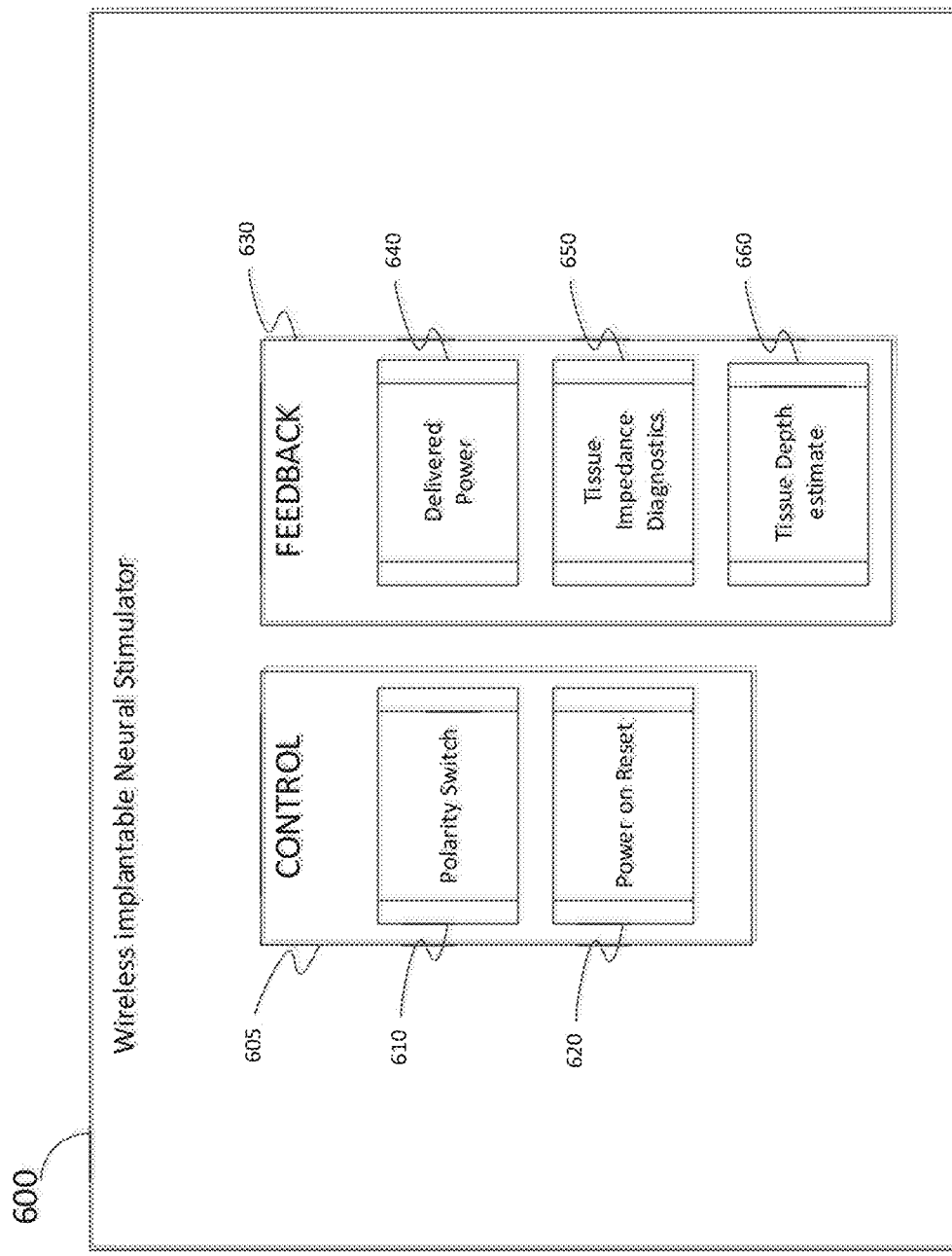
FIG. 6 is a block diagram showing an example of control and feedback functions of a wireless stimulation device.

FIG. 6 is a block diagram showing an example of control functions 605 and feedback functions 630 of a implantable wireless stimulation device 600, such as the ones described above or further below. An example implementation may be a wireless stimulation device module 114, as discussed above in association with FIG. 2. Control functions 605 include functions 610 for polarity switching of the electrodes and functions 620 for power-on reset.

Polarity switching functions 610 may employ, for example, a polarity routing switch network to assign polarities to electrodes 254. The assignment of polarity to an electrode may, for instance, be one of: a cathode (negative polarity), an anode (positive polarity), or a neutral (off) polarity. The polarity assignment information for each of the electrodes 254 may be contained in the input signal received by implantable wireless stimulation device 600 through Rx antenna 238 from RF pulse generator module 106. Because a programmer module 102 may control RF pulse generator module 106, the polarity of electrodes 254 may be controlled remotely by a programmer through programmer module 102, as shown in FIG. 2.

Power-on reset functions 620 may reset the polarity assignment of each electrode immediately on each power-on event. As will be described in further detail below, this reset operation may cause RF pulse generator module 106 to transmit the polarity assignment information to the implantable wireless stimulation device 600. Once the polarity assignment information is received by the implantable wireless stimulation device 600, the polarity assignment information may be stored in a register file, or other short term memory component. Thereafter the polarity assignment information may be used to configure the polarity assignment of each electrode. If the polarity assignment information transmitted in response to the reset encodes the same polarity state as before the power-on event, then the polarity state of each electrode can be maintained before and after each power-on event.

Feedback functions 630 include functions 640 for monitoring delivered power to electrodes 254 and functions 650 for making impedance diagnosis of electrodes 254. For example, delivered power functions 640 may provide data encoding the amount of power being delivered from electrodes 254 to the excitable tissue and tissue impedance diagnostic functions 650 may provide data encoding the diagnostic information of tissue impedance. The tissue impedance is the electrical impedance of the tissue as seen between negative and positive electrodes when a stimulation current is being released between negative and positive electrodes.

Feedback functions 630 may additionally include tissue depth estimate functions 660 to provide data indicating the overall tissue depth that the input radio frequency (RF) signal from the pulse generator module, such as, for example, RF pulse generator module 106, has penetrated before reaching the implanted antenna, such as, for example, RX antenna 238, within the wireless implantable neural stimulator 600, such as, for example, implanted wireless stimulation device 114. For instance, the tissue depth estimate may be provided by comparing the power of the received input signal to the power of the RF pulse transmitted by the RF pulse generator 106. The ratio of the power of the received input signal to the power of the RF pulse transmitted by the RF pulse generator 106 may indicate an attenuation caused by wave propagation through the tissue. For example, the second harmonic described below may be received by the RF pulse generator 106 and used with the power of the input signal sent by the RF pulse generator to determine the tissue depth. The attenuation may be used to infer the overall depth of implantable wireless stimulation device 600 underneath the skin.

The data from blocks 640, 650, and 660 may be transmitted, for example, through Tx antenna 110 to RF pulse generator 106, as illustrated in FIGS. 1 and 2.

As discussed above in association with FIGS. 1, 2, 4, and 5, a implantable wireless stimulation device 600 may utilize rectification circuitry to convert the input signal (e.g., having a carrier frequency within a range from about 800 MHz to about 8 GHz) to a direct current (DC) power to drive the electrodes 254. Some implementations may provide the capability to regulate the DC power remotely. Some implementations may further provide different amounts of power to different electrodes, as discussed in further detail below.

Figure 7:
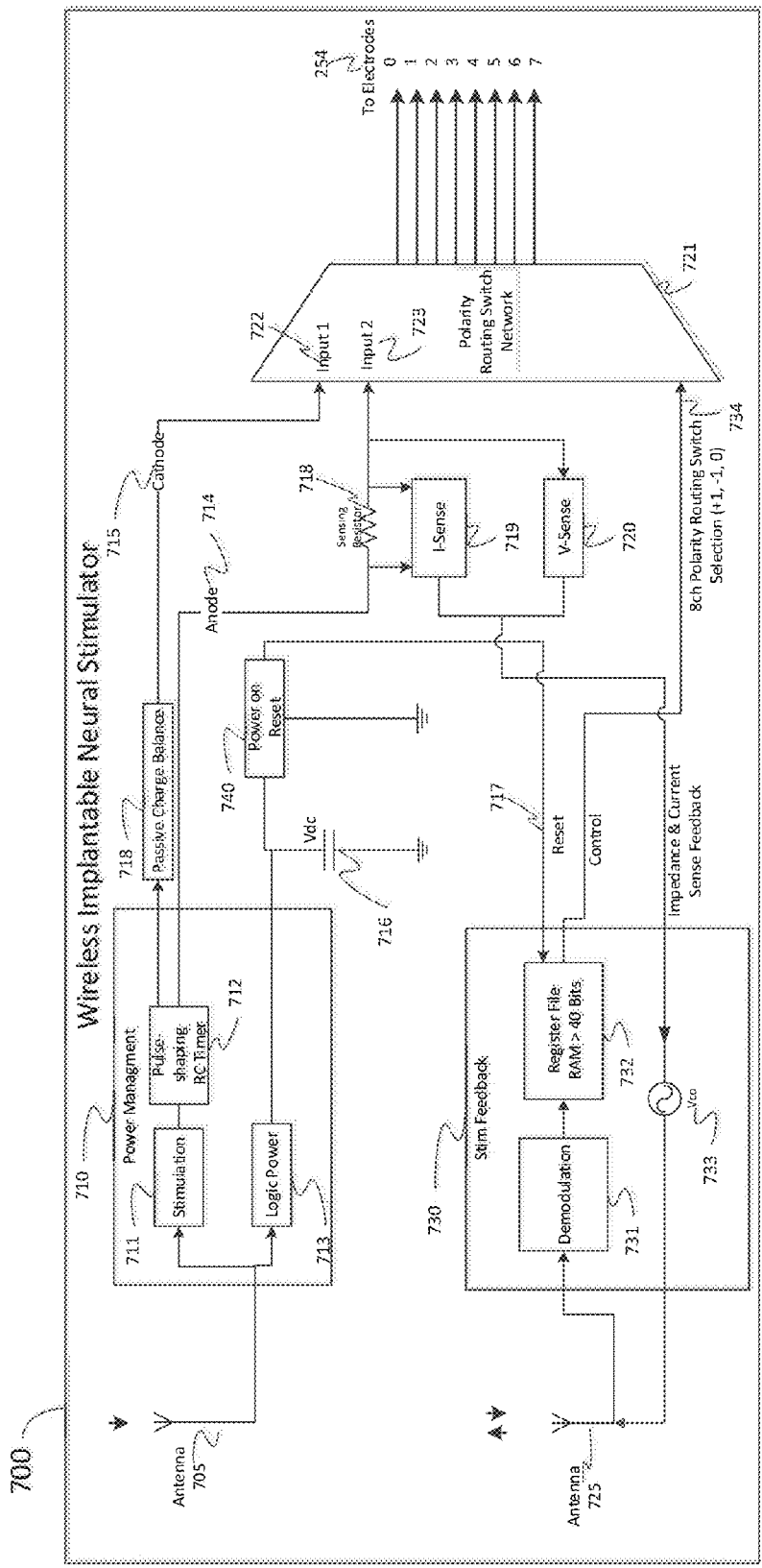
FIG. 7 is a schematic showing an example of a wireless stimulation device with components to implement control and feedback functions.

FIG. 7 is a schematic showing an example of a implantable wireless stimulation device 700 with components to implement control and feedback functions as discussed above in association with FIG. 6. An RX antenna 705 receives the input signal. The RX antenna 705 may be embedded as a dipole, microstrip, folded dipole or other antenna configuration other than a coiled configuration, as described above. The input signal has a carrier frequency in the GHz range and contains electrical energy for powering the wireless implantable neural stimulator 700 and for providing stimulation pulses to electrodes 254. Once received by the antenna 705, the input signal is routed to power management circuitry 710. Power management circuitry 710 is configured to rectify the input signal and convert it to a DC power source. For example, the power management circuitry 710 may include a diode rectification bridge such as the diode rectification bridge 402 illustrated in FIG. 4. The DC power source provides power to stimulation circuitry 711 and logic power circuitry 713. The rectification may utilize one or more full wave diode bridge rectifiers within the power management circuitry 710. In one implementation, a resistor can be placed across the output nodes of the bridge rectifier to discharge the electrodes to the ground of the bridge anode, as illustrated by the shunt register 404 in FIG. 7.

Figure 8:
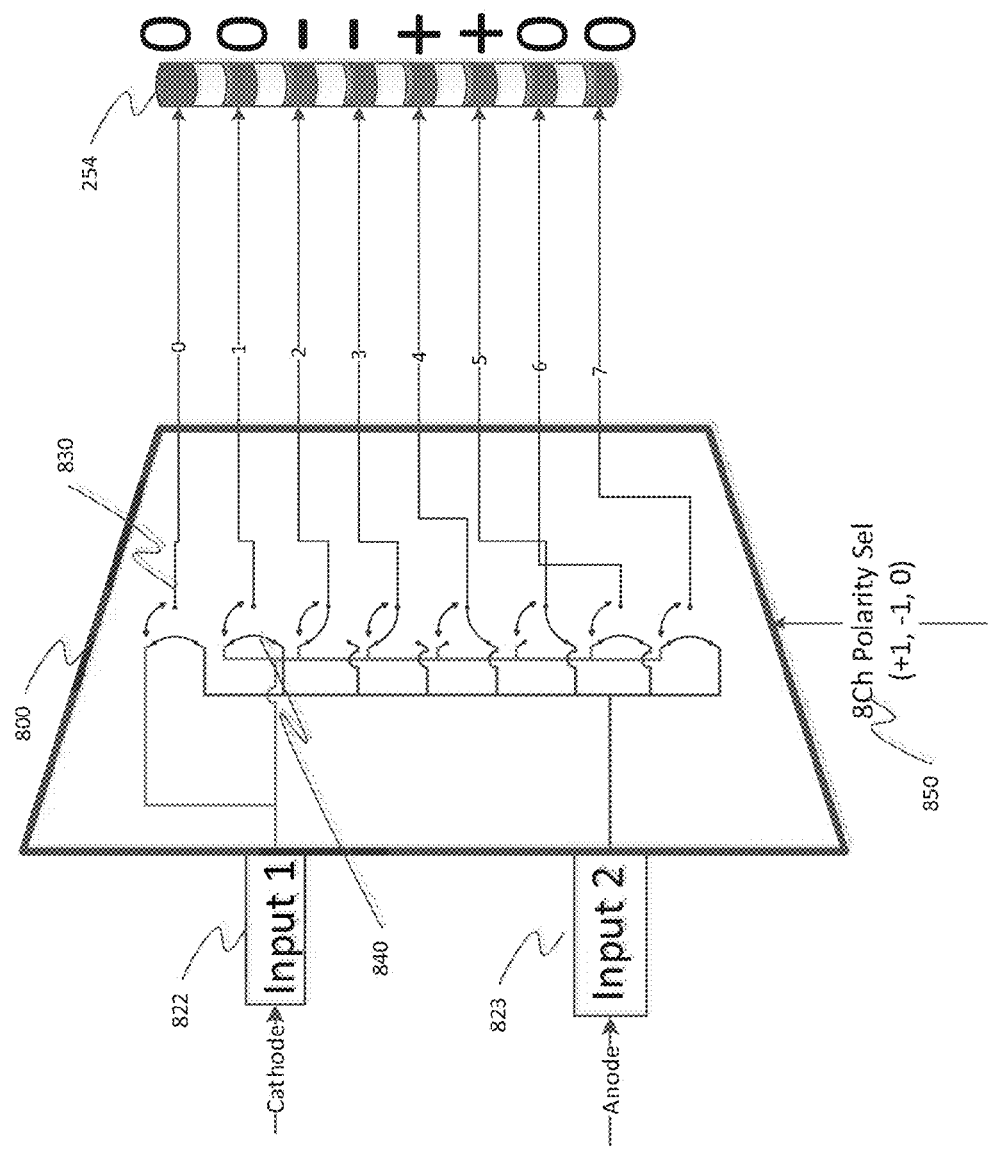
FIG. 8 is a schematic of an example of a polarity routing switch network.

Turning momentarily to FIG. 8, a schematic of an example of a polarity routing switch network 800 is shown. As discussed above, the cathodic (−) energy and the anodic energy are received at input 1 (block 722) and input 2 (block 723), respectively. Polarity routing switch network 800 has one of its outputs coupled to an electrode of electrodes 254 which can include as few as two electrodes, or as many as sixteen electrodes. Eight electrodes are shown in this implementation as an example.

Polarity routing switch network 800 is configured to either individually connect each output to one of input 1 or input 2, or disconnect the output from either of the inputs. This selects the polarity for each individual electrode of electrodes 254 as one of: neutral (off), cathode (negative), or anode (positive). Each output is coupled to a corresponding three-state switch 830 for setting the connection state of the output. Each three-state switch is controlled by one or more of the bits from the selection input 850. In some implementations, selection input 850 may allocate more than one bits to each three-state switch. For example, two bits may encode the three-state information. Thus, the state of each output of polarity routing switch device 800 can be controlled by information encoding the bits stored in the register 732, which may be set by polarity assignment information received from the remote RF pulse generator module 106, as described further below.

Returning to FIG. 7, power and impedance sensing circuitry may be used to determine the power delivered to the tissue and the impedance of the tissue. For example, a sensing resistor 718 may be placed in serial connection with the anodic branch 714. Current sensing circuit 719 senses the current across the resistor 718 and voltage sensing circuit 720 senses the voltage across the resistor. The measured current and voltage may correspond to the actual current and voltage applied by the electrodes to the tissue.

As described below, the measured current and voltage may be provided as feedback information to RF pulse generator module 106. The power delivered to the tissue may be determined by integrating the product of the measured current and voltage over the duration of the waveform being delivered to electrodes 254. Similarly, the impedance of the tissue may be determined based on the measured voltage being applied to the electrodes and the current being applied to the tissue. Alternative circuitry (not shown) may also be used in lieu of the sensing resistor 718, depending on implementation of the feature and whether both impedance and power feedback are measured individually, or combined.

The measurements from the current sensing circuitry 719 and the voltage sensing circuitry 720 may be routed to a voltage controlled oscillator (VCO) 733 or equivalent circuitry capable of converting from an analog signal source to a carrier signal for modulation. VCO 733 can generate a digital signal with a carrier frequency. The carrier frequency may vary based on analog measurements such as, for example, a voltage, a differential of a voltage and a power, etc. VCO 733 may also use amplitude modulation or phase shift keying to modulate the feedback information at the carrier frequency. The VCO or the equivalent circuit may be generally referred to as an analog controlled carrier modulator. The modulator may transmit information encoding the sensed current or voltage back to RF pulse generator 106.

Antenna 725 may transmit the modulated signal, for example, in the GHz frequency range, back to the RF pulse generator module 106. In some embodiments, antennas 705 and 725 may be the same physical antenna. In other embodiments, antennas 705 and 725 may be separate physical antennas. In the embodiments of separate antennas, antenna 725 may operate at a resonance frequency that is higher than the resonance frequency of antenna 705 to send stimulation feedback to RF pulse generator module 106. In some embodiments. antenna 725 may also operate at the higher resonance frequency to receive data encoding the polarity assignment information from RF pulse generator module 106.

Antenna 725 may be a telemetry antenna 725 which may route received data, such as polarity assignment information, to the stimulation feedback circuit 730. The encoded polarity assignment information may be on a band in the GHz range. The received data may be demodulated by demodulation circuitry 731 and then stored in the register file 732. The register file 732 may be a volatile memory. Register file 732 may be an 8-channel memory bank that can store, for example, several bits of data for each channel to be assigned a polarity. Some embodiments may have no register file, while some embodiments may have a register file up to 64 bits in size. The information encoded by these bits may be sent as the polarity selection signal to polarity routing switch network 721, as indicated by arrow 734. The bits may encode the polarity assignment for each output of the polarity routing switch network as one of: + (positive), − (negative), or 0 (neutral). Each output connects to one electrode and the channel setting determines whether the electrode will be set as an anode (positive), cathode (negative), or off (neutral).

Returning to power management circuitry 710, in some embodiments, approximately 90% of the energy received is routed to the stimulation circuitry 711 and less than 10% of the energy received is routed to the logic power circuitry 713. Logic power circuitry 713 may power the control components for polarity and telemetry. In some implementations, the power circuitry 713, however, does not provide the actual power to the electrodes for stimulating the tissues. In certain embodiments, the energy leaving the logic power circuitry 713 is sent to a capacitor circuit 716 to store a certain amount of readily available energy. The voltage of the stored charge in the capacitor circuit 716 may be denoted as Vdc. Subsequently, this stored energy is used to power a power-on reset circuit 716 configured to send a reset signal on a power-on event. If the wireless implantable neural stimulator 700 loses power for a certain period of time, for example, in the range from about 1 millisecond to over 10 milliseconds, the contents in the register file 732 and polarity setting on polarity routing switch network 721 may be zeroed. The implantable wireless stimulation device 700 may lose power, for example, when it becomes less aligned with RF pulse generator module 106. Using this stored energy, power-on reset circuit 740 may provide a reset signal as indicated by arrow 717. This reset signal may cause stimulation feedback circuit 730 to notify RF pulse generator module 106 of the loss of power. For example, stimulation feedback circuit 730 may transmit a telemetry feedback signal to RF pulse generator module 106 as a status notification of the power outage. This telemetry feedback signal may be transmitted in response to the reset signal and immediately after power is back on wireless stimulation device 700. RF pulse generator module 106 may then transmit one or more telemetry packets to implantable wireless stimulation device. The telemetry packets contain polarity assignment information, which may be saved to register file 732 and may be sent to polarity routing switch network 721. Thus, polarity assignment information in register file 732 may be recovered from telemetry packets transmitted by RF pulse generator module 106 and the polarity assignment for each output of polarity routing switch network 721 may be updated accordingly based on the polarity assignment information.

The telemetry antenna 725 may transmit the telemetry feedback signal back to RF pulse generator module 106 at a frequency higher than the characteristic frequency of an RX antenna 705. In one implementation, the telemetry antenna 725 can have a heightened resonance frequency that is the second harmonic of the characteristic frequency of RX antenna 705. For example, the second harmonic may be utilized to transmit power feedback information regarding an estimate of the amount of power being received by the electrodes. The feedback information may then be used by the RF pulse generator in determining any adjustment of the power level to be transmitted by the RF pulse generator 106. In a similar manner, the second harmonic energy can be used to detect the tissue depth. The second harmonic transmission can be detected by an external antenna, for example, on RF pulse generator module 106 that is tuned to the second harmonic. As a general matter, power management circuitry 710 may contain rectifying circuits that are non-linear device capable of generating harmonic energies from input signal. Harvesting such harmonic energy for transmitting telemetry feedback signal could improve the efficiency of implantable wireless stimulation device 700.

Figure 9A:
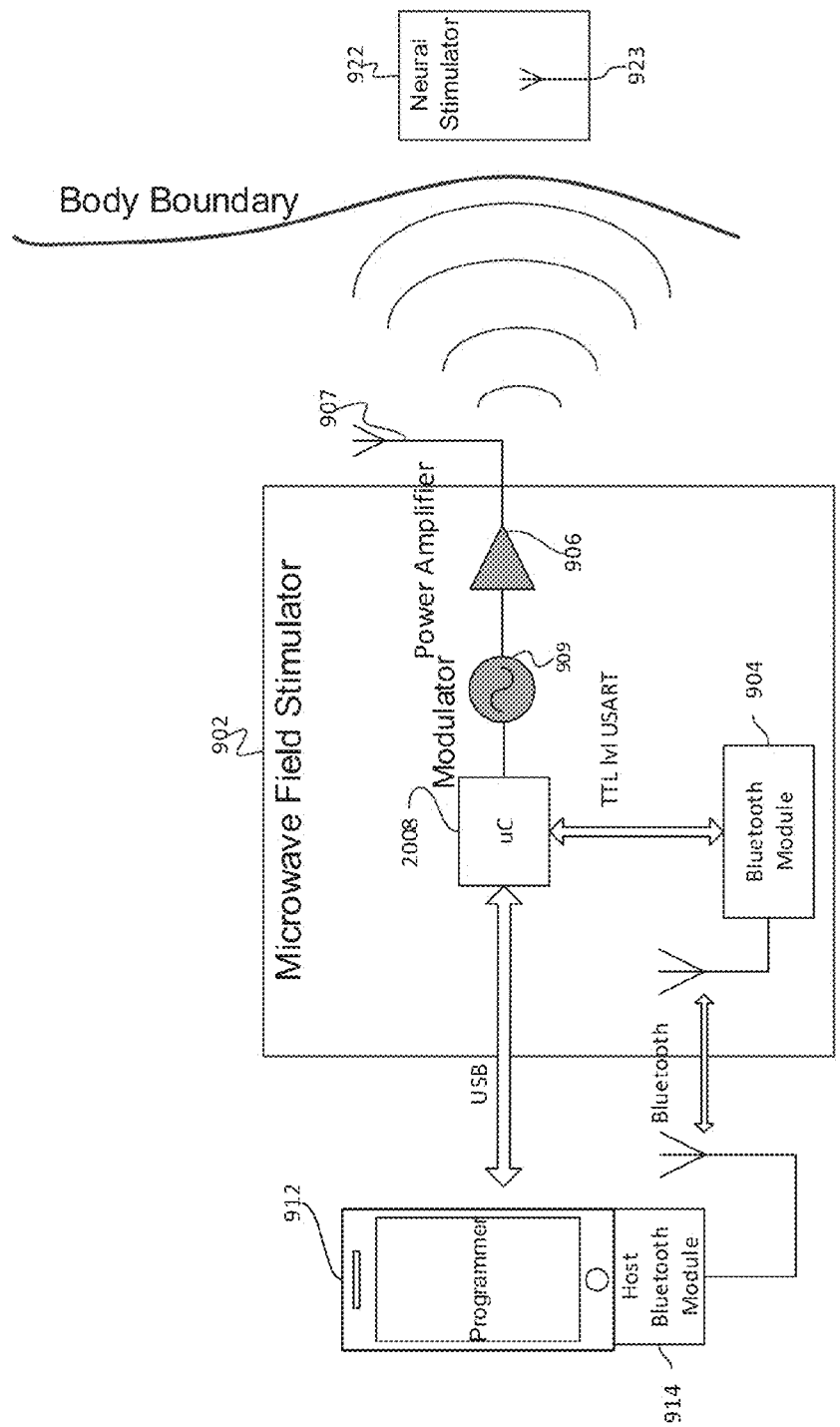
FIG. 9A is a diagram of an example microwave field stimulator (MFS) operating along with a wireless stimulation device.

FIG. 9A is a diagram of an example implementation of a microwave field stimulator (MFS) 902 as part of a stimulation system utilizing an implantable wireless stimulation device 922. In this example, the MFS 902 is external to a patient's body and may be placed within in close proximity, for example, within 3 feet, to an implantable wireless stimulation device 922. The RF pulse generator module 106 may be one example implementation of MFS 902. MFS 902 may be generally known as a controller module. The implantable wireless stimulation device 922 is a passive device. The implantable wireless stimulation device 922 does not have its own independent power source, rather it receives power for its operation from transmission signals emitted from a TX antenna powered by the MFS 902, as discussed above.

In certain embodiments, the MFS 902 may communicate with a programmer 912. The programmer 912 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 904 which communicates with the host bluetooth module 914 within the programmer 912.

The MFS 902 may additionally communicate with wireless stimulation device 922 by transmitting a transmission signal through a Tx antenna 907 coupled to an amplifier 906. The transmission signal may propagate through skin and underlying tissues to arrive at the Rx antenna 923 of the wireless stimulation device 922. In some implementations, the wireless stimulation device 922 may transmit a telemetry feedback signal back to microwave field stimulator 902.

The microwave field stimulator 902 may include a microcontroller 908 configured to manage the communication with a programmer 912 and generate an output signal. The output signal may be used by the modulator 909 to modulate a RF carrier signal. The frequency of the carrier signal may be in the microwave range, for example, from about 700 MHz to about 8 GHz, preferably from about 800 MHz to 1.2 GHz. The modulated RF carrier signal may be amplified by an amplifier 906 to provide the transmission signal for transmission to the wireless stimulation device 922 through a TX antenna 907.

Figure 9B:
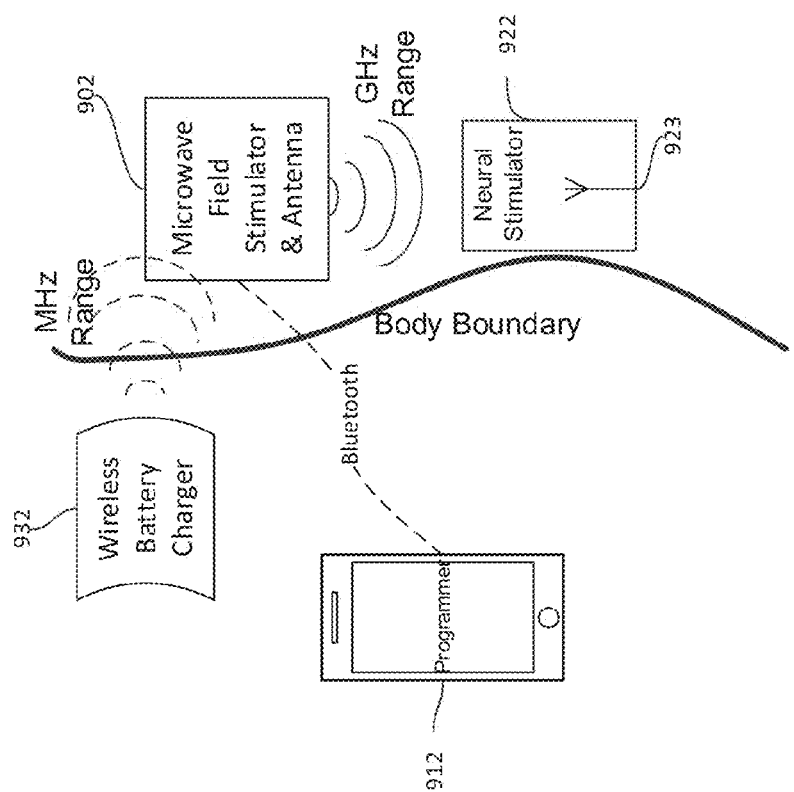
FIG. 9B is a diagram of another example MFS operating along with a wireless stimulation device.

FIG. 9B is a diagram of another example of an implementation of a microwave field stimulator 902 as part of a stimulation system utilizing a wireless stimulation device 922. In this example, the microwave field stimulator 902 may be embedded in the body of the patient, for example, subcutaneously. The embedded microwave field stimulator 902 may receive power from a detached, remote wireless battery charger 932.

The power from the wireless battery charger 932 to the embedded microwave field stimulator 902 may be transmitted at a frequency in the MHz or GHz range. The microwave field stimulator 902 shall be embedded subcutaneously at a very shallow depth (e.g., less than 1 cm), and alternative coupling methods may be used to transfer energy from wireless battery charger 932 to the embedded MFS 902 in the most efficient manner as is well known in the art.

In some embodiments, the microwave field stimulator 902 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the microwave field stimulator 902 shall transmit power and parameter signals to a passive Tx antenna also embedded subcutaneously, which shall be coupled to the RX antenna within the wireless stimulation device 922. The power required in this embodiment is substantially lower since the TX antenna and the RX antenna are already in body tissue and there is no requirement to transmit the signal through the skin.

Figure 10:
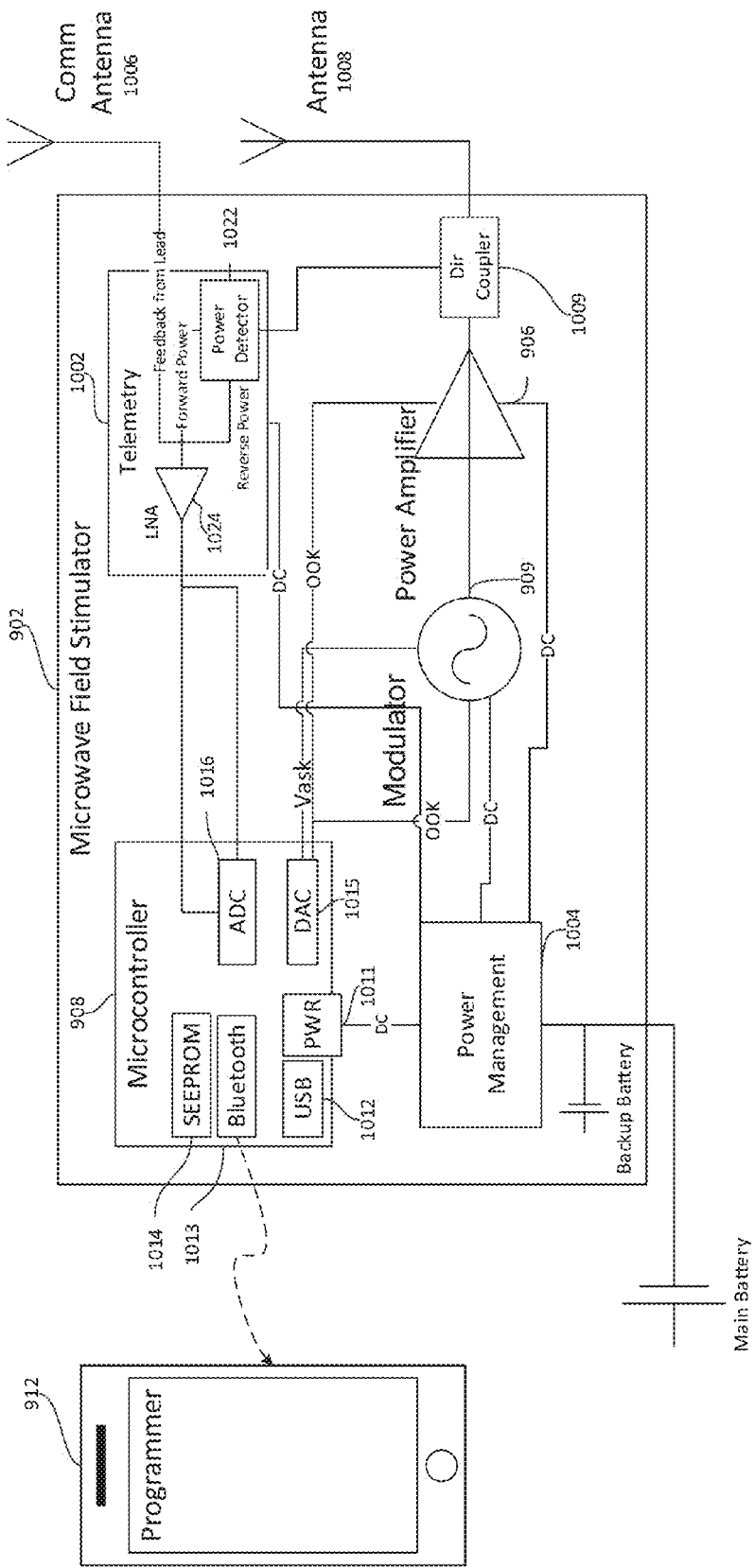
FIG. 10 is a detailed diagram of an example MFS.

FIG. 10 is a detailed diagram of an example microwave field stimulator 902. A microwave field stimulator 902 may include a microcontroller 908, a telemetry feedback module 1002, and a power management module 1004. The microwave field stimulator 902 has a two-way communication schema with a programmer 912, as well as with a communication or telemetry antenna 1006. The microwave field stimulator 902 sends output power and data signals through a TX antenna 1008.

The microcontroller 908 may include a storage device 1014, a bluetooth interface 1013, a USB interface 1012, a power interface 1011, an analog-to-digital converter (ADC) 1016, and a digital to analog converter (DAC) 1015. Implementations of a storage device 1014 may include non-volatile memory, such as, for example, static electrically erasable programmable read-only memory (SEEPROM) or NAND flash memory. A storage device 1014 may store waveform parameter information for the microcontroller 908 to synthesize the output signal used by modulator 909. The stimulation waveform may include multiple pulses. The waveform parameter information may include the shape, duration, amplitude of each pulse, as well as pulse repetition frequency. A storage device 1014 may additionally store polarity assignment information for each electrode of the wireless stimulation device 922. The Bluetooth interface 1013 and USB interface 1012 respectively interact with either the bluetooth module 1004 or the USB module to communicate with the programmer 912.

The communication antenna 1006 and a TX antenna 1008 may, for example, be configured in a variety of sizes and form factors, including, but not limited to a patch antenna, a slot antenna, or a dipole antenna. The TX antenna 1008 may be adapted to transmit a transmission signal, in addition to power, to the implantable, passive neural stimulator 922. As discussed above, an output signal generated by the microcontroller 908 may be used by the modulator 909 to provide the instructions for creation of a modulated RF carrier signal. The RF carrier signal may be amplified by amplifier 906 to generate the transmission signal. A directional coupler 1009 may be utilized to provide two-way coupling so that both the forward power of the transmission signal flow transmitted by the TX antenna 1008 and the reverse power of the reflected transmission may be picked up by power detector 1022 of telemetry feedback module 1002. In some implementations, a separate communication antenna 1006 may function as the receive antenna for receiving telemetry feedback signal from the wireless stimulation device 922. In some configurations, the communication antenna may operate at a higher frequency band than the TX antenna 1008. For example, the communication antenna 1006 may have a characteristic frequency that is a second harmonic of the characteristic frequency of TX antenna 1008, as discussed above.

In some embodiments of this invention, the microwave field stimulator 902 may additionally include a telemetry feedback module 902. In some implementations, the telemetry feedback module 1002 may be coupled directly to communication antenna 1006 to receive telemetry feedback signals. The power detector 1022 may provide a reading of both the forward power of the transmission signal and a reverse power of a portion of the transmission signal that is reflected during transmission. The telemetry signal, forward power reading, and reverse power reading may be amplified by low noise amplifier (LNA) 1024 for further processing. For example, the telemetry module 902 may be configured to process the telemetry feedback signal by demodulating the telemetry feedback signal to extract the encoded information. Such encoded information may include, for example, a status of the wireless stimulation device 922 and one or more electrical parameters associated with a particular channel (electrode) of the wireless stimulation device 922. Based on the decoded information, the telemetry feedback module 1002 may be used to calculate a desired operational characteristic for the wireless stimulation device 922.

Some embodiments of the MFS 902 may further include a power management module 1004. A power management module 1004 may manage various power sources for the MFS 902. Example power sources include, but are not limited to, lithium-ion or lithium polymer batteries. The power management module 1004 may provide several operational modes to save battery power. Example operation modes may include, but are not limited to, a regular mode, a low power mode, a sleep mode, a deep sleep/hibernate mode, and an off mode. The regular mode provides regulation of the transmission of transmission signals and stimulus to the wireless stimulation device 922. In regular mode, the telemetry feedback signal is received and processed to monitor the stimuli as normal. Low-power mode also provides regulation of the transmission of transmission signals and stimulus to the electrodes of the wireless stimulation device. However, under this mode, the telemetry feedback signal may be ignored. More specifically, the telemetry feedback signal encoding the stimulus power may be ignored, thereby saving MFS 902 overall power consumption. Under sleep mode, the transceiver and amplifier 906 are turned off, while the microcontroller is kept on with the last saved state in its memory. Under the deep sleep/hibernate mode, the transceiver and amplifier 906 are turned off, while the microcontroller is in power down mode, but power regulators are on. Under the off mode, all transceiver, microcontroller and regulators are turned off achieving zero quiescent power.

Figure 11:
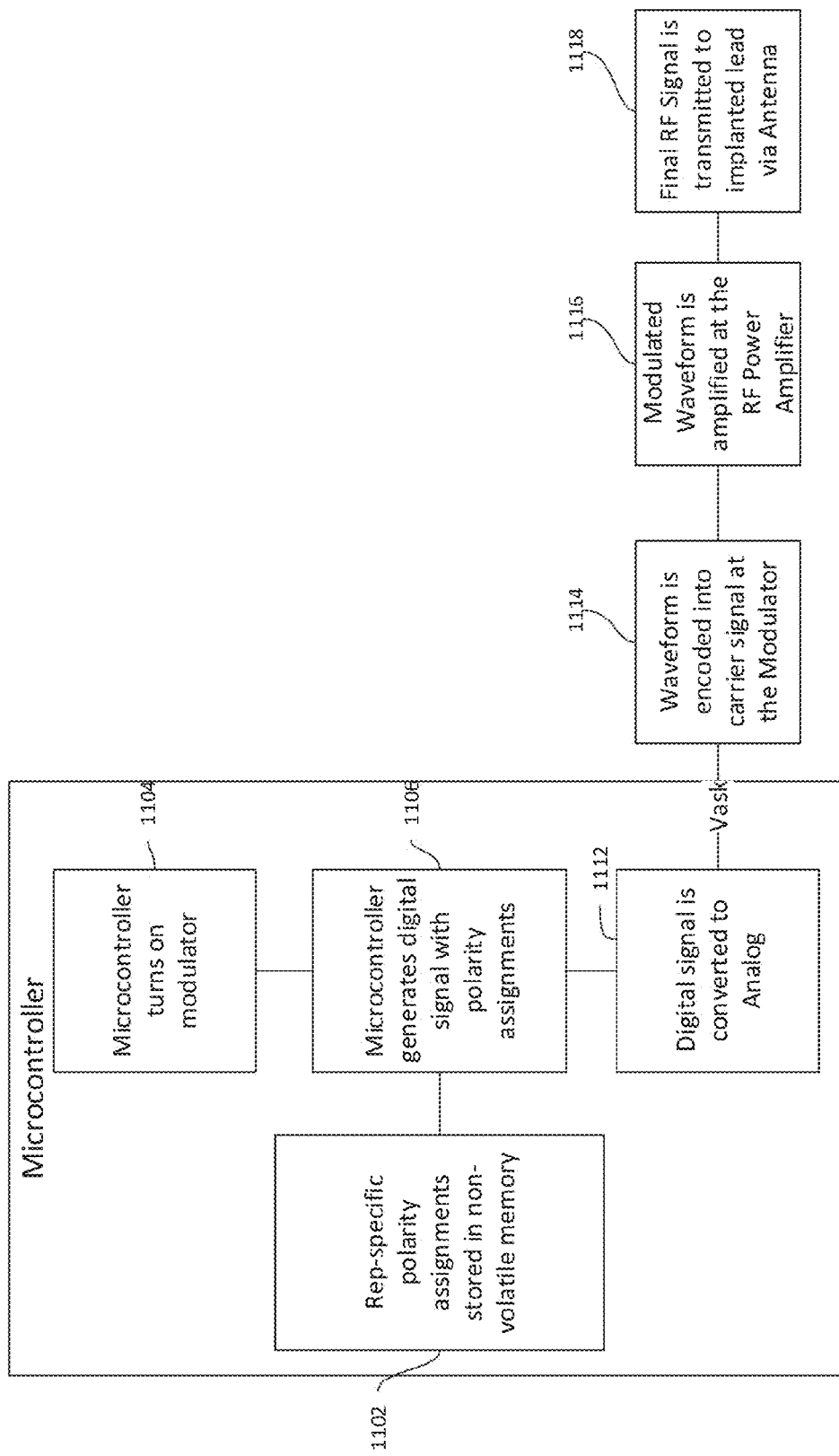
FIG. 11 is a flowchart showing an example process in which the MFS transmits polarity setting information to the wireless stimulation device.

FIG. 11 is a flowchart showing an example process in which the microwave field stimulator 902 transmits polarity setting information to the wireless stimulation device 922. Polarity assignment information is stored in a non-volatile memory 1102 within the microcontroller 908 of the MFS 902. The polarity assignment information may be representative-specific and may be chosen to meet the specific need of a particular patient. Based on the polarity assignment information chosen for a particular patient, the microcontroller 908 executes a specific routine for assigning polarity to each electrode of the electrode array. The particular patient has an wireless stimulation device as described above.

In some implementations, the polarity assignment procedure includes sending a signal to the wireless stimulation device with an initial power-on portion followed by a configuration portion that encodes the polarity assignments. The power-on portion may, for example, simply include the RF carrier signal. The initial power-on portion has a duration that is sufficient to power-on the wireless stimulation device and allow the device to reset into a configuration mode. Once in the configuration mode, the device reads the encoded information in the configuration portion and sets the polarity of the electrodes as indicated by the encoded information.

Thus, in some implementations, the microcontroller 908 turns on the modulator 909 so that the unmodulated RF carrier is sent to the wireless stimulation device 1104. After a set duration, the microcontroller 908 automatically initiates transmitting information encoding the polarity assignment. In this scenario, the microcontroller 908 transmits the polarity settings in the absence of handshake signals from the wireless stimulation device. Because the microwave field stimulator 902 is operating in close proximity to wireless stimulation device 922, signal degradation may not be severe enough to warrant the use of handshake signals to improve quality of communication.

To transmit the polarity information, the microcontroller 908 reads the polarity assignment information from the non-volatile memory and generates a digital signal encoding the polarity information 1106. The digital signal encoding the polarity information may be converted to an analog signal, for example, by a digital-to-analog (DAC) converter 1112. The analog signal encoding the waveform may modulate a carrier signal at modulator 909 to generate a configuration portion of the transmission signal (1114). This configuration portion of the transmission signal may be amplified by the power amplifier 906 to generate the signal to be transmitted by antenna 907 (1116). Thereafter, the configuration portion of the transmission signal is transmitted to the wireless stimulation device 922 (1118).

Once the configuration portion is transmitted to the wireless stimulation device, the microcontroller 908 initiates the stimulation portion of the transmission signal. Similar to the configuration portion, the microcontroller 908 generates a digital signal that encodes the stimulation waveform. The digital signal is converted to an analog signal using the DAC. The analog signal is then used to modulate a carrier signal at modulator 909 to generate a stimulation portion of the transmission signal.

In other implementations, the microcontroller 908 initiates the polarity assignment protocol after the microcontroller 908 has recognized a power-on reset signal transmitted by the neural stimulator. The power-on reset signal may be extracted from a feedback signal received by microcontroller 908 from the wireless stimulation device 922. The feedback signal may also be known as a handshake signal in that it alerts the microwave field stimulator 902 of the ready status of the wireless stimulation device 922. In an example, the feedback signal may be demodulated and sampled to digital domain before the power-on reset signal is extracted in the digital domain.

Figure 12:
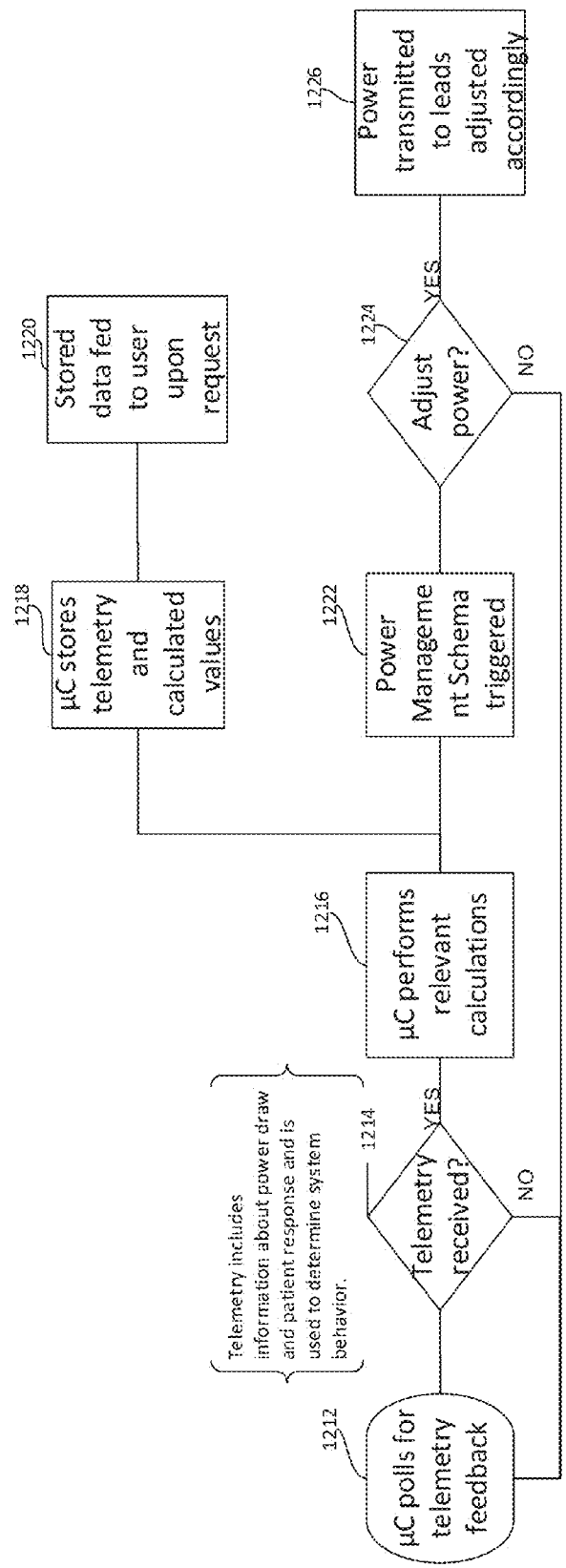
FIG. 12 is another flow chart showing an example process in which the MFS receives and processes the telemetry feedback signal to make adjustments to subsequent transmissions.

FIG. 12 is a flow chart showing an example of the process in which the microwave field stimulator 902 receives and processes the telemetry feedback signal to make adjustments to subsequent transmissions.

In some implementations, the microcontroller 908 polls the telemetry feedback module 1002 (1212). The polling is to determine whether a telemetry feedback signal has been received (1214). The telemetry feedback signal may include information based on which the MFS 902 may ascertain the power consumption being utilized by the electrodes of the wireless stimulation device 922. This information may also be used to determine the operational characteristics of the combination system of the MFS 902 and the wireless stimulation device 922, as will be discussed in further detail in association with FIG. 13. The information may also be logged by the microwave field stimulator 902 so that the response of the patient may be correlated with past treatments received over time. The correlation may reveal the patient's individual response to the treatments the patient has received up to date.

If the microcontroller 908 determines that telemetry feedback module 1002 has not yet received telemetry feedback signal, microcontroller 908 may continue polling (1212). If the microcontroller 908 determines that telemetry feedback module 1002 has received telemetry feedback signal, the microcontroller 908 may extract the information contained in the telemetry feedback signal to perform calculations (1216). The extraction may be performed by demodulating the telemetry feedback signal and sampling the demodulated signal in the digital domain. The calculations may reveal operational characteristics of the wireless stimulation device 922, including, for example, voltage or current levels associated with a particular electrode, power consumption of a particular electrode, and/or impedance of the tissue being stimulated through the electrodes.

Thereafter, in certain embodiments, the microcontroller 908 may store information extracted from the telemetry signals as well as the calculation results (1218). The stored data may be provided to a user through the programmer upon request (1220). The user may be the patient, the doctor, or representatives from the manufacturer. The data may be stored in a non-volatile memory, such as, for example, NAND flash memory or EEPROM.

In other embodiments, a power management schema may be triggered 1222 by the microcontroller (908). Under the power management schema, the microcontroller 908 may determine whether to adjust a parameter of subsequent transmissions (1224). The parameter may be amplitude or the stimulation waveform shape. In one implementation, the amplitude level may be adjusted based on a lookup table showing a relationship between the amplitude level and a corresponding power applied to the tissue through the electrodes. In one implementation, the waveform shape may be pre-distorted to compensate for a frequency response of the microwave field stimulator 902 and the wireless stimulation device 922. The parameter may also be the carrier frequency of the transmission signal. For example, the carrier frequency of the transmission signal may be modified to provide fine-tuning that improves transmission efficiency.

If an adjustment is made, the subsequently transmitted transmission signals are adjusted accordingly. If no adjustment is made, the microcontroller 908 may proceed back to polling the telemetry feedback module 1002 for telemetry feedback signal (1212).

In other implementations, instead of polling the telemetry feedback module 1002, the microcontroller 908 may wait for an interrupt request from telemetry feedback module 1002. The interrupt may be a software interrupt, for example, through an exception handler of the application program. The interrupt may also be a hardware interrupt, for example, a hardware event and handled by an exception handler of the underlying operating system.

Figure 13:
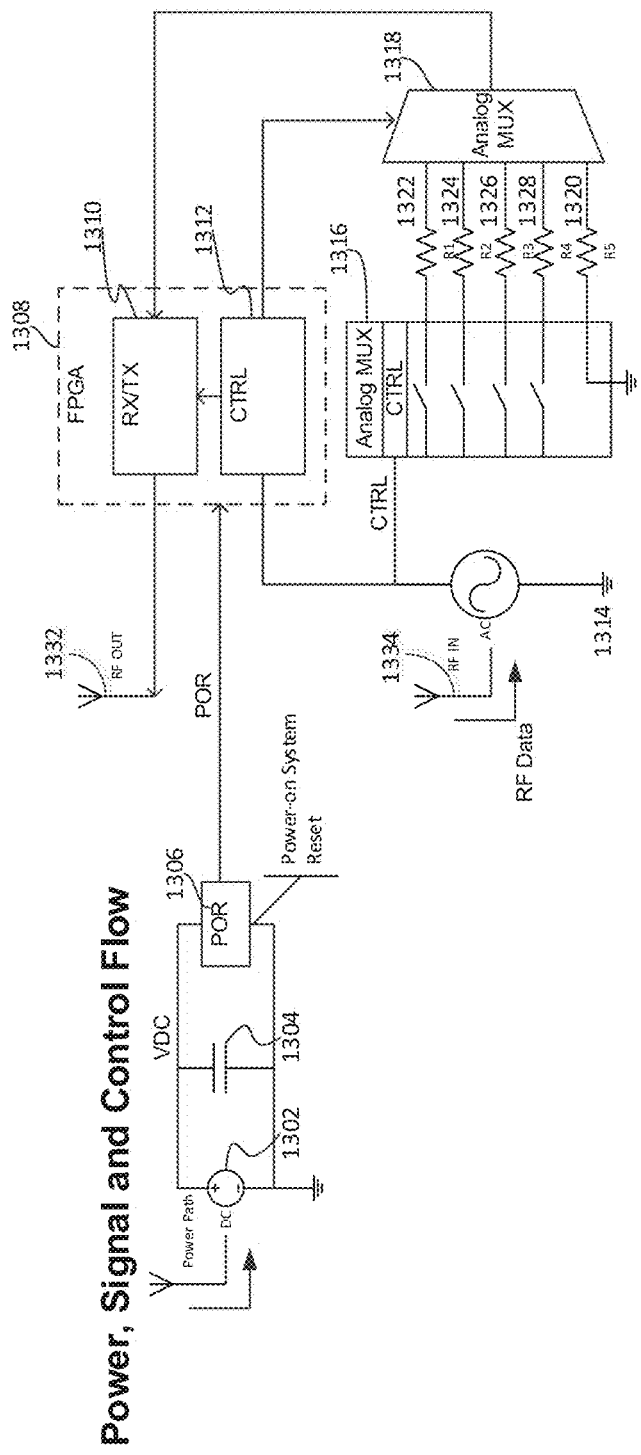
FIG. 13 is a schematic of an example implementation of power, signal and control flow on the wireless stimulation device

FIG. 13 is a schematic of an example implementation of the power, signal and control flow for the wireless stimulation device 922. A DC source 1302 obtains energy from the transmission signal received at the wireless stimulation device 922 during the initial power-on portion of the transmission signal while the RF power is ramping up. In one implementation, a rectifier may rectify the received power-on portion to generate the DC source 1302 and a capacitor 1304 may store a charge from the rectified signal during the initial portion. When the stored charge reaches a certain voltage (for example, one sufficient or close to sufficient to power operations of the wireless stimulation device 922), the power-on reset circuit 1306 may be triggered to send a power-on reset signal to reset components of the neural stimulator. The power-on set signal may be sent to circuit 1308 to reset, for example, digital registers, digital switches, digital logic, or other digital components, such as transmit and receive logic 1310. The digital components may also be associated with a control module 1312. For example, a control module 1312 may include electrode control 252, register file 732, etc. The power-on reset may reset the digital logic so that the circuit 1308 begins operating from a known, initial state.

In some implementations, the power-on reset signal may subsequently cause the FPGA circuit 1308 to transmit a power-on reset telemetry signal back to MFS 902 to indicate that the implantable wireless stimulation device 922 is ready to receive the configuration portion of the transmission signal that contains the polarity assignment information. For example, the control module 1312 may signal the RX/TX module 1310 to send the power-on reset telemetry signal to the telemetry antenna 1332 for transmission to MFS 902.

In other implementations, the power-on reset telemetry signal may not be provided. As discussed above, due to the proximity between MFS 902 and implantable, passive neural stimulator 922, signal degradation due to propagation loss may not be severe enough to warrant implementations of handshake signals from the implantable, passive stimulator 922 in response to the transmission signal. In addition, the operational efficiency of implantable, passive neural stimulator 922 may be another factor that weighs against implementing handshake signals.

Once the FPGA circuit 1308 has been reset to an initial state, the FPGA circuit 1308 transitions to a configuration mode configured to read polarity assignments encoded on the received transmission signal during the configuration state. In some implementations, the configuration portion of the transmission signal may arrive at the wireless stimulation device through the RX antenna 1334. The transmission signal received may provide an AC source 1314. The AC source 1314 may be at the carrier frequency of the transmission signal, for example, from about 700 MHz to about 8 GHz. Thereafter, the control module 1312 may read the polarity assignment information and set the polarity for each electrode through the analog mux control 1316 according to the polarity assignment information in the configuration portion of the received transmission signal. The electrode interface 252 may be one example of analog mux control 1316, which may provide a channel to a respective electrode of the implantable wireless stimulation device 922.

Once the polarity for each electrode is set through the analog mux control 1316, the implantable wireless stimulation device 922 is ready to receive the stimulation waveforms. Some implementations may not employ a handshake signal to indicate the wireless stimulation device 922 is ready to receive the stimulation waveforms. Rather, the transmission signal may automatically transition from the configuration portion to the stimulation portion. In other implementations, the implantable wireless stimulation device 922 may provide a handshake signal to inform the MFS 902 that implantable wireless stimulation device 922 is ready to receive the stimulation portion of the transmission signal. The handshake signal, if implemented, may be provided by RX/TX module 1310 and transmitted by telemetry antenna 1332.

In some implementations, the stimulation portion of the transmission signal may also arrive at implantable wireless stimulation device through the RX antenna 1334. The transmission signal received may provide an AC source 1314. The AC source 1314 may be at the carrier frequency of the transmission signal, for example, from about 700 MHz to about 8

GHz. The stimulation portion may be rectified and conditioned in accordance with discussions above to provide an extracted stimulation waveform. The extracted stimulation waveform may be applied to each electrode of the implantable wireless stimulation device 922. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings for the corresponding channel.

In some implementations, each channel of analog mux control 1316 is connected to a corresponding electrode and may have a reference resistor placed serially. For example, FIG. 13 shows reference resistors 1322, 1324, 1326, and 1328 in a serial connection with a matching channel. Analog mux control 1316 may additionally include a calibration resistor 1320 placed in a separate and grounded channel. The calibration resistor 1320 is in parallel with a given electrode on a particular channel. The reference resistors 1322, 1324, 1326, and 1328 as well as the calibration resistor 1320 may also be known as sensing resistors 718. These resistors may sense an electrical parameter in a given channel, as discussed below.

In some configurations, an analog controlled carrier modulator may receive a differential voltage that is used to determine the carrier frequency that should be generated. The generated carrier frequency may be proportional to the differential voltage. An example analog controlled carrier modulator is VCO 733.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 1320 and the standard voltage. One example standard voltage may be the ground.

In another configuration, the carrier frequency may reveal an impedance characteristic of a given channel. For example, the differential voltage may be the difference between the voltage at the electrode connected to the channel under measurement and a voltage across the reference resistor in series. Because of the serial connection, a comparison of the voltage across the reference resistor and the voltage at the electrode would indicate the impedance of the underlying tissue being stimulated relative to the impedance of the reference resistor. As the reference resistor's impedance is known, the impedance of the underlying tissue being stimulated may be inferred based on the resulting carrier frequency.

For example, the differential voltage may be the difference between a voltage at the calibration resistor and a voltage across the reference resistor. Because the calibration resistor is placed in parallel to a given channel, the voltage at the calibration is substantially the same as the voltage at the given channel. Because the reference resistor is in a serial connection with the given channel, the voltage at the reference resistor is a part of the voltage across the given channel. Thus, the difference between the voltage at the calibration resistor and the voltage across the reference resistor correspond to the voltage drop at the electrode. Hence, the voltage at the electrode may be inferred based on the voltage difference.

In yet another configuration, the carrier frequency may provide a reading of a current. For example, if the voltage over reference resistor 1322 has been measured, as discussed above, the current going through reference resistor and the corresponding channel may be inferred by dividing the measured voltage by the impedance of reference resistor 1322.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. The telemetry feedback signal may include a signal at the resulting carrier frequency.

The MFS 902 may determine the carrier frequency variation by demodulating at a fixed frequency and measure phase shift accumulation caused by the carrier frequency variation. Generally, a few cycles of RF waves at the resulting carrier frequency may be sufficient to resolve the underlying carrier frequency variation. The determined variation may indicate an operation characteristic of the implantable wireless stimulation device 922. The operation characteristics may include an impedance, a power, a voltage, a current, etc. The operation characteristics may be associated with an individual channel. Therefore, the sensing and carrier frequency modulation may be channel specific and applied to one channel at a given time. Consequently, the telemetry feedback signal may be time shared by the various channels of the implantable wireless stimulation device 922.

In one configuration, the analog MUX 1318 may be used by the controller module 1312 to select a particular channel in a time-sharing scheme. The sensed information for the particular channel, for example, in the form of a carrier frequency modulation, may be routed to RX/TX module 1310. Thereafter, RX/TX module 1310 transmits, through the telemetry antenna 1332, to the MFS 902, the telemetry feedback encoding the sensed information for the particular channel.

Figure 14:
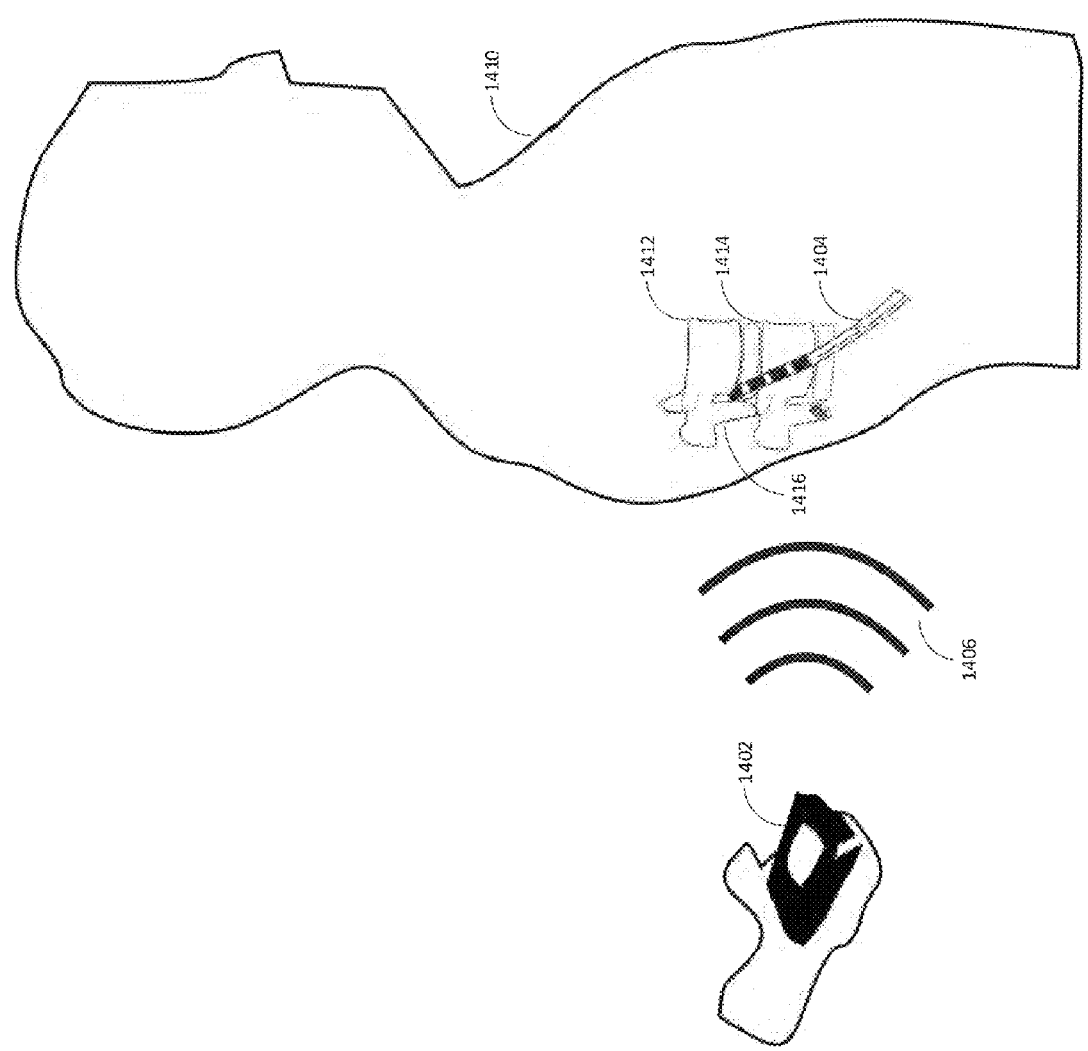
FIG. 14 illustrates an implantable lead or wireless stimulation device and an external microwave field stimulator according to the present invention.

Referring now to FIG. 14, a specific system for modulating excitable tissue in or around the spinal cord will now be described. As shown, the system includes an external microwave field stimulator 1402 and an implantable wireless stimulation device 1404, such as those described in detail above. The external microwave field stimulator 1402 radiates electrical energy 1406 to the wireless stimulation device 1404. In certain embodiments, stimulation device 1404 is implanted in the patient 1410 through foramen 1416 between vertebrae 1412 and 1414. Stimulation device 1404 may also be implanted through a variety of areas in the patient's body, including the sacral hiatus, as will be discussed in association with FIGS. 20A-20C.

In some embodiments, stimulation device 1404 is implanted in proximity to a nerve or nerve ganglion, such as a dorsal root ganglion or dorsal root exiting nerve. The nerve or nerve ganglion can originate from spinal column levels T7 to L5 of the dorsal root ganglia and nerve bundles leaving the dorsal column.

Stimulation device 1404 receives radiated energy 1406 through a receiving antenna(s) system, as described in detail above. The radiated energy 1406 is preferably transmitted in the microwave band of the electromagnetic spectrum. In some embodiments, frequencies from 700 MHz to 8 GHz, preferably between about 800 MHz to 1.2 GHz, are received by the receiving antenna(s). The receiving antenna(s) is small enough to fit within the body of an implantable wireless stimulation device of 1.8 m diameter or smaller. The receiving antenna(s) system preferably includes one or more dipole or patch antenna(s), internal circuitry for frequency waveform and electrical energy rectification, and one or more electrodes allowing for neural modulation of surrounding tissue. The transmitting antenna may be physically adjoined to microwave field stimulator 1402 that generates the stimulation parameter signal. In preferred embodiments, the electrical impulse within the stimulation parameter signal has a frequency of about 10 to 500 Hz, preferably about 10 to 50 Hz, and a pulse width from about 20 microseconds to about 1 millisecond, preferably 500 microseconds. Microwave field stimulator 1402 preferably produces a pulse signal at duty cycles in the range of about 1% to about 10%.

Electric coupling (also known as radiative coupling), rather than inductive coupling, is used to transmit the microwave signals from microwave field stimulator 1402 to stimulation device 1404. The combination of the coupling mechanism and the high frequencies of the microwave signals may allow radio frequency signal penetration at significant tissue depths, for example, up to 13 cm. The greater depth penetration makes the stimulation device 1404 disclosed herein particularly suitable for effective spinal nerve root stimulation.

During operations, an input signal containing electrical energy is transmitted from field stimulator 1402 outside of the patient's body to the implanted receiving antenna(s) via radiative coupling. The internal circuitry generates one or more electrical pulses using the transmitted electrical energy and applies the electrical pulses to the electrodes creating a volume conduction field of energy that can stimulate or inhibit action potentials of the nerves in the surrounding tissue of the implanted device. This modulation of the nerve or nerve ganglion may provide therapeutic pain relief, particularly when the dorsal root exiting nerve or dorsal root ganglion is targeted.

Figure 15:
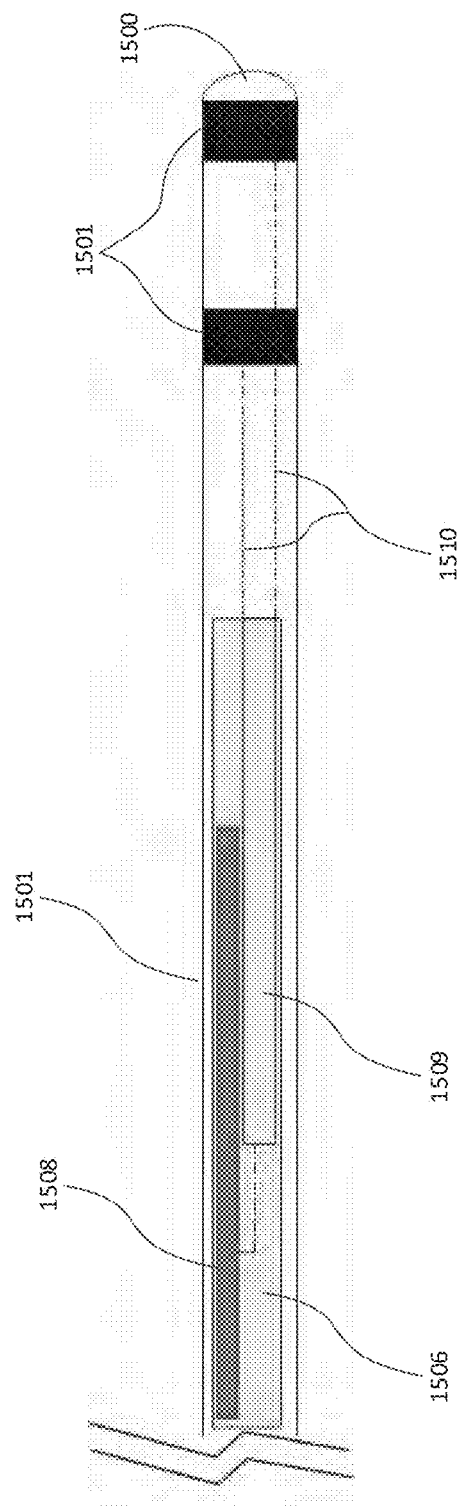
FIG. 15 illustrates an implantable wireless stimulation device according to the present invention that does not connect to an extension cord or an IPG.

FIG. 15 illustrates one embodiment of an implantable wireless stimulation device 1500 according to the present invention. Stimulation device 1500 has a circumferential lead body that includes between one and four flexible circuits 1506 coupled to receiving antenna(s) 1508. The flexible circuit(s) 1506 includes circuitry to condition the received wireless energy and produce a suitable modulation waveform that is routed to the electrodes 1503 by wires 1510 in order to modulate nerves within the surrounding tissue.

Stimulation device 1500 can include one or more multiple receiving antennas 1508. The dipole configuration receiving antenna(s) may range from as small as 100 microns up to 8 cm in length, depending on the indication and location of the stimulation device placement. Receiving antenna(s) 1508 may include any linear dipole configuration ranging from about 100 microns to about 4 mm in thickness. In some implementations, receiving antenna(s) 1508 comprise a conductive trace feature within the flexible circuit 1506. In other embodiments, receiving antenna(s) 1508 are fabricated with conductive wires connected to the flexible circuitry 1506. Receiving antenna 1508 is non-inductive and provides sufficient power to produce currents capable of modulating nerves remotely, while being small enough to form factor to fit within a lead body having a diameter of less than 1.8 mm.

In some embodiments, the wireless stimulation device 1500 may include one to four electrodes 1503 ranging from about 1 mm to about 10 mm in length and 1 mm to about 4 mm in width. The electrodes 1503 preferably include at least one anode and multiple cathodes coupled to the targeted tissue. The electrical impulses preferably range from about 0 to about 15V peak amplitude at a pulse width of about to a maximum of 1 millisecond. The polarity of electrodes 1503 produces a volume conduction distribution from the cathodes to the anodes to inhibit or excite nerves within surrounding tissue. The embodiments disclosed herein may include anywhere between one to twenty electrodes, preferably one to four electrodes, that can be designated as either a cathode or anode. The electrode impedance is preferably as low as possible. Therefore, the electrodes preferably comprise materials such as platinum, iridium, a combination alloy of the two metals, or similar such materials. In an exemplary embodiment, a combination alloy of platinum and iridium is used to increase the strength of the fabricated electrodes 1503.

Flexible circuitry 1506 in the wireless stimulation device routes the waveform or electrical impulse to electrodes 1503 for the modulation of excitable tissue. The waveform carried to the tissue is preferably at lower frequencies (i.e., less than about 10,000 Hz), and more preferably below 100 Hz. Flexible circuitry 1506 may include a plurality of diodes to rectify the microwave signal received by the implanted dipole receiving antenna(s). The diodes have a low threshold voltage to maximize the energy used for modulation. Flexible circuitry 1506 may also include charge balance microelectronics to prevent the corrosion of the electrodes. The wireless stimulation device 1500 preferably includes isolation circuitry to block high frequency and pass low frequency signals such that electrical energy is not reflected from the electrodes.

Excluding the electrodes, the remaining portions of wireless stimulation device 1500 are partially or completely insulated from surrounding body tissue with an external coating layer of biocompatible dielectric material with a low dielectric constant. Materials with rigidity similar to that of the tissue are ideal to reduce the risk of migration and limit the development of fibrous scar tissue that can increase electrode-tissue impedance. Low impedance materials reduce the amount of energy dissipation through the lead, thereby increasing the efficiency of the stimulation of targeted tissues.

In some embodiments, the wireless stimulation device 1500 comprises multiple layers. Theses layers can include, without limitation, a first encasing layer closest to the electrodes comprising a biocompatible material that elicits minimal scar formation. Preferred materials for this layer include, without limitation, polymethymethacrylate (PMMA), polydimethylsiloxane (PDMS), parylene, polyurethane, polytetrafluorethylene (PTFE), polycarbonate and the like. A second layer of a material with low relative permeability and low conductivity is located above the dipole antennas to allow for optimal coupling with an exterior antenna. A third layer may comprise a coating of a silicone elastomer to assist in anchoring stimulation device 1500 to the surrounding tissue.

Figure 16A:
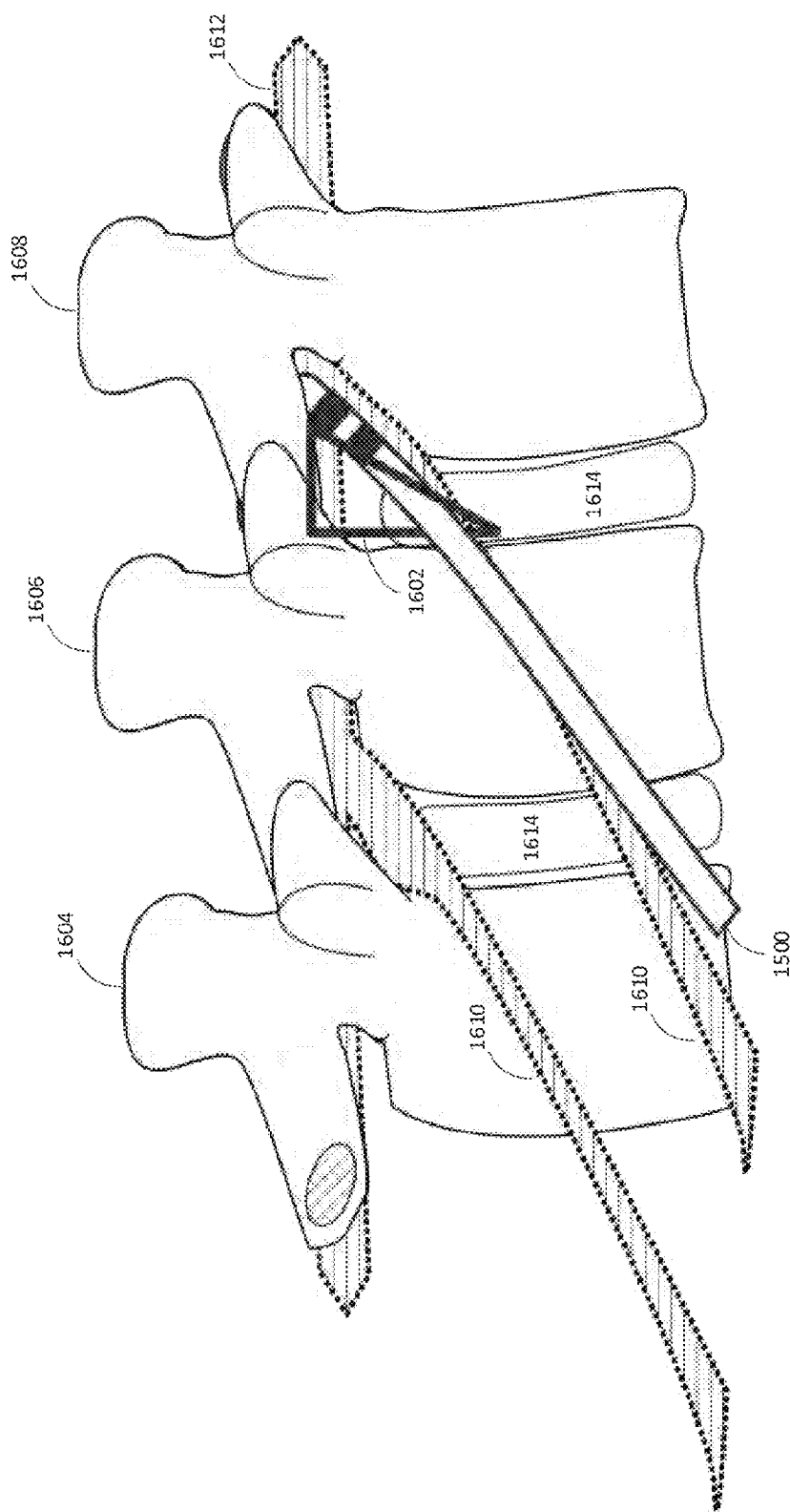
FIG. 16A illustrates placement of the wireless stimulation device transforaminally into the Kambin's triangle according to one embodiment of the present invention.

FIG. 16A illustrates one embodiment of a method of positioning and anchoring the wireless stimulation device 1500 transforaminally into the Kambin's triangle. As shown, the wireless stimulation device 1500 is advanced into the Kambin's triangle 1602 through a cannula to access the ventral side of the spinal cord 1612. The wireless stimulation device 1500 is placed in close proximity to specific excitable tissue, such as the exiting nerve bundles 1610, and not in a general location such as over the dorsal column vertebrae 1604, 1606, 1608 or the intervertebral discs 1614. The Kambin's triangle is often the site of pain generating nerves. However, wired leads generally cannot be introduced and implanted within Kambin's triangle close enough to provide effective stimulation of these pain generating nerves. The present invention allows a clinician to implant a wireless stimulation device into the Kambin's triangle to modulate the dorsal nerve bundles therein, thereby more effectively reducing the patient's pain.

In certain embodiments, the implanting process begins with the step of advancing at least a portion (i.e., the distal portion) of wireless stimulation device 1500 containing the electrodes through an intervertebral foramen opening into Kambin's triangle. In one preferred embodiment, an opening of a lumen is placed near the intervertebral foramen opening and at least the distal portion of the wireless stimulation device 1500 is advanced through the lumen and out of the distal lumen opening such that the distal portion of the wireless stimulation device 1500 passes through the intervertebral foramen opening. The lumen is preferably part of a cannula, spinal needle, endoscope or the like.

After the distal portion of the wireless stimulation device 1500 is positioned near the target site in Kambin's triangle, it is fixated or anchored at the target site such that the receiving antenna(s), electrodes and circuitry of the wireless stimulation device 1500 are completely contained within the body of the patient. An input signal is delivered to device 1500 and one or more electrical impulses are generated to modulate a nerve or nerve ganglion in or near the Kambin's triangle.

The method of the present invention obviates the need for an extension cord to be tunneled to an implanted pulse generator. As such, direct placement of wireless stimulation device 1500 at a location adjacent to the nerves near the spinal column may be achieved. This provides distinct benefits over spinal cord stimulation systems or other systems that would require a connective wire to be tunneled to the lead through the epidural space of other body tissue. For example, the volume conduction is localized in a more optimal fashion with the present invention than with prior art stimulation devices. Thus, the amount of current required to create an electric field for activation of sub-threshold potential may be reduced when the device is local to the nerve, rather than a substantial distance away, e.g., the dorsal column placement of a lead. Therefore, the localized placement of stimulation device 1500 may enable a reduction in requirement for multiple electrode pairs.

The wireless stimulation device 1500 may be placed at various vertebrae levels in the lumbar and thoracic regions of the spinal column. The transforaminal approach may allow for direct access to nerve bundles that could be classified as pain generators located in or around: the disc, the exiting nerve, the traversing nerve, the epidural space, the superior facet, the axilla containing the dorsal root nerve bundles, or foraminal osteophytes.

FIG. 16B illustrates a dorsal-ventral view of the placement of the wireless stimulation device 1500 through an angular approach to the Kambin's triangle 1602. The wireless stimulation device 1500 is advanced through a spinal needle 1622 through the foramen 1416 in a ventral angular approach into the region of the Kambin's triangle 1602. During implantation, a cannula may be placed through the Kambin's triangle 1602 to provide direct access to the exiting nerve bundles from the L5 level to the T12 level of the patient's spine, where the access space is in the range of about 7 cm to about 10 cm. The wireless stimulation device 1500 is preferably placed at the T12 level and then turned to enable guidance upward to access dorsal root ganglions or exiting nerve bundle roots at dermatome levels T11 to T7, where the direct access space would be too small (e.g., about 2 cm) for standard cannulas to be placed through the foramen. The foraminal approach may access nerve bundles classified as pain generators located in or around: the disc, the exiting nerve, the traversing nerve, the epidural space, the superior facet, the axilla containing the dorsal root ganglion or foraminal osteophytes.

Figure 16C:
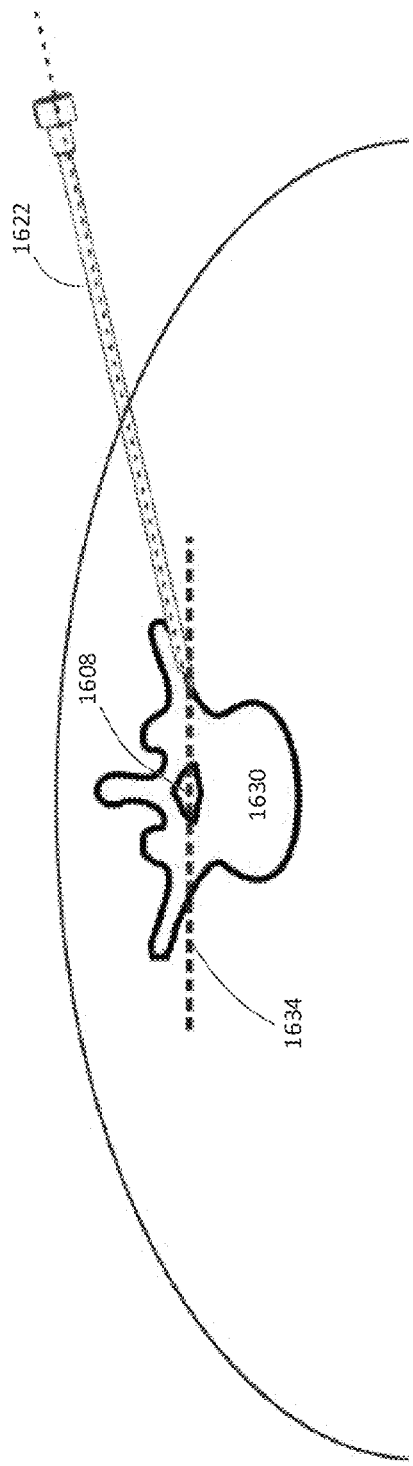
FIG. 16C is a caudal-cranial view of the placement of the wireless stimulation device through an angular approach to the Kambin's triangle.

FIG. 16C illustrates a caudal-cranial view of the placement of the wireless stimulation device 1500 through an angular approach to the Kambin's triangle 1503. Stimulation device 1500 is advanced through a spinal needle 1622 in a ventral angular approach into Kambin's triangle 1503. Spinal needle 1622 is pointing at the pedicle area of vertebra 1630. Spinal cord channel 1622 is within vertebra 1630. One of the advantages of the approaches described in FIGS. 16A-16C is that wireless stimulation device 1500 is advanced to the target site from the side of the patient's body. Thus, the wireless stimulation device 1500 is not tunneled through the epidural space to access the exiting nerve roots from the spinal column as with prior art leads.

Figure 16D:
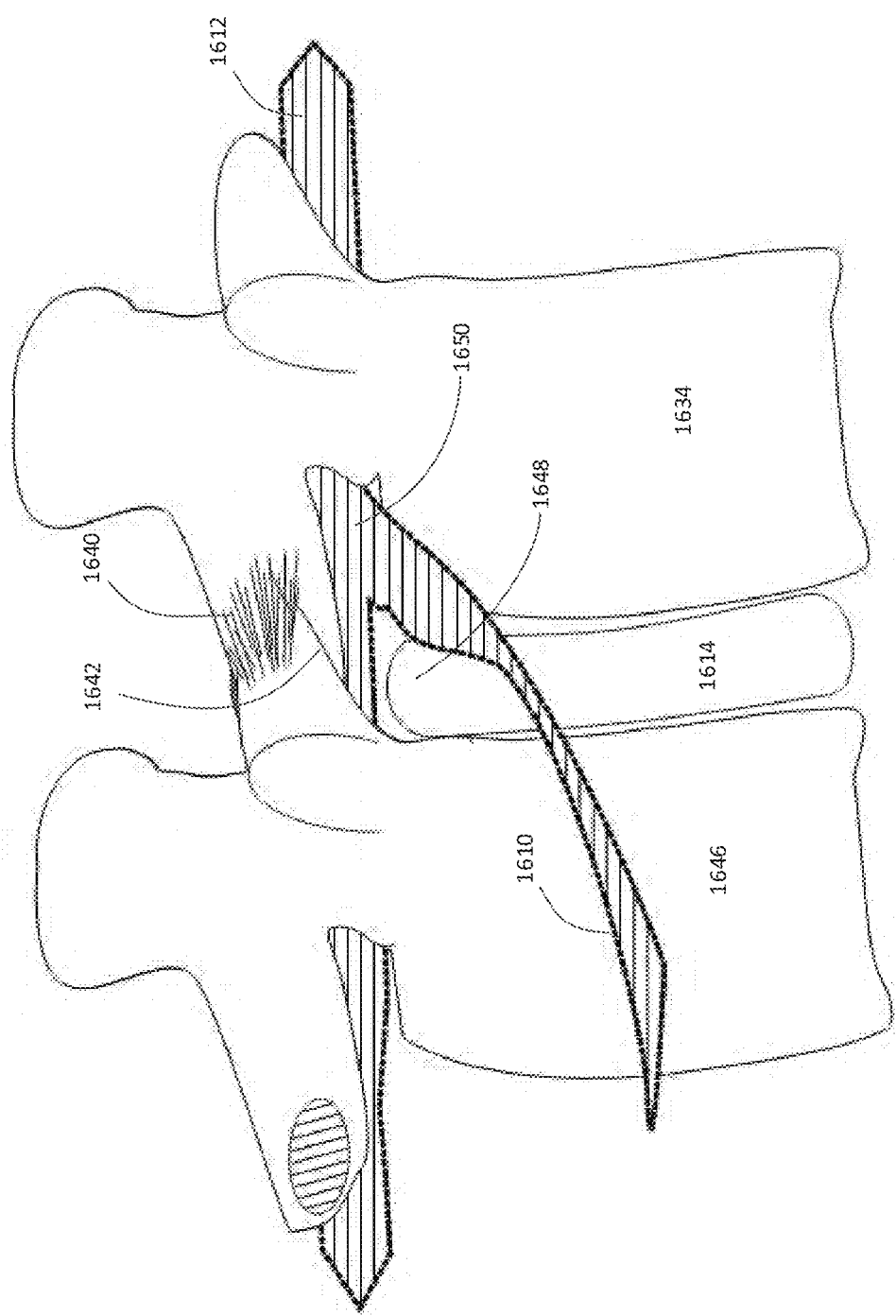
FIG. 16D illustrates the various anatomical structures at the implantation site of the wireless stimulation device according to the present invention.

FIG. 16D illustrates various anatomical structures at the placement site of the wireless stimulation device 1500. The pedicle area 1634 is outside of a vertebra and approximately at the same level as the spinal cord 1612. The exiting nerve bundle 1610 extends from the facet joint 1642 over the intradisc aleva 1644 and vertebral body 1646. The facet ligament 1640 partially covers the facet joint 1642.

FIG. 17A illustrates another embodiment of the present invention wherein the wireless stimulation device 1700 contains suture locations that allow the device 1700 to be anchored or fixated to tissue or bone after it has been positioned at the target site. In this embodiment, the wireless stimulation device 1700 is a circumferential lead and comprises at least two electrodes and multiple suture locations, such as suture addendums 1702, 1704, 1706, 1708 and 1710. The suture addendums assist with anchoring the wireless stimulation device 1700 to soft tissue or bone matter. The lead body of wireless stimulation device 1700 may have one addendum at the distal tip for a suture loop, or as many as eight addendums along the body of the device 1700. Alternatively, the addendums may be extrusions, extruding structures, extruding features or prongs.

Suturing addendums 1702, 1704, 1706, 1708 and 1710 may be pre-threaded with suture prior to placement of the wireless stimulation device 1700 through the entry port of the tissue. Anchoring sutures can include, but are not limited to, nylon suture, silk suture, ethibond or the like. The suture material may be formed from any suitable biocompatible material that is flexible and sterile. The suture material may be braided, although a smooth, non-braided suture is preferred for ease of removal.

Figure 17B:
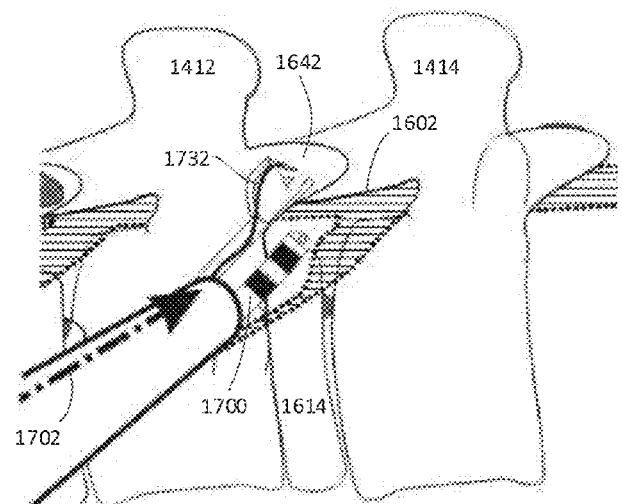
FIGS. 17B and 17C illustrates a method according to the present invention for fixating a wireless stimulation device to the pedicle area accord.
Figure 17C:
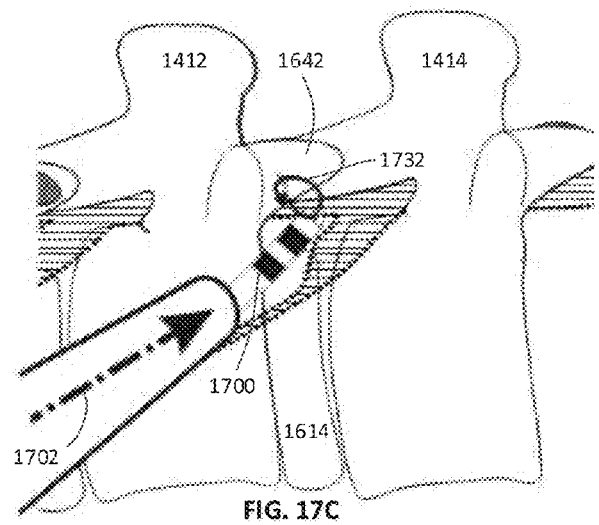

FIGS. 17B and 17C illustrate methods for anchoring the wireless stimulation device 1700 to the pedicle area. As shown in FIG. 17B, the wireless stimulation device 1700 is advanced through a lumen, such as a spinal needle or cannula, and positioned into the Kambin triangle. The pre-threaded suture 1732 is placed into the intervertebral space between vertebrae 1412 and 1414. As shown in FIG. 7C, the pre-threaded suture 1732 forms a loop over the facet joint 1642. The loop ties suture addendum 1710 to facet joint on the vertebral body of vertebra 1414. Anatomical soft tissues that can serve as anchoring points for the suturing process include, but are not limited to, the annulus 1648, facet joint 1643, or pedicle 1634 (as shown in FIG. 16D).

Using the above methods of the present invention, the wireless stimulation device 1700 can be placed with one or more electrodes adjacent to or near the cranial and caudal nerve branches leading to facet joint 1642 to provide permanent joint nerve stimulation to the nerve bundles closest to the facet joint. A facet joint 1642 may have one nerve from a more rostral foramen nerve, passing caudally along the vertebra and going to the top of the joint, and one nerve from the immediate foramen about the joint, looping around and passing rostrally to the same joint. Thus, spinal nerves in close proximity to the foramen exit are also in close proximity to the facet joints.

In one aspect, a cannula 1702 is placed over the lead body of the wireless stimulation device 400 and slid down to the distal tip of the device 1700 to tie off suture 1732. In a removal procedure, the cannula 1702 may also be placed against the suture 1732 and used to disconnect suture 1732 and extract the wireless stimulation device 1700 from the patient's body.

The exiting cannula 1702 may also be used to re-secure the device 1700 in case of migration or dislodgement.

Figure 17D:
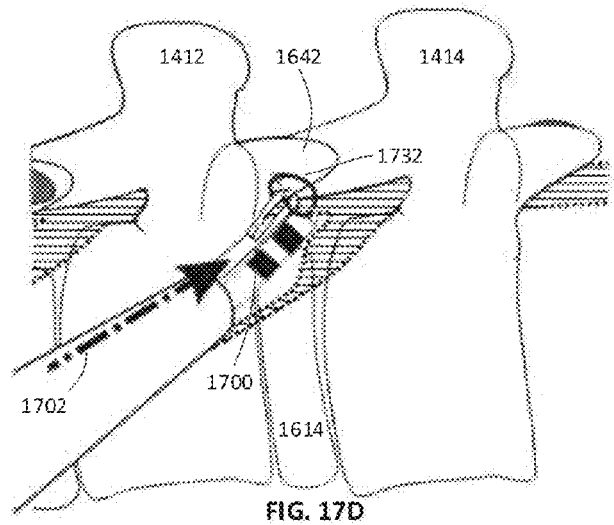
FIG. 17D illustrate a method for removing a suture that fixes the wireless stimulation device to the pedicle area.

FIG. 17D illustrates another method of the present invention for removing a wireless stimulation device 1700 that is anchored to the pedicel area. As shown, a cutting device 1742 is advanced or pushed through a cannula 1702 towards the suture loop formed by suture 1732. On contact with the loop, the cutting device 1742 cuts the suture loop and disconnects stimulation device 1700 from the anchoring site, for example, the facet joint 1642. The disconnected stimulation device 1700 may then be extracted from the patient through cannula 1702. This method may be visualized and performed under imaging techniques, such as fluoroscopy, ultrasound or the like.

In an alternative embodiment, an endoscope may be used for insertion and removal of a wireless stimulation device 1702 (rather than cannula 1702). In this embodiment, an endoscope has an instrument channel through which a wireless stimulation device 1700 may be pushed or advanced into the Kambin's triangle. Using an endoscope for the suturing process may achieve a stronger fixation of the wireless stimulation device 1700 to the anchoring tissue because the suturing process may be visualized in real time by the camera of the endoscope. The endoscope may also allow for more complex anchoring mechanisms.

Figure 18A:
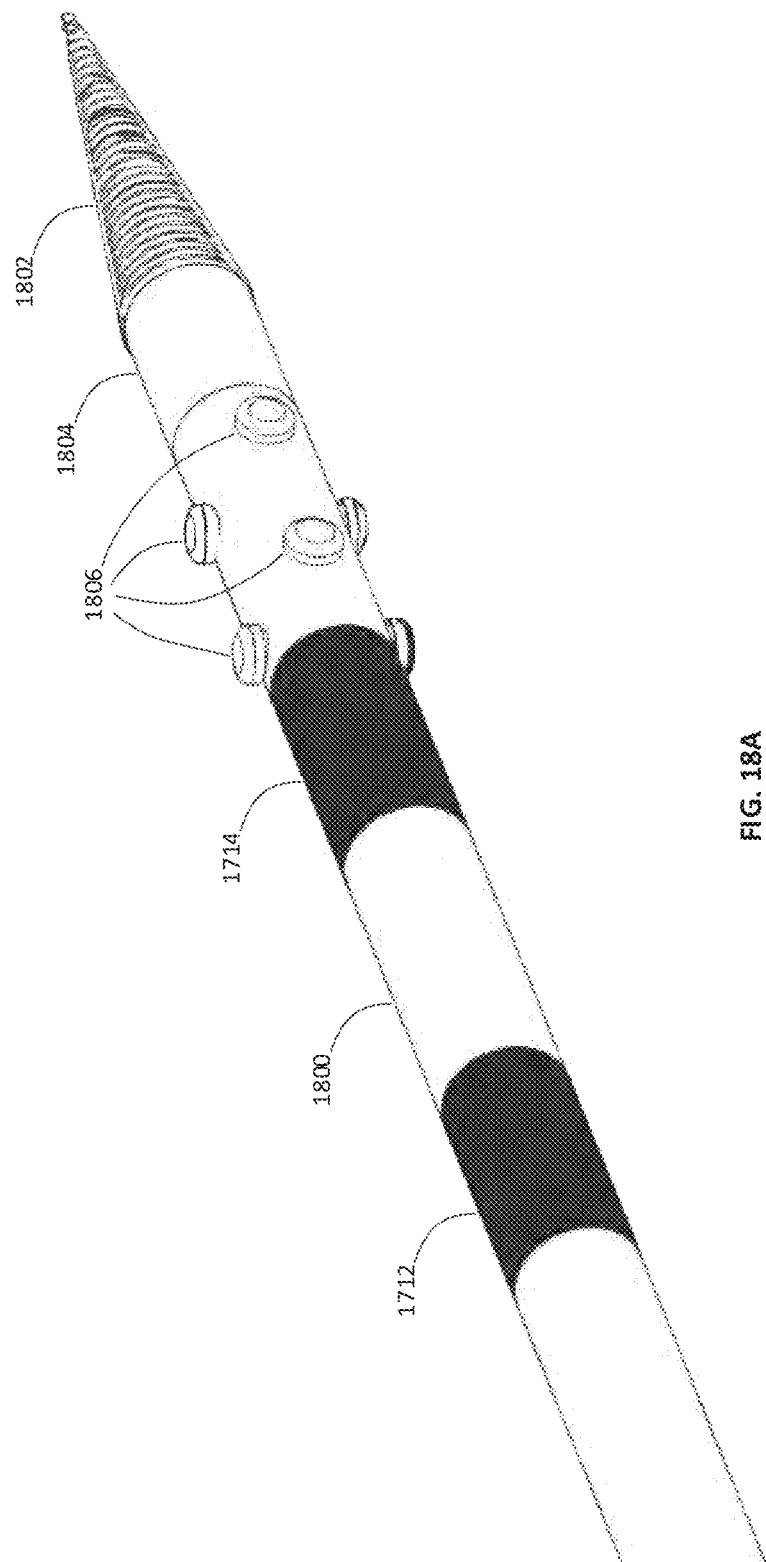
FIG. 18A illustrates another embodiment of a wireless stimulation device according to the present invention with a screw-tip.

FIG. 18A illustrates another embodiment of the present invention wherein a wireless stimulation device 1800 comprises a screw-tip 1802 at its distal end. As shown, wireless stimulation device 1800 has a hard tissue screw built-in to its distal tip to form the screw-tip 1802. Screw-tip 1802 can be integrated into the soft plastic body of the wireless stimulation device 1800 through, for example, one or more small bolts that tighten the metallic core of screw-tip 1802 with the plastic body. Screw-tip 1802 preferably comprises a biocompatible metal that is strong, durable and rigid, such as titanium or the like, screw-tip 1802 may be used as an anchoring mechanism, as discussed below in association with FIG. 18D. In this embodiment, stimulation device 1800 is a circumferential lead that includes electrodes 1712, bolts 1806 and a metal cover 1805. The wireless stimulation device 1800 may include from two to ten, preferably between 2-4, electrodes 1712 and electronics and circuitry embedded into the plastic encapsulation.

FIG. 18B illustrates another embodiment wherein the wireless stimulation device 1800 comprises of a screw-tip 1804 and a tool 1812 for anchoring or securing a wireless stimulation device 1800 to the target site in the patient. A screw-tip 1802 is preferably a machined extrusion and tapers from between about 0.001 mm to about 2.5 mm in width. Screw-tip 1802 may be wider than the outer diameter of the wireless stimulation device 1800 and may contain female triangular dents on its edges. Tool 1812 includes male stubs 1814 and locks with screw-tip 1802 by engaging male stubs 1814 with the triangular dents on screw-tip 1802.

FIG. 18C illustrates a method according to the present invention of securing a wireless stimulation device 1800 with tool 1812. As shown, tool 1812 is configured to slip over the exterior body of a wireless stimulation device 1800 to engage with device 1800 in a solid male/female connection. Thereafter, tool 1812 is rotated clockwise to anchor the wireless stimulation device 500 by drilling screw-tip 1810 into bony tissue, such as the pedicle, spinous process, transverse process and/or vertebrae. During the anchoring process, the body of the wireless stimulation device 180° rotates with tool 1812.

FIG. 18D illustrates yet another embodiment of the present invention. As shown, the wireless stimulation device 1800 is attached to a screw-tip 1802 by an extruded tethering component. In this embodiment, the wireless stimulation device 1800 is a circumferential lead includes at least two electrodes 1712, a tethering component 1842 and a screw-tip 1802 (as well as the receiving antenna(s) and circuitry discussed above). Tethering component 1842 preferably comprises a biocompatible material such as nylon, ETFE coated MP35N or the like. The biomaterial is preferably strong and flexible to minimize migration of the wireless stimulation device 1800 and to prevent the device 1800 from being pulled out of place via attachment to tethering component 1842. Tethering component 1842 can be made of varying lengths between about 4.0 mm to about 600 mm. Tethering component 1842 connects the body of the wireless stimulation device 1800 to a screw-tip 1802. The detachment of the screw from the lead boy allows greater flexibility of the wireless stimulation device 1800 while the patient is moving. Screw tip 1802 preferably comprises a biocompatible material such as titanium or the like, as discussed above. Screw-tip 1802 may have threads 1844 through which screw-tip 1802 is secured into bone tissue around the spinal column. Screw-tip 1802 could be secured into the bony tissue through a screwdriver-type tool that engages with the shape of the head of screw-tip. The head of the screw may be a standardized shape, such as Phillips, hex, Torx, pentalobular or the like. Alternatively, the head of the screw may be a proprietary shape. The bone tissues for anchoring may include, for example, the pedicle, spinous process, transverse process and/or vertebrae.

A method for implanting the wireless stimulation device 1800 transforaminally is shown in FIG. 18D.

Figure 19:
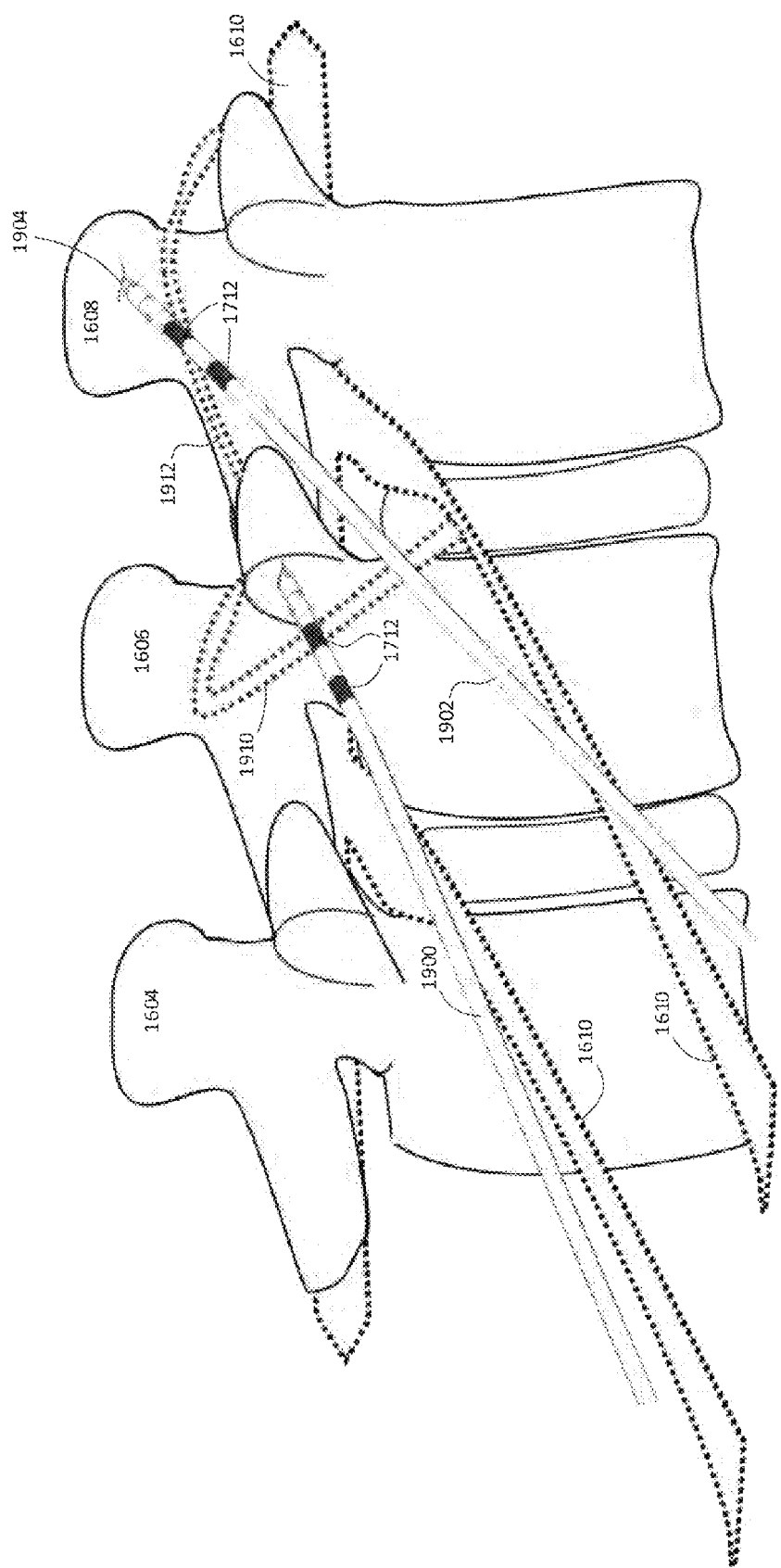
FIG. 19 illustrates a method for anchoring two wireless stimulation devices with screw-tips to stimulate the medial branch and the articular branch.

FIG. 19 illustrates a method according to the present invention of anchoring two implantable wireless stimulation devices with distal screw-tips to stimulate the medial branch and the articular branch of a spinal nerve. As shown, wireless stimulation devices 1900 and 1902, each with a screw-tip, are being positioned through respective Kambin's triangles.

A wireless stimulation device 1900 may be secured by rotating the screw-tip into hard tissues, such as the pedicle, spinous process and/or vertebrae 1606, as discussed above.

Securing the wireless stimulation device to the hard tissue prevents migration and allows more accurate and durable stimulation. Once the wireless stimulation device 1900 is secured in place, it may provide electrical stimulation through the electrodes 1712 to the articular branch 1910 of the spinal nerve. Likewise, the wireless stimulation device 1902 may be secured by rotating screw-tip into hard tissue, such as the pedicle, spinous process, transverse process and/or vertebrae 1608. Once secured in place, the wireless stimulation device 1902 may provide electrical stimulation through electrodes 1712 to medial branch 1912 of the spinal nerve.

In other embodiments, wireless stimulation devices 1900 or 1902 may be implanted to provide electrical stimulation to the exiting nerve bundles 1610 that extend over vertebrae 1604.

FIG. 20A illustrates another embodiment of the present invention wherein a wireless stimulation device 2000 comprises of prongs 2002 and 2004. Prongs 2002, 2004 may comprise a soft plastic material that is integrated into the plastic body of a wireless stimulation device 2000 near the electrodes 1712. Prongs 2002, 2002 may secure themselves into a number of soft tissues around the spinal column, such as the annulus, the fibrous soft tissue of the inter-transverse ligament fatty tissue and the like. Thus, the disclosed wireless stimulation device may include anchoring prongs that can assist in placing the lead both directly outside and inside the foramen, while anchoring the wireless stimulation device and inhibiting movement in either direction. Additionally, the prongs may have the ability to slide along the restricted anchoring section of the wireless stimulation device to be placed in the most desirable location for fixation by the clinician.

FIG. 20B illustrates a method according to the present invention of implanting the wireless stimulation device 2000 of FIG. 20A. As shown, prongs 2002, 2004 of the wireless stimulation device 2000 are anchored into the soft tissue of the annulus (ANN), the fibrous soft tissue of the inter-transverse ligament (LIG) and fatty tissue (FT) located between vertebrae 1412 and 1414. A sub-section of the exposed spinal column structures are shown depicting the ligamentum flavum, the foraminal ligament, the fat in the epidural space, the dura of the spinal cord and the nerve bundles including the dorsal root ganglion 9DRG), the exiting nerve root and the traversing nerve (TN) root. The barbed anchoring mechanism of stimulation device 2000 allows the wireless stimulation device to progress medially during an implantation process, towards the midline of the spinal cord (SC). This medial migration is less likely to occur when the wireless stimulation device has been secured with suture. Nonetheless, the barbed anchoring mechanism can still mitigate backward migration by spreading the surface area of the barbs into a network of soft tissue to reduce migration lateral to the spinal midline.

Figure 21A:
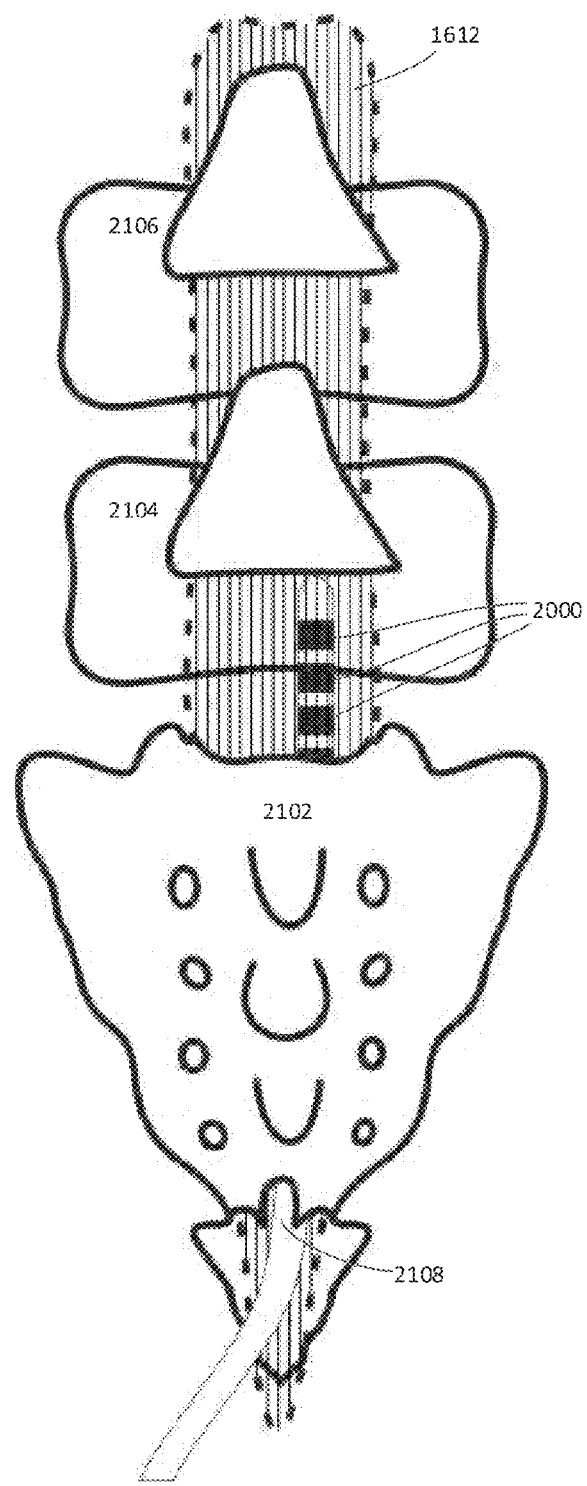
FIG. 21A illustrates another method of the present invention for placement of a wireless stimulation device through the sacral hiatus access port into the epidural space ventrally next to the dorsal root ganglion and/or exiting nerve bundles.

FIG. 21A illustrates a method according to the present invention of positioning a wireless stimulation device 2110 through the sacral hiatus 2108 access point into the epidural space ventrally to be guided through the epidural space up to the dorsal root and exiting nerve bundles of the targeted vertebrae level(s). For this method, the wireless stimulation device 2110 may be any of the combinations of wireless stimulation devices described in this application. As shown, sacral hiatus 2108 is located towards the caudal end of sacrum 2102. From the access point at the sacrum hiatus 2108, a guide wire is utilized to advance the wireless stimulation device 2110 into the lumbar region, for example, anywhere from L1 to L5, or to T12 dermatome levels on the ventral side of spinal cord 1612. Once the lead has been advanced into the target region of the appropriate vertebrae (e.g., one of the vertebrae 2102 and 2104), the wireless stimulation device 2110 is preferably routed to the foraminal space in proximity to the dorsal root and exiting nerve bundles. As discussed above, the wireless stimulation device 2110 may provide electrical stimulation or modulation to the dorsal root and exiting nerve bundles through electrodes 1712.

Figure 21B:
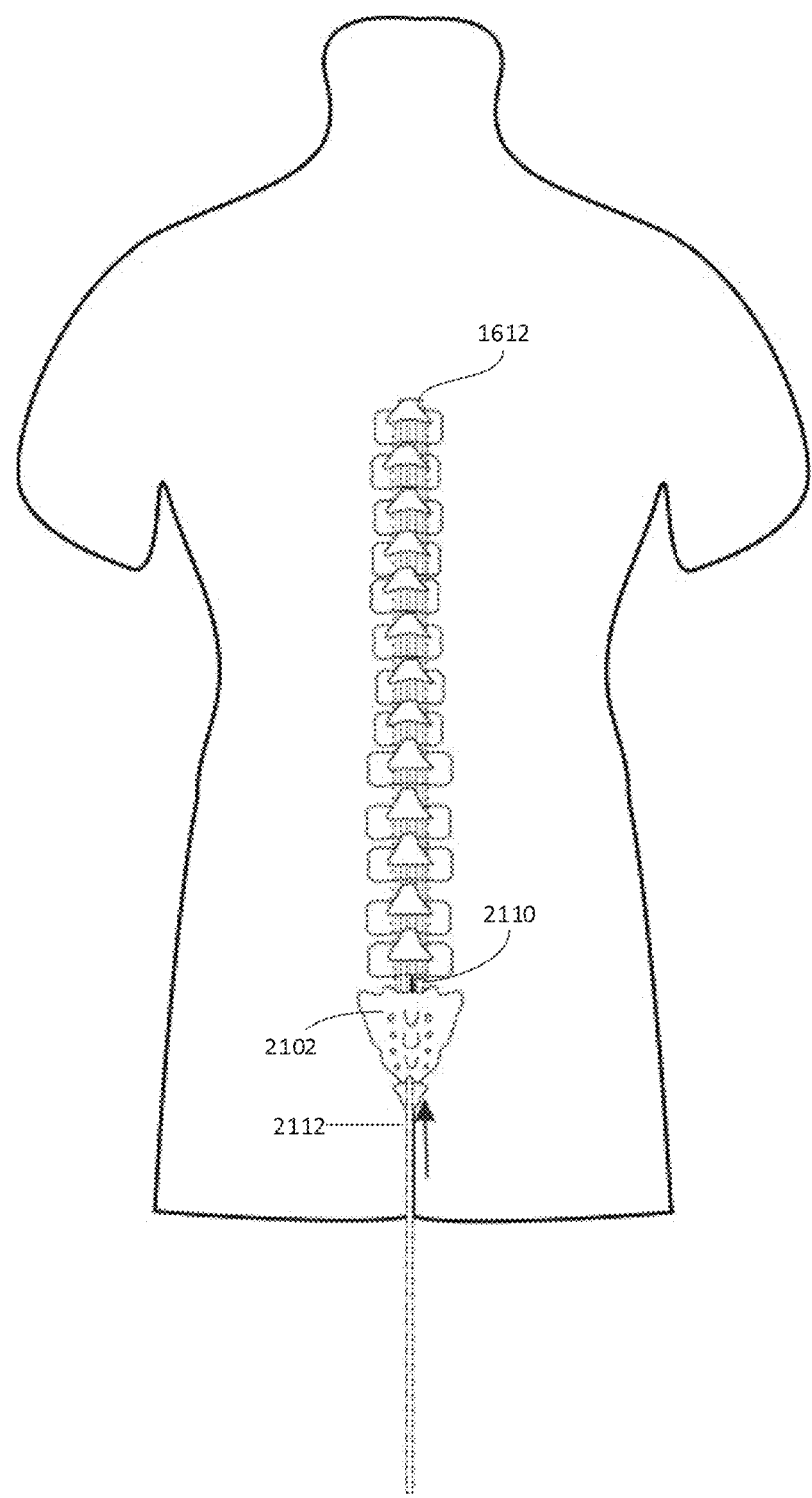
FIG. 21B is a dorsal-ventral view of the placement of a wireless stimulation device utilizing a spinal needle through the sacral hiatus.

FIG. 21B illustrates a dorsal-ventral view of the placement of the wireless stimulation device 2110 by using a spinal needle. FIG. 21C illustrates a caudal-cranial view of the placement of the wireless stimulation device 2110 utilizing a spinal needle 2112 through the sacral hiatus. Spinal needle 2112 is preferably inserted through sacral hiatus 2108. As discussed above, the non-inductive coupling between the wireless stimulation device 2110 and an external microwave field stimulator allows for a small receiving antenna(s) to be placed within the lead body of the wireless stimulation device 2110. As a result, the form factor of stimulation device 2110 can be made small enough (e.g., 1.8 mm in diameter or smaller) to be placed through the access ports at the sacral hiatus and routed to nerve bundles in the thoracic and lumbar regions. The access port may be associated with a spinal needle 2112 or any other similar cannula. Through a spinal needle 2112, the wireless stimulation device 2110 is preferably inserted long with a guide wire (not shown). The guide wire is preferably more rigid than plastic tubing and thus can provide guidance while inserting the wireless stimulation device 2110 up along the mid-line of the spinal column.

FIGS. 22A-D illustrate a method of positioning a wireless lead, such as one of the leads described above, adjacent to, or in close proximity to, the exiting spinal nerves or nerve ganglion. The series of steps demonstrate placement of the injection system and gliding the lead moving through the lumen of the introducer till the electrode array is in close proximity to the exiting nerves or nerve ganglion.

Figure 22A:
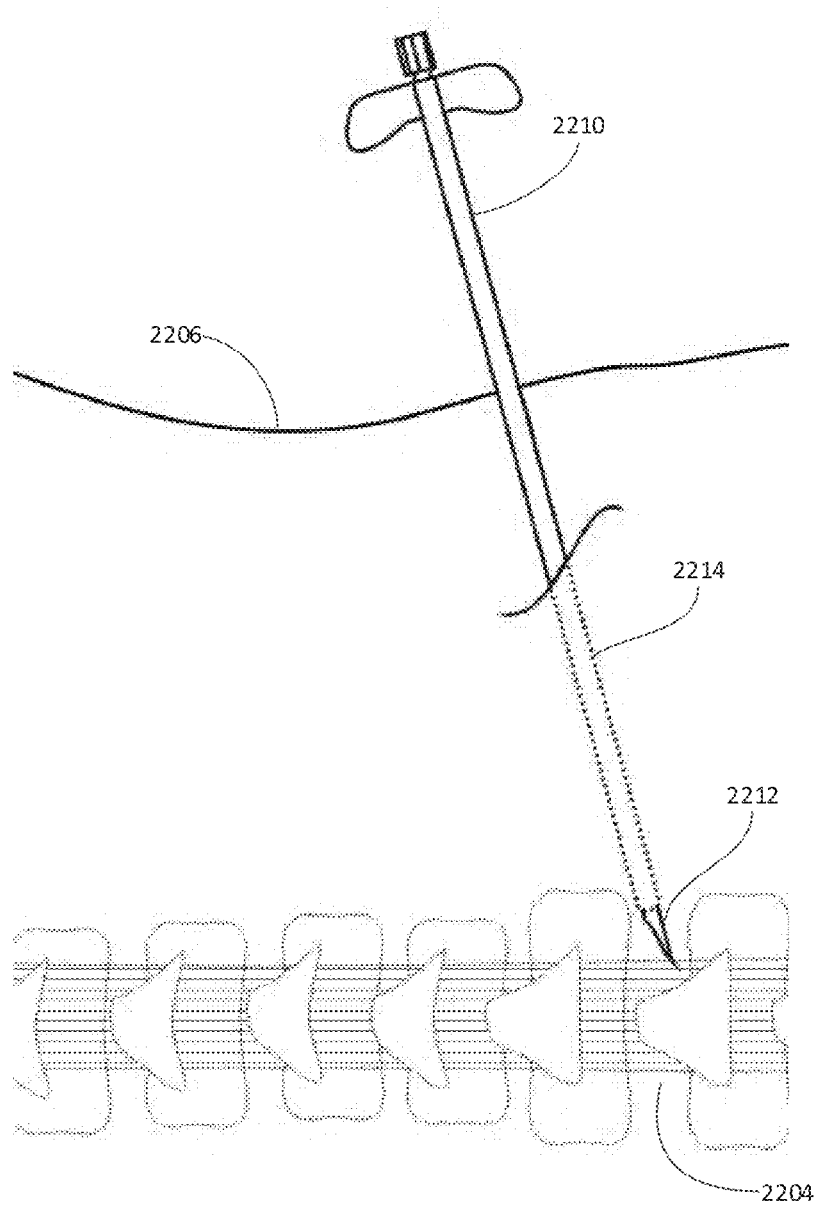
FIGS. 22A-D illustrates the series of steps needed to demonstrate placement of the injection system, gliding the lead moving through the lumen of the introducer till the electrode array is in close proximity to the exiting nerves or nerve ganglion.

FIG. 22A illustrates the placement of the spinal needle 2214 and the introducer 2210 at the lumbar disc level 2204 on the dorsal aspect of a patient. The spinal needle 2214 has a sharp tip 2212 to pierce through tissue 2206. Spinal needle 2214 may have a spoonbill tip 2212 to assist in guiding a lead out of its inner lumen into an operator specified direction. Before the wireless lead is energized through RF energy, the metallic spinal needle 2214 can be retracted proximally from introducer 2210.

Figure 22B:
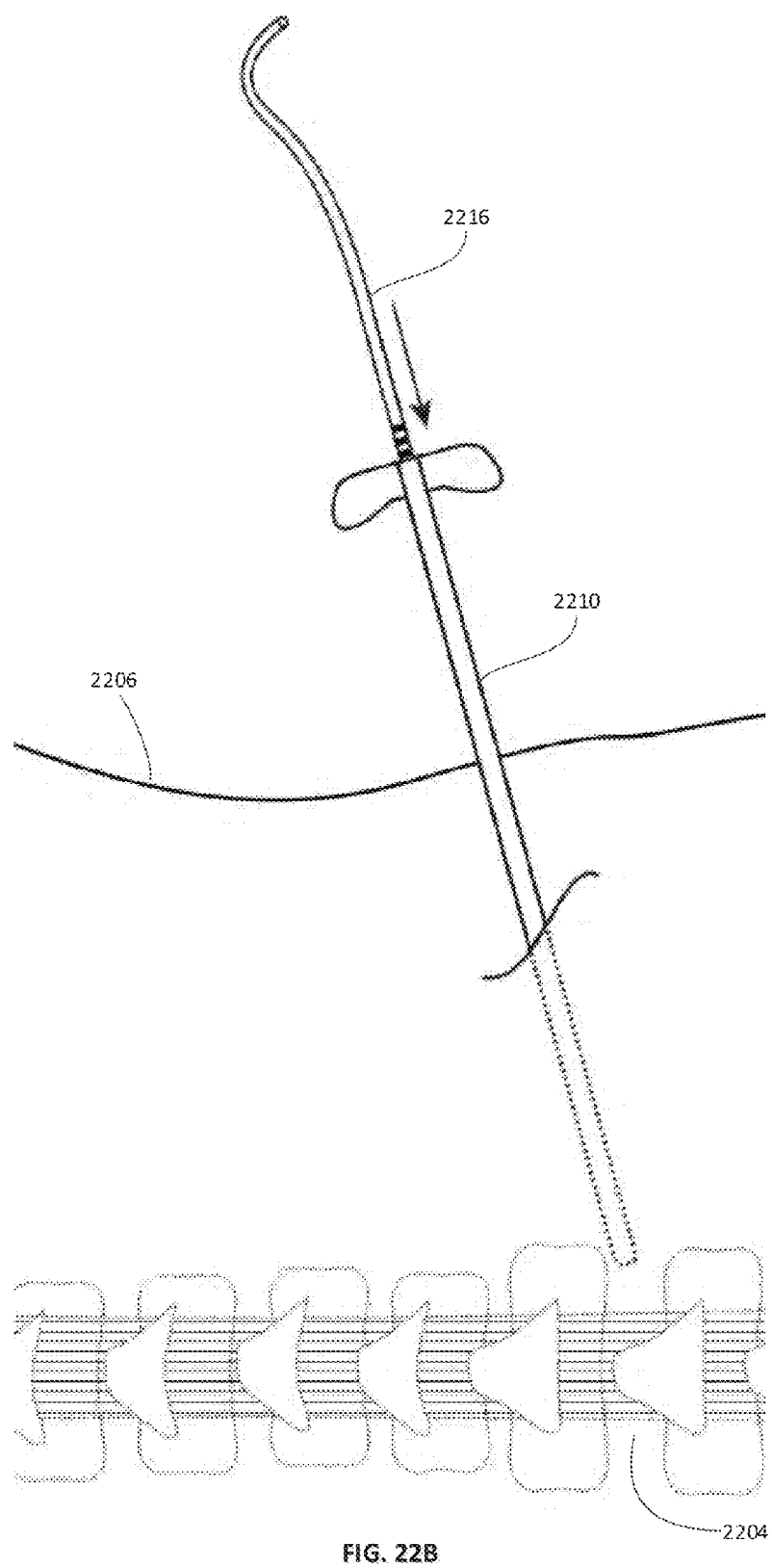

FIG. 22B illustrates gliding of the wireless lead 2216 through the lumen of the introducer 2210. The Introducer 2210 contains an inner lumen that allows a wireless lead 2216 of diameter up to 2.2 mm to progress to its distal tip located at a spinal nerve root or nerve bundle.

Figure 22C:
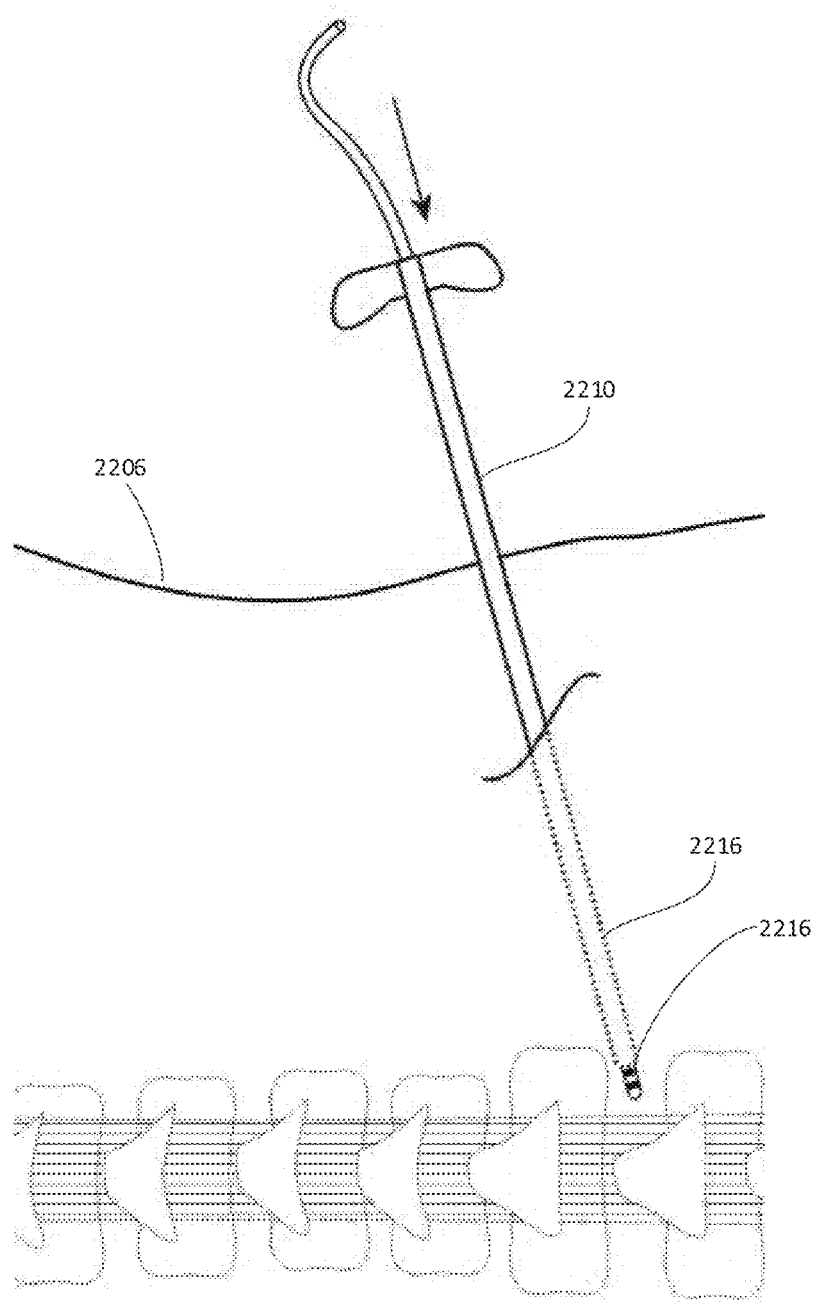

FIG. 22C illustrates placing the distal tip of the wireless lead 2216 at the targeted spinal nerve root or nerve bundle 2202. While targeting the nerve root, wireless lead 2216 can be energized through an external microwave field stimulator, such as one described above (not depicted). Introducer 2210 is used during testing of the wireless lead's location because it is made of materials that do not interfere with the RF coupling, such as PTFE, Pebax, polyurethane, silicon or the like. Once the lead is tested and confirmed to be in the correct location, introducer 2210 is retracted.

Figure 22D:
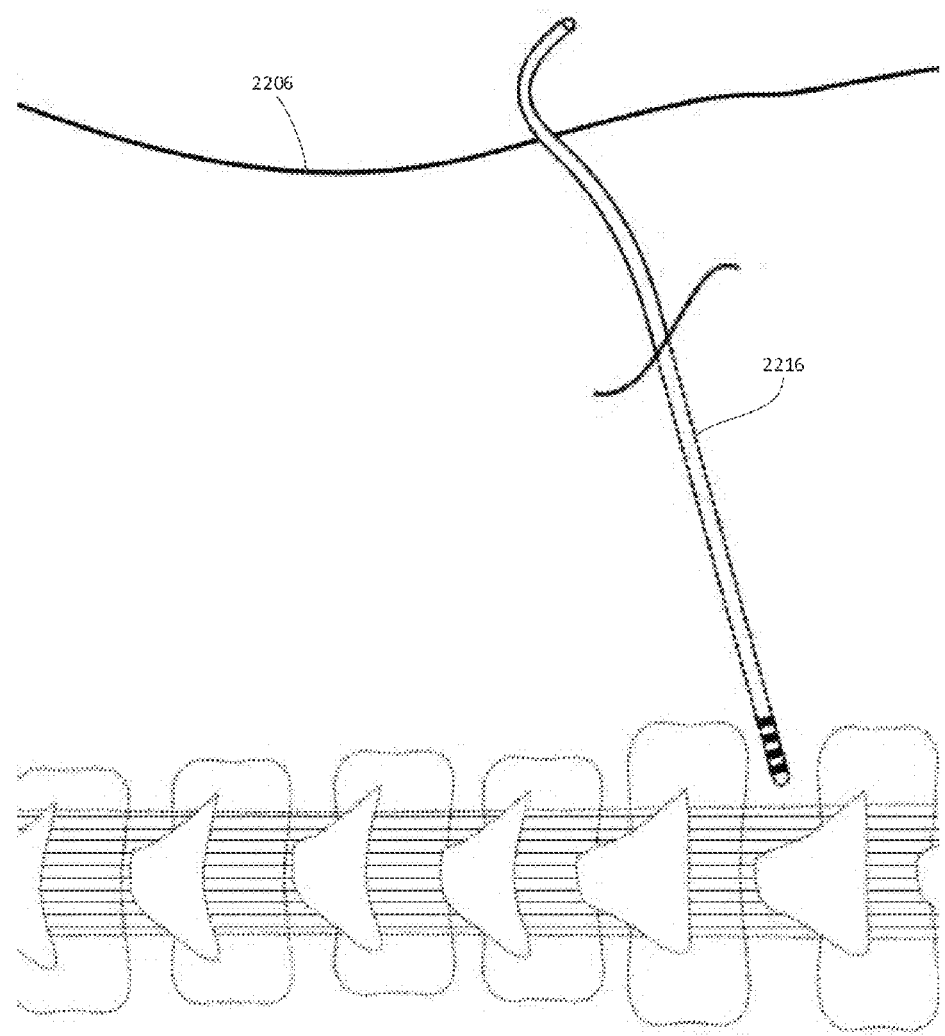

FIG. 22D illustrates the final placement of the wireless lead 2216 following retraction of introducer 2210 and prior to final anchoring. For final anchoring, wireless lead 2216's proximal portion is severed near entry point 2206 (not depicted). The proximal portion of wireless lead 2216 does not contain cables or electronics, which allows the device to be pierced and cut for direct suturing to tissue. In certain embodiments, the proximal portion of the wireless lead is sutured just below the surface of the patient's skin and the distal end of wireless lead 2116 may be "free floating" at the target site adjacent, or in close proximity, to the exiting spinal nerves.

Figure 23:
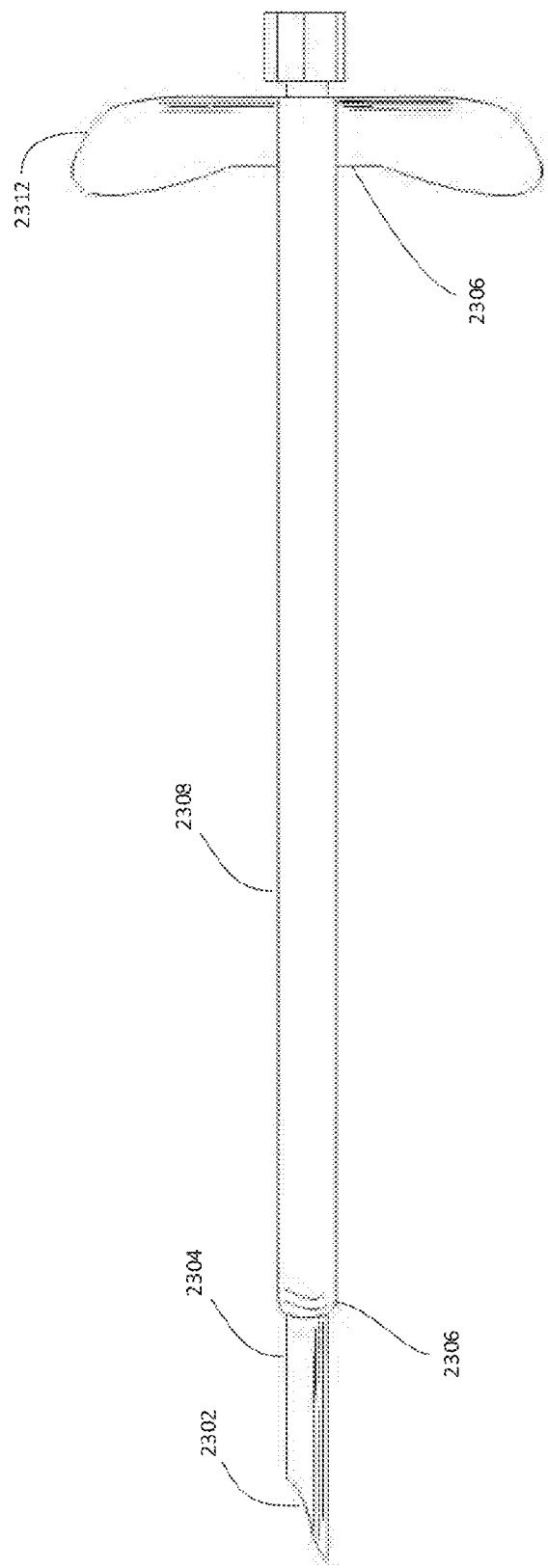
FIG. 23 is an illustration of the injection system to place the lead directly though the transforminal space or directly into the sacral plexus.

FIG. 23 is an illustration of the injection system to place the lead directly though the transforminal space or directly into the sacral plexus. The injection system comprises a metallic spinal needle 2304 and a non-metallic introducer sheath 2308. The spinal needle contains a sharpened tip with a spoonbill feature 2302 for piercing and navigating devices out of its distal tip directionally. On the proximal tip 2314 of the spinal needle is an inner lumen port allowing for devices with diameters up to 1.6 mm to enter. The spinal needle's handle 2312 allows the operator to rotate the device to orient the spoonbill 2302 into the desired direction. Spinal needle 2304 is made of a biocompatible metal such as Stainless Steel. Spinal needle may have a bore length from 2 in to 7 in, and an ID from between about 0.8 mm to 1.6 mm. The injector system's plastic introducer 2308 is made of a biocompatible plastic such as PTFE, pebax, polyurethane, or silicon. The introducer has a rounded distal mouth 2306 to prevent any damage to nerves as the device is navigated. The introducer's handle 2312 is used to further navigate the introducer to the targeted nerve bundles. Introducer 2308 may have a length from between about 1.5 in to 6.8 in; its total length should be driven to be less than the bore length of the spinal needle 2304.

The stimulation parameters of the above-described methods and devices may be suitable for managing chronic pain. It is estimated that over half of the patients with chronic low back pain have facet joint pain due to inflammation in the facet joint. This pain may present as neuropathic or nociceptive pain, with spontaneous initiation. The wireless stimulation devices and methods described herein may provide titratable, long-lasting benefits to patients suffering from chronic pain. In particular, various embodiments of the wireless stimulation device described herein may be an optimal way to achieve chronic facet joint nerve stimulation because the wireless electrodes of the present invention can be implanted or near the facet joints at the site of the pain.

The stimulation parameters of the above-described methods and devices may also be used to treat pain in areas that have been successfully treated with temporary nerve blocks. Regional nerve blockage, or nerve block, is a general term used to refer to the injection of local anesthetic onto or near nerves for temporary control of pain. It can also be used as a diagnostic tool to identify specific nerves as pain generators. Typically, a local anesthetic, such as lidocaine or the like, is delivered to the target site with a introducer, such as a needle. The anesthetic may also be combined with epinephrine, a steroid (corticosteroid) and/or opioids. The physician then assesses whether the nerve block has reduced and/or eliminated the patient's pain. If it has not, the physician may inject one or more additional nerve blocks to one or more alternative target areas to discover the pain generating nerves.

Once a target site for a pain generating nerve has been located, a wireless stimulation device, such as described in this invention, is implanted at the target site through one of the methods described herein. An input signal is delivered to one or more receiving antenna(s) within the wireless lead through radiative coupling. The wireless stimulation device comprises circuitry (as described above) to transform the input signal into one or more electrical impulses and then sends the electrical impulse(s) through one or more electrodes within the lead to modulate the nerves or nerve ganglions at the target site. This method allows the physician to precisely target a pain generating nerve and provide a more permanent reduction of the pain for the patient.

The stimulation parameters of the above-described methods and devices may also be used to reduce or eliminate post-operative pain after surgery. Post-operative pain is a complex response to tissue trauma during surgery that includes both incision pain and pain resulting from hypersensitivity of the central nervous system. Post-operative pain often increases the possibility of post-surgical complications, raises the cost of medical care and, most importantly, interferes with the recovery and return to normal activities of daily living.

In this aspect of the invention, a surgical procedure is performed on the patient, and a wireless stimulation device such as those described above is implanted in or around the surgery site prior to closing any open tissue incision. Similar to the above embodiments, an input signal is transmitted from an external controller to one or more receiving antenna(s) on the wireless stimulation device and converted into one or more electrical impulse(s). The electrical impulse(s) are transmitted through one or more electrodes on the wireless stimulation device to neural tissue at the operative site to modulate this tissue. The application of electrical stimulation to a surgery site post-operatively will reduce post-operative pain and potentially decrease recovery time.

One example of surgical procedures that can be improved with the present invention are spinal procedures, such as posterolateral fusions, interbody fusions (i.e., ALIFs, TLIFs and/or PLIFs), artificial disc replacements, discectomies and the like. With fusion procedures, such as a TLIF, the technique is used to stabilize the spinal vertebra and the disc. Lumbar fusion surgery is designed to create solid bone between the adjoining vertebrae, eliminating any movement between the bones. Supplementary bone tissue, either from the patient (autograft) or a donor (allograft) is used in conjunction with the body's natural growth processes to fuse the vertebrae. The goal of the surgery is to reduce pain and nerve irritation caused by abnormal motion of the vertebrae. However, the surgery itself often creates significant post-operative pain and nerve irritation that may last for 2-8 weeks. The present invention provides a method for reducing or eliminating this post-operative pain through electrical stimulation of the nerves in or around the surgical site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for modulating excitable tissue in a body of a patient comprising:
   implanting a wireless stimulator device in proximity to an exiting nerve root or a dorsal root ganglion, the wireless stimulator device including one or more electrodes, circuitry, and one or more receiving antennas;
   transmitting electrical energy and waveform parameters from a pulse generator located outside of the body to the one or more receiving antennas within the wireless stimulator device through radiative coupling such that the circuitry within the wireless stimulator device generates one or more electrical impulses solely based on the externally supplied electrical energy and according to the externally supplied waveform parameters, and applies the electrical impulses to tissue adjacent to or near the exiting nerve root or the dorsal root ganglion through the electrodes.

2. The method of claim 1 wherein implanting the wireless stimulator device in proximity to an exiting nerve root or a dorsal root ganglion comprises implanting the wireless stimulator device such that the wireless stimulator device is completely contained with the body of the patient.

3. The method of claim 1 wherein the electrical impulses have a frequency equal to or less than 1 KHZ and a duty cycle of less than 10%.

4. The method of claim 2 wherein implanting the wireless stimulator device comprises implanting a wireless stimulator device that has a diameter equal to or less than 1.8 mm.

5. The method of claim 2 wherein implanting the wireless stimulator device comprises:
   advancing at least a portion of the wireless stimulator device through an intervertebral foramen into Kambin's triangle; and
   anchoring said portion of the wireless stimulator device in Kambin's triangle and in proximity to the exiting nerve root or the dorsal root ganglion.

6. The method of claim 5 wherein advancing at least a portion of the wireless stimulator device comprises:
   placing a lumen near an opening of the intervertebral foramen; and
   advancing said portion of the wireless stimulator device through the lumen and out of a distal opening of the lumen distal to the opening of the intervertebral foramen.

7. The method of claim 6 wherein the lumen is part of a cannula, spinal needle or endoscope.

8. The method of claim 5 wherein anchoring said portion of the stimulator device comprises suturing said portion of the wireless stimulator device to tissue or bone adjacent to or near Kambin's triangle.

9. The method of claim 8 wherein the tissue or bone includes one of a facet joint, a vertebral body, a pedicle, an annulus or a facet capsule.

10. The method of claim 8 wherein anchoring said portion of the wireless stimulator device further comprises embedding one or more fixation prongs on said portion of the lead in tissue.

11. The method of claim 2 wherein implanting the wireless stimulator device comprises implanting the wireless stimulator device at a dermatome level from L5 to T10 and at an angle of no greater than 45 degrees.

12. The method of claim 2 wherein implanting the wireless stimulator device comprises advancing the wireless stimulator device through a sacral hiatus.

13. The method of claim 12 further comprising implanting the wireless stimulator device at a dermatome level from L5 to T12.

14. The method of claim 2 wherein the wireless stimulator device comprises one of a suturing addendum, a fixation prong or a screw-tip.

15. A method for modulating excitable tissue within a body of a patient comprising:
implanting a wireless stimulator device through an intervertebral foramen opening into Kambin's triangle, the wireless stimulator device including one or more electrodes, circuitry, and one or more receiving antennas;
anchoring the electrodes in close proximity to a nerve or a nerve ganglion; and
transmitting electrical energy and waveform parameters from a pulse generator located outside the body of the patient to the one or more receiving antennas within the wireless stimulator device through radiative coupling such that the circuitry within the wireless stimulator device generates one or more electrical impulses solely based on the externally supplied electrical energy and according to the externally supplied waveform parameters, and applies the electrical impulses to tissue adjacent to or near the nerve root or the nerve ganglion in surrounding tissue through the electrodes.

16. The method of claim 15, wherein anchoring the electrodes comprises fixating at least a distal portion of the wireless stimulator device such that the electrodes, the circuitry and the receiving antenna are completely contained within the patient's body.

17. The method of claim 16 wherein implanting the wireless stimulator device further comprises: advancing the wireless stimulator device through a lumen and out of a distal end of the lumen such that said distal portion of the wireless stimulator device passes through the intervertebral foramen opening.

18. The method of claim 16 wherein anchoring the electrodes further comprises suturing said portion of the wireless stimulator device to tissue or bone adjacent to or near Kambin's triangle.

19. The method of claim 18 wherein the tissue or bone comprises one of a facet joint, a vertebral body, a pedicle, an annulus or a facet capsule.

20. The method of claim 16 wherein anchoring the electrodes further comprises embedding fixation prongs on the wireless stimulator device into tissue in the Kambin's triangle.

21. The method of claim 20 wherein embedding fixation prongs further comprises rotating screw-tips on the wireless stimulator device into tissue in the Kambin's triangle.

22. A method for modulating excitable tissue in a body of a patient comprising:
implanting a wireless stimulator device through a sacral hiatus opening into an epidural space of a spinal cord of the patient, the wireless stimulator device including one or more electrodes, circuitry, and one or more receiving antennas;
positioning the electrodes in an intervertebral foraminal space in close proximity to a nerve or a nerve ganglion; and
transmitting electrical energy and waveform parameters from a pulse generator located outside the body of the patient to the one or more receiving antennas through radiative coupling such that the circuitry within the wireless stimulator device generates one or more electrical impulses solely based on the externally supplied electrical energy and according to the externally supplied waveform parameters, and applies the electrical impulses to tissue adjacent to or near the nerve root or the nerve ganglion through the electrodes.

23. The method of claim 22 wherein anchoring the electrodes comprises fixating at least a distal portion of the wireless stimulator device such that the electrodes, the circuitry and the receiving antennas are completely contained within the patient's body.

24. A device for modulating excitable tissue in a patient's body comprising:
a wireless stimulator device comprising one or more electrodes, circuitry and a receiving antenna, the wireless stimulator device sized and configured for placement in close proximity to an exiting nerve root or a dorsal root ganglion;
wherein the receiving antenna is configured to receive an input signal containing electrical energy and waveform parameters through radiative coupling from a transmitter located outside of the patient's body; and
wherein the circuitry is configured to generate an electrical impulse solely based on the externally supplied electrical energy and according to the externally supplied waveform parameters, the electrical impulse being sufficient to modulate a nerve or a nerve ganglion at the target site.

25. The device of claim 24 wherein the wireless stimulator device has a diameter of less than 1.8 mm.

26. The device of claim 24 wherein the electrical impulse has a frequency of 1 KHZ or less and a duty cycle of less than 10%.

27. The device of claim 24 wherein the distal portion of the wireless stimulator device is sized and shaped for advancement through an intervertebral foramen into Kambin's triangle.

28. The device of claim 27 wherein the distal portion of the wireless stimulator device further comprises one or more fixation elements for attaching said distal portion to tissue or bone adjacent to or near the Kambin's triangle.

29. The device of claim 28 wherein the fixation elements comprise one of a suturing addendum, a rotating screw-tip or a fixation prong.

30. The device of claim 24 wherein the wireless stimulator device comprises a distal portion containing the electrodes, the circuitry and the receiving antenna, said distal portion being sized and shaped for advancement through a sacral hiatus opening into an epidural space of a spinal cord of the patient and positioning within an intervertebral foraminal space.

31. A device for treating pain in a body of a patient comprising:
a wireless stimulator device comprising a distal portion containing one or more electrodes, circuitry and a receiving antenna, said distal portion having a diameter less than 1.8 mm; and
wherein the receiving antenna is configured to receive an input signal containing electrical energy and waveform parameters through radiative coupling from a transmitter located outside of the patient's body; and
wherein the circuitry is configured to generate an electrical impulse solely based on the externally supplied electrical energy and according to the externally supplied waveform parameters, the electrical impulse being sufficient to modulate a nerve or a nerve ganglion at a target site with the patient's body.

32. The device of claim 31 wherein the target site is located at least 10 cm beneath an outer skin surface of the patient's body.

33. The device of claim 31 wherein the target site is located about 13 cm beneath an outer skin of the patient's body.

34. The device of claim 31 wherein the distal portion of the wireless stimulator device is sized and configured for advancement through an intervertebral foramen into Kambin's triangle.

35. The device of claim 31 wherein the distal portion of the wireless stimulator device further comprises one or more fixation elements for attaching said distal portion to tissue or bone adjacent to or near the Kambin's triangle.

36. The device of claim 35 wherein the fixation elements comprise one of a suturing addendum, a rotating screw-tip or a fixation prong.

37. The device of claim 31 wherein the receiving antenna comprises a dipole antenna.

38. A system for modulating excitable tissue in a body of a patient comprising:
a wireless stimulator device comprising one or more electrodes and a receiving antenna, the wireless stimulator device sized and configured for placement in close proximity to an exiting nerve root or a dorsal root ganglion; and
a control device having a transmitter located outside of the patient's body and configured to transmit an input signal containing electrical energy and waveform parameters to the receiving antenna through radiative coupling; and
wherein the wireless stimulator device is configured to generate an electrical impulse solely based on the externally supplied electrical energy and according to the externally supplied waveform parameters, the electrical impulse being sufficient to modulate a nerve or a nerve ganglion at a target site within the patient's body.

39. The system of claim 38 wherein the control device comprises a transmitting antenna configured to transmit the input signal through a carrier signal having a frequency between about 800 KHz and 5.8 GHz.

40. The system of claim 38 wherein the control device comprises a pulse generator configured to generate an electrical impulse with a frequency of about 10 to 500 Hz.

41. The system of claim 38 wherein the control device is configured to transmit the input signal at least 10 cm from an outer skin surface of the patient through tissue to the target site.

42. The system of claim 38 wherein the control device is configured to transmit the input signal 13 cm from an outer skin surface of the patient through the tissue to the target site.

43. The system of claim 38 wherein the wireless stimulator device comprises a distal portion having a diameter less than about 1.8 mm.

44. The system of claim 38 wherein the wireless stimulator device is sized and configured for advancement through an intervertebral foramen into Kambin's triangle.

45. A method for modulating excitable tissue within a body of a patient comprising:
applying one or more nerve blocks to one or more target areas within the body of the patient;
selecting one of the one or more target areas based on feedback from the patient;
positioning a wireless stimulator device at the selected target areas, the wireless stimulator device including one or more electrodes, circuitry, and one or more receiving antennas;
transmitting an input signal containing energy and waveform parameters from a pulse generator located outside the body of the patient to the wireless stimulator device through radiative coupling such that the circuitry within the wireless stimulator device generates an electrical impulse solely based on the externally supplied electrical energy and according to the externally supplied waveform parameters, and applies the electrical impulse to excitable tissue at the target areas through one or more electrodes on the wireless stimulator device to treat pain.

46. A method for treating post-operative pain comprising:
performing a surgical procedure at a target site in a body of a patient;
positioning a wireless stimulator device at the target site, the wireless stimulator device including one or more electrodes, circuitry, and one or more receiving antennas and;
transmitting an input signal containing energy and waveform parameters from a pulse generator outside the body of the patient to the wireless stimulator device through radiative coupling such that the circuitry within the wireless stimulator device generates the electrical impulse solely based on the externally supplied electrical energy and according to the externally supplied waveform parameters, and applies the electrical impulse to excitable tissue at the target site through the one or more electrodes on the wireless stimulator device to mitigate the post-operative pain.

* * * * *